US012319714B2

(12) United States Patent
Gumrukcu

(10) Patent No.: US 12,319,714 B2
(45) Date of Patent: Jun. 3, 2025

(54) COMPOSITIONS AND METHODS FOR TREATING VIRAL INFECTIONS

(71) Applicant: G TECH BIO LLC, Los Angeles, CA (US)

(72) Inventor: Serhat Gumrukcu, Los Angeles, CA (US)

(73) Assignee: G TECH BIO LLC, Los Angeles, CA (US)

( * ) Notice: Subject to any disclaimer, the term of this patent is extended or adjusted under 35 U.S.C. 154(b) by 798 days.

(21) Appl. No.: 17/005,733

(22) Filed: Aug. 28, 2020

(65) Prior Publication Data

US 2021/0238232 A1 Aug. 5, 2021

Related U.S. Application Data

(60) Provisional application No. 62/985,597, filed on Mar. 5, 2020, provisional application No. 62/976,491, filed on Feb. 14, 2020, provisional application No. 62/968,387, filed on Jan. 31, 2020, provisional application No. 62/896,460, filed on Sep. 5, 2019.

(51) Int. Cl.

| | |
|---|---|
| ***C12N 15/00*** | (2006.01) |
| ***A61K 31/70*** | (2006.01) |
| ***A61K 48/00*** | (2006.01) |
| ***C07K 14/005*** | (2006.01) |
| ***C12N 7/00*** | (2006.01) |
| ***C12N 15/63*** | (2006.01) |
| ***C12N 15/86*** | (2006.01) |
| *A01K 67/00* | (2006.01) |
| *A61K 38/00* | (2006.01) |

(52) U.S. Cl.

CPC .............. *C07K 14/005* (2013.01); *C12N 7/00* (2013.01); *C12N 15/86* (2013.01); *A61K 38/00* (2013.01); *C12N 2730/10122* (2013.01); *C12N 2730/10123* (2013.01); *C12N 2730/10133* (2013.01); *C12N 2750/14143* (2013.01)

(58) Field of Classification Search

CPC .................. C07K 14/005; C12N 15/86; C12N 2750/14143; C12N 2730/10123; C12N 2730/10133; C12N 2730/10122

See application file for complete search history.

(56) References Cited

U.S. PATENT DOCUMENTS

| | | | |
|---|---|---|---|
| 10,214,567 B2 * | 2/2019 | Guo et al. | |
| 2001/0049145 A1 | 12/2001 | Ryu et al. | |
| 2004/0224389 A1 * | 11/2004 | Bellgrau et al. | |
| 2018/0312546 A1 | 11/2018 | Guo et al. | |

FOREIGN PATENT DOCUMENTS

| | | | |
|---|---|---|---|
| JP | 2002320480 A | 11/2002 | |
| WO | 200053775 | 9/2000 | |
| WO | WO-2006135413 A2 * | 12/2006 | ............ A61K 39/12 |
| WO | WO-2015044292 A1 * | 4/2015 | ............ A61K 38/50 |

OTHER PUBLICATIONS

Protzer, et al. “Interferon gene transfer by a hepatitis B virus vector efficiently suppresses wild-type virus infection” Proc. Natl. Acad. Sci. US. Sep. 1999, vol. 96, pp. 10818-10823.

Written Opinion and Search Report cited in related Singapore Application No. 11202201670R dated Sep. 30, 2024.

English translation of Japanese Office Action cited in Japanese Patent Application No. 2022-513124, dated Sep. 24, 2024, 6 pages.

* cited by examiner

*Primary Examiner* — Quang Nguyen

(74) *Attorney, Agent, or Firm* — LEASON ELLIS LLP

(57) ABSTRACT

The disclosure provides methods and compositions utilizing recombinant nucleic acid constructs or a replication incompetent virus-like particle encoding a chemokine, cytokine, or apoptosis inducing protein (e.g. Caspase 9 (Casp9)), or other toxins in a form which can only be transcribed in the presence of a viral polymerase. These methods can be adapted to target many viral infections and reduce or eliminate viral load, and provide a fundamentally different treatment for viral infections.

18 Claims, 32 Drawing Sheets

Specification includes a Sequence Listing.

FIGURES 1A-B
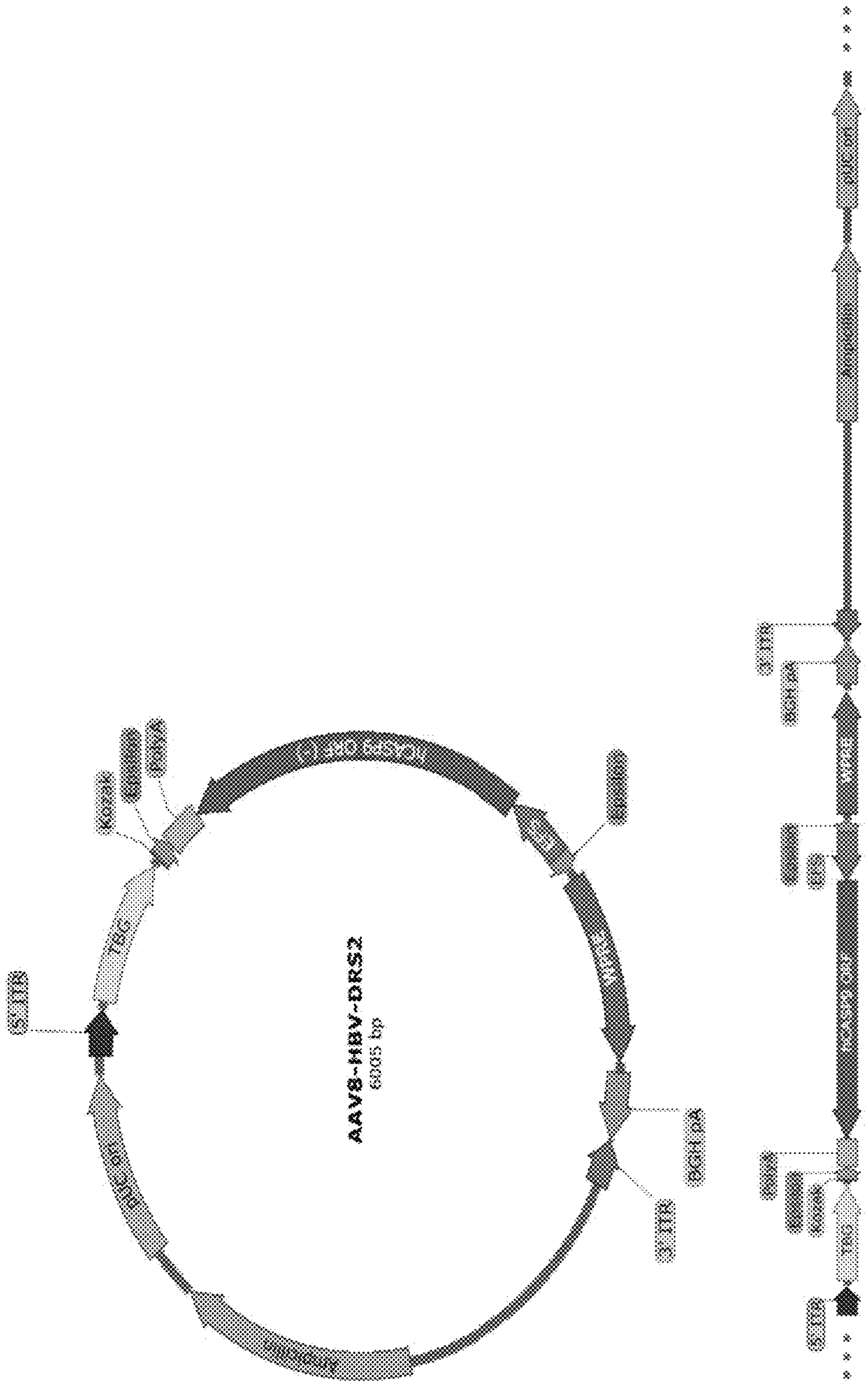

Experiment 1

| | |
|---|---|
| **Date** | 6.7.2019 |
| **Cell Conc.** | 4e5/ml |
| **Plate** | 24-well |
| **Cell #** | 1.6e5/well |

AAV8-HBV-DRS1 (EF1a > HBV-rcCasp9)

| | |
|---|---|
| **Group 1** | Untransduced |
| **Group 2** | MOI 1e4 |
| **Group 3** | MOI 1e5 |

HepG2

| **24h** | Total (e5) | Via % | Live (e5) |
|---|---|---|---|
| Group 1 | 5.29 | 98.7 | 5.23 |
| | 4.78 | 98.1 | 4.69 |
| Group 2 | 4.11 | 98.2 | 4.03 |
| | 4.61 | 98 | 4.51 |
| Group 3 | 3.82 | 99.2 | 3.79 |
| | 4.33 | 98.3 | 4.26 |

HepAD38

| **24h** | Total (e5) | Via % | Live (e5) |
|---|---|---|---|
| Group 1 | 4.41 | 98.4 | 4.34 |
| | 4.1 | 94.6 | 3.88 |
| Group 2 | 4.01 | 98.7 | 3.95 |
| | 4.86 | 96.7 | 4.7 |
| Group 3 | 3.73 | 94.8 | 3.53 |
| | 3.63 | 85.8 | 3.47 |

HepG2

| **48h** | Total (e5) | Via % | Live (e5) |
|---|---|---|---|
| Group 1 | 5.05 | 86.5 | 4.36 |
| | 4.49 | 87.1 | 3.91 |
| Group 2 | 6.52 | 95.9 | 6.25 |
| | 5.51 | 94.5 | 5.21 |
| Group 3 | 7.08 | 96 | 6.79 |
| | 7.1 | 97.1 | 6.89 |

HepAD38

| **48h** | Total (e5) | Via % | Live (e5) |
|---|---|---|---|
| Group 1 | 6.12 | 95.7 | 5.86 |
| | 6 | 95.6 | 5.73 |
| Group 2 | 5.36 | 92.1 | 4.93 |
| | 5.29 | 89.4 | 4.73 |
| Group 3 | 2.98 | 88.7 | 2.64 |
| | 3 | 84.2 | 2.53 |

HepG2

| **65h** | Total (e5) | Via % | Live (e5) |
|---|---|---|---|
| Group 1 | 9.17 | 93.7 | 8.59 |
| | 8.09 | 93.2 | 7.49 |
| Group 2 | 10.3 | 96.9 | 10 |
| | 10.2 | 97.7 | 10 |
| Group 3 | 9.93 | 96.9 | 9.62 |
| | 9.71 | 95 | 9.22 |

HepAD38

| **65h** | Total (e5) | Via % | Live (e5) |
|---|---|---|---|
| Group 1 | 7.96 | 90.8 | 7.23 |
| | 7.13 | 92.5 | 6.6 |
| Group 2 | 7.54 | 89.8 | 6.77 |
| | 7.79 | 88.2 | 6.87 |
| Group 3 | 2.05 | 69.5 | 1.42 |
| | 2.51 | 79 | 1.98 |

FIGURE 2C

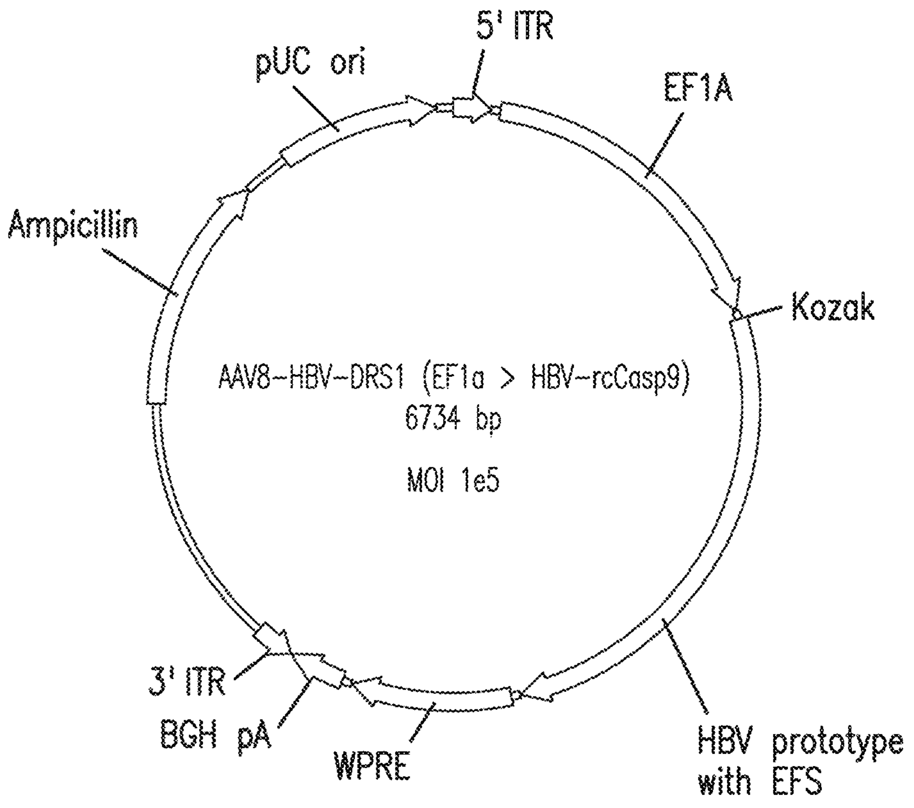
Z-LEHD-FMK, caspase-9 inhibitor
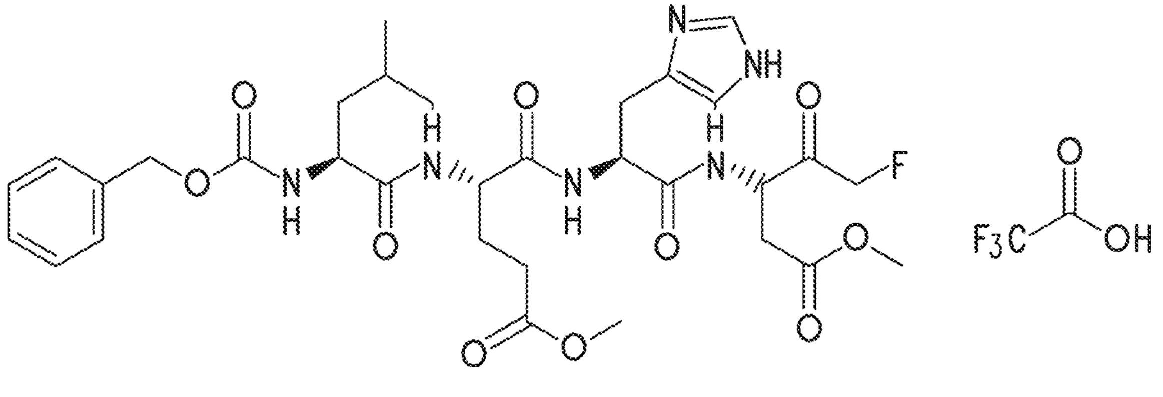
FIGURE 3A

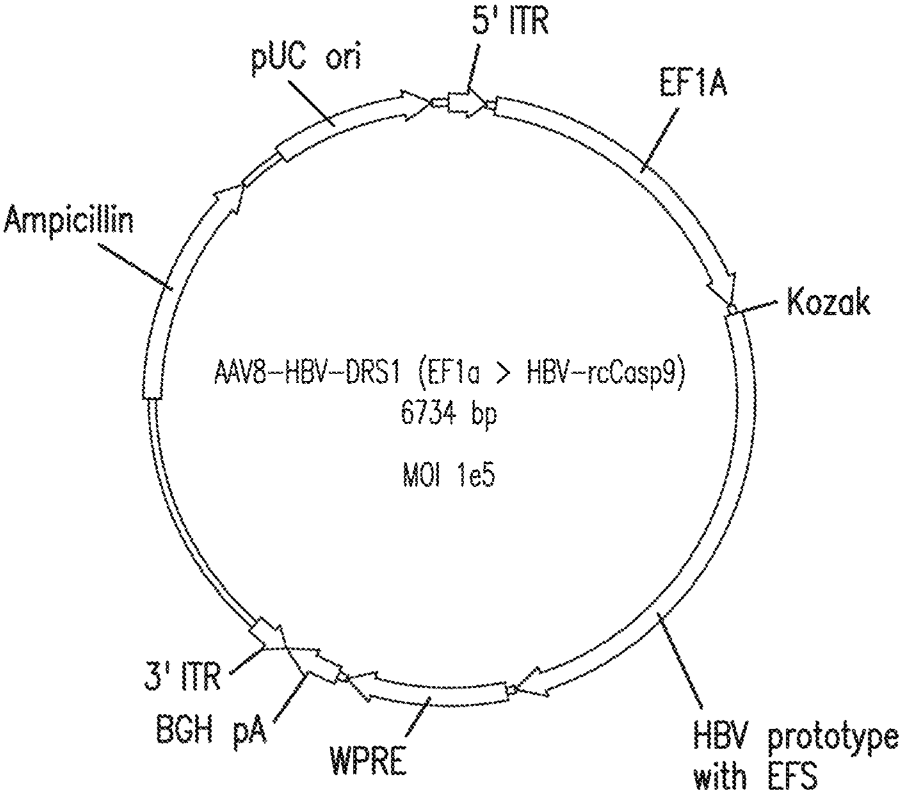
Z-LEHD-FMK, caspase-9 inhibitor
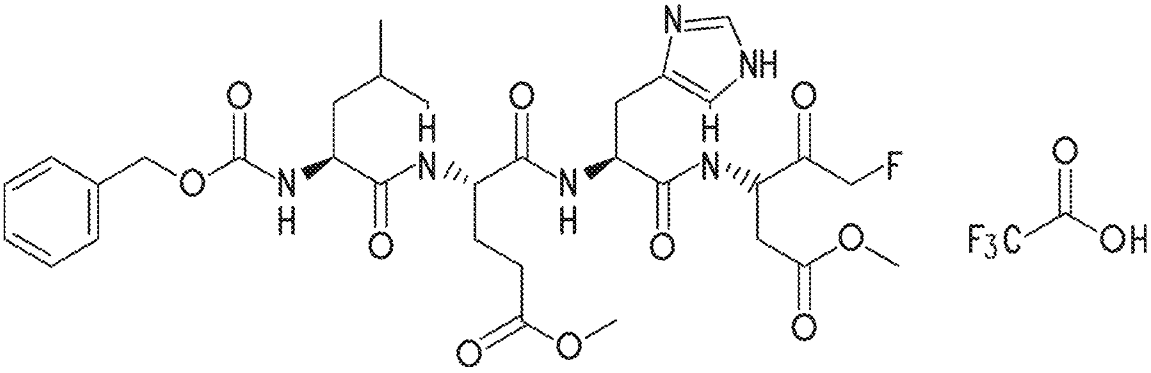
FIGURE 4A

Figure 4C
Experiment 2

| | |
|---|---|
| **Date** | 6.12.2019 |
| **Cell Conc.** | 2.5e5/ml |
| **Plate** | 96-well |
| **Cell #** | 25e3/well |
| **Test Virus** | AAV8-HBV-DRS1 (Ef1a > HBV-rcCasp9) |
| | |
| **Group 1** | Untransduced |
| **Group 2** | Test AAV MOI 1e5 |
| **Group 3** | Test AAV MOI 1e5 + z-LEHD.fmk |
| **Group 4** | GFP AAV MOI 1e5 |
| **Group 5** | GFP AAV MOI 1e5 + z-LEHD.fmk |

| | | **HepG2** | |
|---|---|---|---|
| **48h** | Total (e5) | Via % | Live (e5) |
| Group 1 | 5.73 | 93.3 | 5.34 |
| | 5.82 | 95.5 | 5.53 |
| | 7.14 | 95.7 | 6.84 |
| | | | |
| Group 2 | 4.47 | 84.8 | 3.81 |
| | 6.51 | 87.9 | 5.73 |
| | 6.75 | 92.5 | 6.24 |
| | | | |
| Group 3 | 6.84 | 87.6 | 6 |
| | 6.18 | 85.6 | 5.31 |
| | 6.54 | 83.6 | 5.46 |
| | | | |
| Group 4 | 8.04 | 96.2 | 7.74 |
| | 8.16 | 97.3 | 7.92 |
| | 6.24 | 95.3 | 5.94 |
| | | | |
| Group 5 | N/A | | |

| | | **HepAD38** | |
|---|---|---|---|
| **48h** | Total (e5) | Via % | Live (e5) |
| Group 1 | 4.44 | 90 | 4.02 |
| | 4.26 | 92.4 | 3.96 |
| | 5.43 | 88.8 | 4.83 |
| | | | |
| Group 2 | 3.63 | 81 | 2.93 |
| | 4.38 | 79.3 | 3.48 |
| | 3.48 | 79.1 | 2.44 |
| | | | |
| Group 3 | 5.31 | 84 | 4.44 |
| | 4.41 | 83 | 3.66 |
| | 5.07 | 84.4 | 4.26 |
| | | | |
| Group 4 | N/A | | |
| | | | |
| | | | |
| | | | |
| Group 5 | N/A | | |

Experiment 2

| | |
|---|---|
| **Date** | 6.12.2019 |
| **Cell Conc.** | 2.5e5/ml |
| **Plate** | 96-well |
| **Cell #** | 25e3/well |
| **Test Virus** | AAV8-HBV-DRS1 (Ef1a > HBV-rcCasp9) |
| | |
| **Group 1** | Untransduced |
| **Group 2** | Test AAV MOI 1e5 |
| **Group 3** | Test AAV MOI 1e5 + z-LEHD.fmk |
| **Group 4** | GFP AAV MOI 1e5 |
| **Group 5** | GFP AAV MOI 1e5 + z-LEHD fmk |

| | | **HepG2** | |
|---|---|---|---|
| **48h** | Total (e5) | Via % | Live (e5) |
| Group 1 | 5.73 | 93.3 | 5.34 |
| | 5.82 | 95.5 | 5.55 |
| | 7.14 | 95.7 | 6.84 |
| | | | |
| Group 2 | 4.47 | 84.8 | 3.81 |
| | 6.51 | 87.9 | 5.73 |
| | 6.75 | 92.5 | 6.24 |
| | | | |
| Group 3 | 6.84 | 87.6 | 6 |
| | 6.18 | 85.6 | 5.31 |
| | 6.54 | 83.6 | 5.46 |
| | | | |
| Group 4 | 8.04 | 96.2 | 7.74 |
| | 8.16 | 97.3 | 7.92 |
| | 6.24 | 95.1 | 5.94 |
| | | | |
| Group 5 | N/A | | |

| | | **HepAD38** | |
|---|---|---|---|
| **48h** | Total (e5) | Via % | Live (e5) |
| Group 1 | 4.44 | 90 | 4.02 |
| | 4.26 | 92.4 | 3.96 |
| | 5.43 | 88.8 | 4.83 |
| | | | |
| Group 2 | 3.63 | 81 | 2.93 |
| | 4.38 | 79.3 | 3.48 |
| | 3.48 | 79.1 | 2.44 |
| | | | |
| Group 3 | 5.31 | 84 | 4.44 |
| | 4.41 | 83 | 3.66 |
| | 5.07 | 84.4 | 4.26 |
| | | | |
| Group 4 | N/A | | |
| | | | |
| | | | |
| | | | |
| Group 5 | N/A | | |

FIGURE 4C-1

| | | HepG2 | |
|---|---|---|---|
| **72h** | Total (e5) | Via % | Live (e5) |
| Group 1 | 7.41 | 96.4 | 7.14 |
| | 8.58 | 96.9 | 8.31 |
| | | | |
| | | | |
| Group 2 | 9.54 | 96 | 9.15 |
| | 9.72 | 95.3 | 8.31 |
| | | | |
| | | | |
| Group 3 | 7.71 | 96.3 | 7.44 |
| | 7.5 | 98.1 | 7.35 |
| | | | |
| | | | |
| Group 4 | 14.58 | 98.8 | 14.4 |
| | 12.09 | 97.4 | 11.76 |
| | | | |
| | | | |
| Group 5 | 11.52 | 95.3 | 10.98 |
| | 9.54 | 98.3 | 9.39 |

| | | HepAD38 | |
|---|---|---|---|
| **72h** | Total (e5) | Via % | Live (e5) |
| Group 1 | 7.23 | 95 | 6.87 |
| | 7.23 | 93.3 | 6.75 |
| | 9.18 | 95.4 | 8.76 |
| | | | |
| Group 2 | 2.73 | 97.8 | 2.67 |
| | 1.77 | 96.5 | 1.71 |
| | 1.01 | 98 | 0.99 |
| | | | |
| Group 3 | 6.75 | 94.9 | 6.42 |
| | 6.63 | 96 | 6.36 |
| | 6.51 | 92.1 | 6 |
| | | | |
| Group 4 | 5.4 | 98.5 | 5.34 |
| | 3.64 | 97.8 | 3.52 |
| | 4.47 | 96.5 | 4.32 |
| | | | |
| Group 5 | 5.91 | 94.3 | 5.55 |
| | 5.22 | 96.5 | 5.04 |
| | 6.3 | 98.4 | 6.18 |

| | | HepG2 | |
|---|---|---|---|
| **120h** | Total (e5) | Via % | Live (e5) |
| Group 1 | 13.56 | 91 | 12.32 |
| | 15.84 | 94 | 14.88 |
| | 15.16 | 91.3 | 13.84 |
| | | | |
| Group 2 | 13.2 | 94.1 | 12.4 |
| | 15.64 | 91.9 | 14.4 |
| | 18.28 | 89.9 | 16.44 |
| | | | |
| Group 3 | 13.68 | 96.4 | 13.2 |
| | 13.64 | 95.8 | 13.04 |
| | 12.36 | 94.1 | 11.64 |
| | | | |
| Group 4 | 11.24 | 90.1 | 10.12 |
| | 12.8 | 89 | 11.4 |
| | 11.52 | 88.3 | 10.2 |
| | | | |
| Group 5 | 14.64 | 92.5 | 13.52 |
| | 13.32 | 92.3 | 12.28 |
| | 10.64 | 94 | 10 |

| | | HepAD38 | |
|---|---|---|---|
| **120h** | Total (e5) | Via % | Live (e5) |
| Group 1 | 8.76 | 97.2 | 8.52 |
| | 9.92 | 97.2 | 9.64 |
| | 8.84 | 97.3 | 8.6 |
| | | | |
| Group 2 | 2.7 | 88 | 2.37 |
| | 3.13 | 83.6 | 2.61 |
| | 3.3 | 90 | 2.97 |
| | | | |
| Group 3 | 13.48 | 93.8 | 12.64 |
| | 14.64 | 94.5 | 13.84 |
| | 10.72 | 94.5 | 10.12 |
| | | | |
| Group 4 | 11.36 | 95.6 | 10.88 |
| | 11.08 | 97.1 | 10.76 |
| | 10.32 | 97.3 | 10.04 |
| | | | |
| Group 5 | 8.88 | 98.1 | 8.72 |
| | 12.2 | 97.8 | 9.56 |
| | 8 | 95.9 | 7.68 |

FIGURE 4C-2

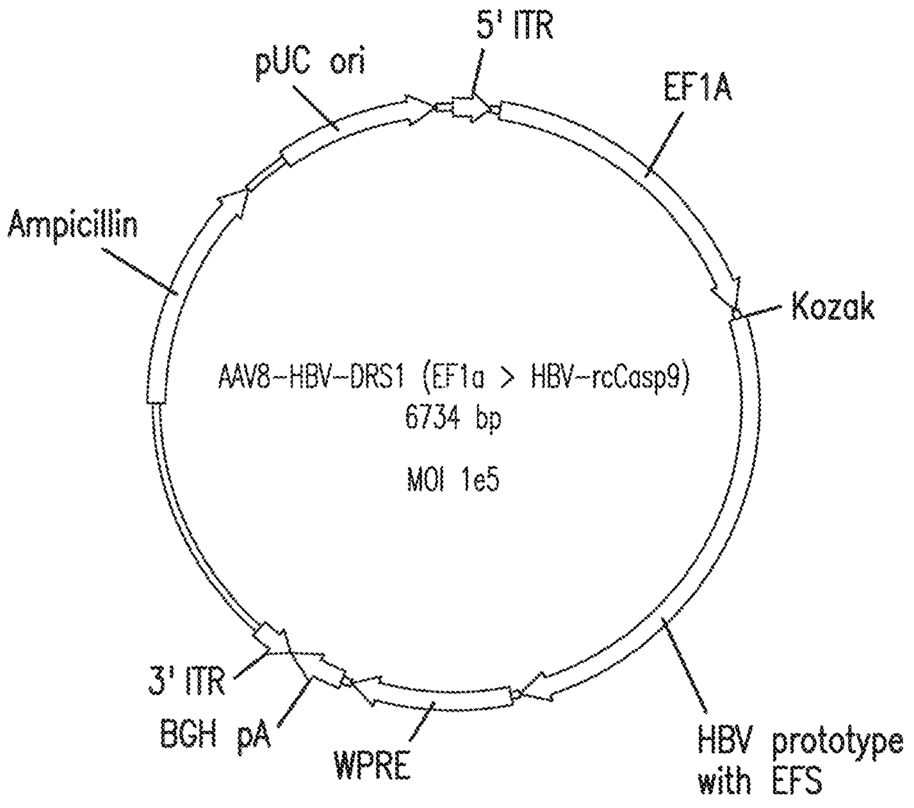
Z-LEHD-FMK, caspase-9 inhibitor
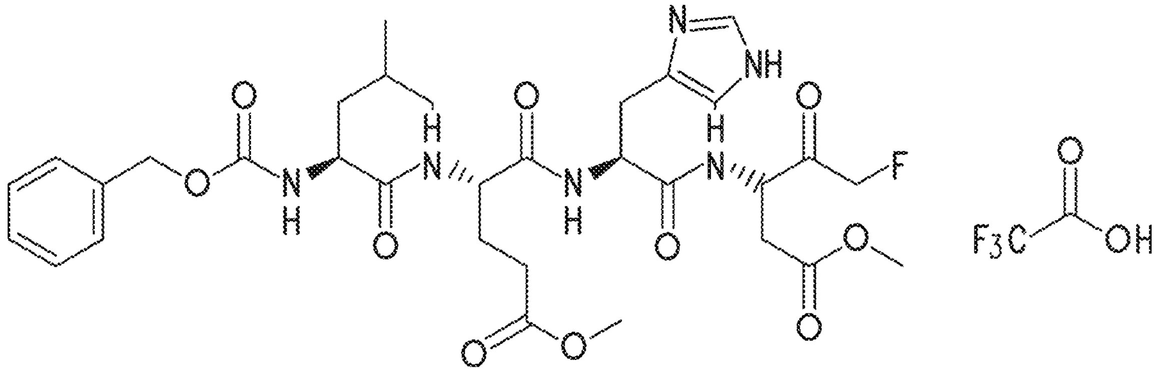
FIGURE 5A

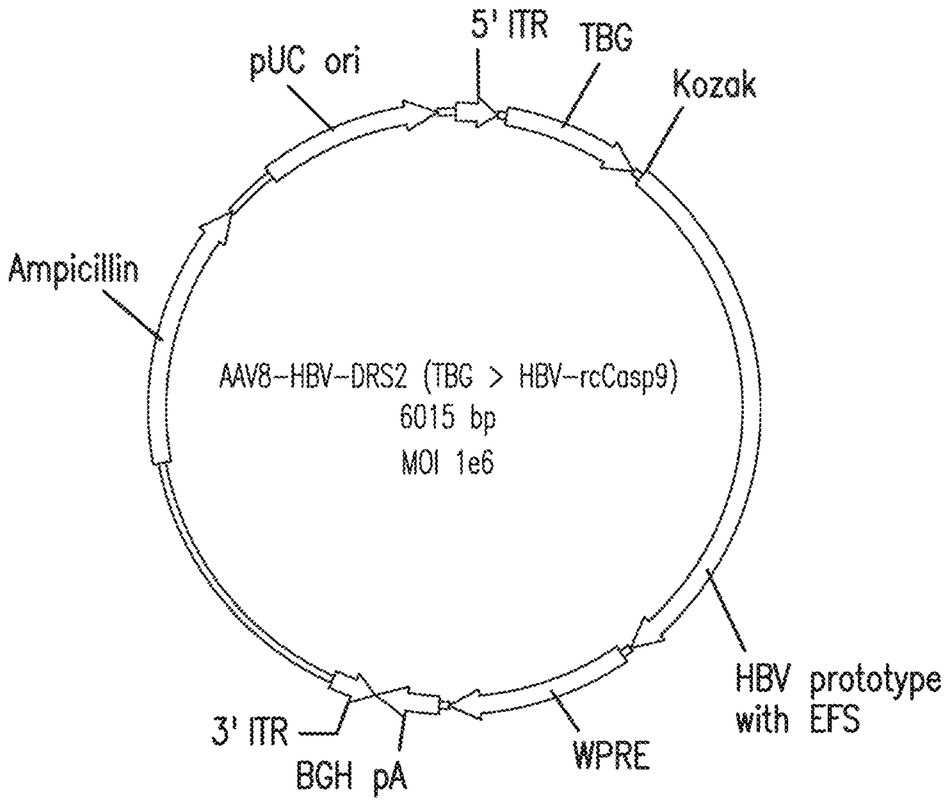
Z-LEHD-FMK, caspase-9 inhibitor
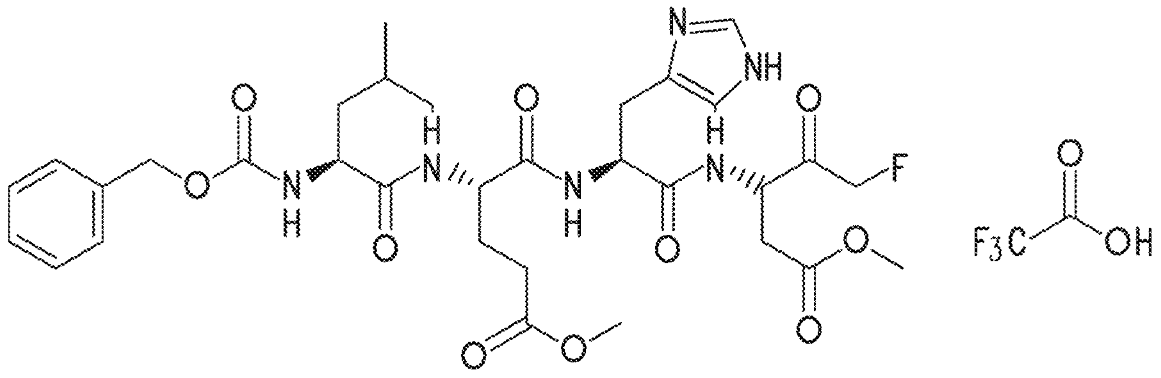
FIGURE 6A

Experiment 3

| | |
|---|---|
| **Date** | 6.17.2019 |
| **Cell Conc.** | 2.5e5/ml |
| **Plate** | 24-well |
| **Cell #** | 1e5/well |
| **Test Virus** | AAV8-HBV-BRS2 (TBG > HBV-ccCasp9) |
| | |
| **Group 1** | Untransduced |
| **Group 2** | Test AAV MOI 1e6 |
| **Group 3** | Test AAV MOI 1e6 + z-LEHD.fmk |
| **Group 4** | z-LEHD.fmk |
| **Group 5** | GFP AAV MOI 1e6 |
| **Group 6** | GFP AAV MOI 1e6 + z-LEHD.fmk |

| | | **HepG2** | | | | | **HepAD38** | | | |
|---|---|---|---|---|---|---|---|---|---|---|
| **48h** | Total (e5) | Via % | Live (e5) | | **48h** | Total (e5) | Via % | Live (e5) | | |
| Group 1 | 2.2 | 75.2 | 1.66 | | Group 1 | 2.28 | 64.6 | 1.47 | | |
| | 1.98 | 57.1 | 1.13 | | | 2.26 | 73.2 | 1.65 | | |
| | 1.74 | 76.7 | 1.33 | | | 2.2 | 75.2 | 1.65 | | |
| Group 2 | 2.8 | 71.7 | 2 | | Group 2 | 1.68 | 63.9 | 1.07 | | |
| | 2.81 | 71.9 | 2.02 | | | 1.9 | 58.5 | 1.11 | | |
| | 2.12 | 71.8 | 1.52 | | | 1.57 | 50 | 0.78 | | |
| Group 3 | 2.67 | 75 | 2 | | Group 3 | 3.6 | 66.9 | 2.41 | | |
| | 3.45 | 74.3 | 2.57 | | | 4.14 | 66.2 | 2.73 | | |
| | 2.43 | 72.9 | 1.77 | | | 3.75 | 70.3 | 2.64 | | |
| Group 4 | 2.1 | 65.4 | 1.37 | | Group 4 | 2.21 | 75.7 | 1.67 | | |
| | 2.02 | 71 | 1.43 | | | 2.34 | 64.7 | 1.52 | | |
| | 1.9 | 73.4 | 1.4 | | | 2.55 | 73.8 | 1.88 | | |
| Group 5 | 2.06 | 61 | 1.26 | >>>>>>>>>> | Group 5 | 1.9 | 75.5 | 1.43 | >>>>>>>>>> | **Both cells GFP expression 89%** |
| | 1.92 | 83.2 | 1.6 | | | 2.58 | 70.3 | 1.82 | | |
| | 1.7 | 82.1 | 1.39 | | | 1.88 | 69.9 | 1.31 | | |
| Group 6 | 2.04 | 62.6 | 1.28 | >>>>>>>>>> | Group 6 | 2.75 | 84.6 | 2.32 | >>>>>>>>>> | **Both cells GFP expression 88%** |
| | 2.12 | 66.7 | 1.41 | | | 2.82 | 78.1 | 2.21 | | |
| | 2.18 | 63 | 1.37 | | | 2.2 | 67.9 | 1.49 | | |

FIGURE 6C-1

HepG2

| 144h | Total (e5) | Via % | Live (e5) | |
|---|---|---|---|---|
| Group 1 | 2.28 | 95.2 | 2.18 | |
| | 1.98 | 98.6 | 1.95 | |
| | 2.5 | 95.1 | 2.38 | |
| Group 2 | 2.44 | 90.1 | 2.2 | |
| | 2.42 | 80.5 | 1.96 | |
| | 1.75 | 90.6 | 1.59 | |
| Group 3 | 2.4 | 92.7 | 2.22 | |
| | 1.93 | 87.4 | 1.68 | |
| | 2.04 | 84.1 | 1.71 | |
| Group 4 | 2.22 | 97 | 2.14 | |
| | 2.64 | 97.9 | 2.53 | |
| | 2.28 | 94.3 | 2.14 | |
| Group 5 | 1.74 | 91.3 | 1.6 | >>>>>>>>>> |
| | 1.87 | 95 | 1.78 | |
| | 1.99 | 93.8 | 1.87 | |
| Group 6 | 1.44 | 93.5 | 1.35 | >>>>>>>>>> |
| | 2.56 | 95.8 | 2.46 | |
| | 2.1 | 94.2 | 1.97 | |

HepAD38

| 144h | Total (e5) | Via % | Live (e5) | | |
|---|---|---|---|---|---|
| Group 1 | 3.38 | 97.6 | 3.3 | | |
| | 3.46 | 96.9 | 3.36 | | |
| | 3.06 | 96.8 | 2.96 | | |
| Group 2 | 0.594 | 88.6 | 0.526 | | |
| | 0.742 | 90.9 | 0.674 | | |
| | 0.782 | 89.7 | 0.702 | | |
| Group 3 | 4.14 | 96.7 | 4 | | |
| | 4.16 | 96.8 | 4.02 | | |
| | 4.28 | 95.6 | 4.1 | | |
| Group 4 | 4.74 | 97.2 | 4.62 | | |
| | 4.84 | 97.7 | 4.72 | | |
| | 4.56 | 94.6 | 4.3 | | |
| Group 5 | 3.76 | 96 | 3.6 | >>>>>>>>>> | **Both cells GFP expression 39%** |
| | 3.28 | 96.3 | 3.16 | | |
| | 2.58 | 94.8 | 2.44 | | |
| Group 6 | 2.5 | 95.7 | 2.4 | >>>>>>>>>> | **Both cells GFP expression 34%** |
| | 2.9 | 97.2 | 2.82 | | |
| | 2.68 | 94.9 | 2.54 | | |

| Name | Position | Size (bp) | Type | Description | Application notes |
|---|---|---|---|---|---|
| WPRE | ▒ 3154-3751 | 598 | Miscellaneous | Woodchuck hepatitis virus posttranscriptional regulatory element | Enhances virus stability in packaging cells, leading to higher titer of packaged virus; enhances higher expression of transgenes. |
| BGH pA | ▒ 3782-3989 | 208 | PolyA_signal | Bovine growth hormone polyadenylation signal | Allows transcription termination and polyadenylation of mRNA transcribed by Pol II RNA polymerase. |
| 3' ITR | ▒ complement (3997-4137) | 141 | ITR | AAV 3' inverted terminal repeat | Allows replication of the viral genome and its packaging into virus. |
| Ampicillin | ▒ 5054-5914 | 861 | ORF | Ampicillin resistance gene | Allows E. coli to be resistant to ampicillin. |
| pUC ori | ▒ 6085-6673 | 589 | Rep_origin | pUC origin of replication | Facilitates plasmid replication in E. coli; regulates high-copy plasmid number (500-700). |

Vector Sequence SEQ ID NO: 33

```
1    CCTGCAGGCA GCTGCGCGCT CGCTCGCTCA CTGAGGCCGC CCGGGCAAAG CCCGGGCGTC GGGCGACCTT TGGTCGCCCG GCCTCAGTGA GCGAGCGAGC
101  GCGCAGAGAG GGAGTGGCCA ACTCCATCAC TAGGGGTTCC TTCTAGACAA CTTTGTATAG AAAAGTTGGG CTCCGGTGCC CGTCAGTGGG CAGAGCGCAC
201  ATCGCCCACA GTCCCCGAGA AGTTGGGGGG AGGGGTCGGC AATTGAACCG GTGCCTAGAG AAGGTGGCGC GGGGTAAACT GGGAAAGTGA TGTCGTGTAC
301  TGGCTCCGCC TTTTTCCCGA GGGTGGGGGA GAACCGTATA TAAGTGCAGT AGTCGCCGTG AACGTTCTTT TTCGCAACGG GTTTGCCGCC AGAACACAGG
401  TAAGTGCCGT GTGTGGTTCC CGCGGGCCTG GCCTCTTTAC GGGTTATGGC CCTTGCGTGC CTTGAATTAC TTCCACCTGG CTGCAGTACG TGATTCTTGA
501  TCCCGAGCTT CGGGTTGGAA GTGGGTGGGA GAGTTCGAGG CCTTGCGCTT AAGGAGCCCC TTCGCCTCGT GCTTGAGTTG AGGCCTGGCC TGGGCGCTGG
601  GGCCGCCGCG TGCGAATCTG GTGGCACCTT CGCGCCTGTC TCGCTGCTTT CGATAAGTCT CTAGCCATTT AAAATTTTTG ATGACCTGCT GCGACGCTTT
701  TTTTCTGGCA AGATAGTCTT GTAAATGCGG GCCAAGATCT GCACACTGGT ATTTCGGTTT TTGGGGCCGC GGGCGGCGAC GGGGCCCGTG CGTCCCAGCG
801  CACATGTTCG GCGAGGCGGG GCCTGCGAGC GCGGCCACCG AGAATCGGAC GGGGGTAGTC TCAAGCTGGC CGGCCTGCTC TGGTGCCTGG TCTCGCGCCG
901  CCGTGTATCG CCCCGCCCTG GGCGGCAAGG CTGGCCCGGT CGGCACCAGT TGCGTGAGCG GAAAGATGGC CGCTTCCCGG CCCTGCTGCA GGGAGCTCAA
1001 AATGGAGGAC GCGGCGCTCG GGAGAGCGGG CGGGTGAGTC ACCCACACAA AGGAAAAGGG CCTTTCCGTC CTCAGCCGTC GCTTCATGTG ACTCCACGGA
1101 GTACCGGGCG CCGTCCAGGC ACCTCGATTA GTTCTCGAGC TTTTGGAGTA CGTCGTCTTT AGGTTGGGGG GAGGGGTTTT ATGCGATGGA GTTTCCCCAC
1201 ACTGAGTGGG TGGAGACTGA AGTTAGGCCA GCTTGGCACT TGATGTAATT CTCCTTGGAA TTTGCCCTTT TTGAGTTTGG ATCTTGGTTC ATTCTCAAGC
1301 CTCAGACAGT GGTTCAAAGT TTTTTTCTTC CATTTCAGGT GTCGTGACAA GTTTGTACAA AAAAGCAGGC TGCCACCATG TGTTCATGTC CTACTGTTCA
1401 AGCCTCCAAG CTGTGCCTTG GGTGGCTTTG GGGCATGGAC AAGAGCCAGA CATGATAAGA TACATTGATG AGTTTGGACA AACCACAACT AGAATGCAGT
1501 GAAAAAAATG CTTTATTTGT GAAATTTGTG ATGCTATTGC TTTATTTGTA ACCATTATAA GCTGCAATAA ACAAGTTTAT GATGTTTTAA AGAAAAGTTT
1601 TTTCCGGAGG AAATTAAAGC AACCAGGCAT CTGTTTATAA ATCCCTTTCA CCGAAACAGC ATTAGCGACC CTAAGCAGGA GGGACTGCAG GTCTTCAGAG
1701 TGAGCCCACT GCTCAAAGAT GTCGTCCAGG GTCTCAACGT ACCAGGAGCC ACTCTTGGGG TCCCTCCAGG AAACAAAACC TGGGAAAGTA GAGTAGGACA
1801 CAAAGATGTC ACTGGGTGTG GGCAAACTAG ATATGGCGTC CAGCTGGTCG AAGGTCCTCA AACCTTCCTG GAACGGGGTG GCATCTGCCT CGGGGTTACT
1901 GCCAGGGGAC TCGTCTTCAG GGGAAGTGGA GGCCACCTCA AACCCATGGT CTTTCTGCTC CCCACCACAG GCCTGGATGA AAAAGAGCTT GGGCTTCCCT
2001 CCCAGGCTGG GGCAGCTGGT CCCATTGAAG ATGTTCACAA TCTTCTCGAC CGACACAGGG CATCCATCTG TGCCGTAGAC AGCCCCTGGG AACTGCAGGT
2101 GGCTGGCCTG ACAGCCGTGA GAGAGAATGA CCACCACGCA GCAGTCCAGA GCACCGTGGT CCTGCTGCGC CAGCTCCAGC AAAGCCAGCA CCATTTTCTT
2201 GGCAGTCAGG TCGCCCTTCA CCTCCACCAT GAAATGCAGC GAGGAGAAGC GACGCCGCAA CTTCTCACAG TCGATGTTGG AGCCAGTGCG GGTGCGGAGC
2301 CCGGACTCAC GGCAGAAGTT CACATTGTTG ATAATGAGGC AGTGGCCACA GGGCTCCATG CTCAGGATGT AAGCCAAATC TGCATTTCCC CTCAAACTCT
2401 CAAGAGCACC GACATCACCA AATCCTCCAG AACCAATGTC CACTGGTCTG GGTGTTTCCG GTCTGAGAAC CTCTGGTTTG CGAATCTCTG GTCTGAGCAC
2501 CACTGGGGTA AGGTTTTCTA GGGTTGGCTT CGACAACTTT GCTGCTTGCC TGTTAGTTCG CAGAAACGAA GCCAGCATGT CCTGGCCTGT GTCCTCTAAG
2601 CAGGAGATGA ACAAAGGAAG AGCCTGACTC CCTCGAGTCT CCAGATCTAT GATCAGCTGC CTGGCCTGAT CCCGCCGAGA TCCAGAGCCT GCCCGCTGGA
2701 TGTCCTCGAT CATATGGGGC CTGAACAGCT CGCGGCTCAG CAGGGCGTCC CAGAGCTGGT CCACCTGCAG CTCTTCCACC AGCCGCAGCC GGCACCGCCG
2801 CAGGAGCCGC CGATCCGCTT CGTCCATCCT GTGTTCTGGC GGCAAACCCG TTGCGAAAAA GAACGTTCAC GGCGACTACT GCACTTATAT ACGGTTCTCC
2901 CCCACCCTCG GGAAAAAGGC GGAGCCAGTA CACGACATCA CTTTCCCAGT TTACCCCGCG CCACCTTCTC TAGGCACCGG ATCAATTGCC GACCCCTCCC
3001 CCCAACTTCT CGGGGACTGT GGGCGATGTG CGCTCTGCCC ACTGACGGGC ACCGGAGCCT GTTCATGTCC TACTGTTCAA GCCTCCAAGC TGTGCCTTGG
3101 GTGGCTTTGG GGCATGGACA TAAACCCAGC TTTCTTGTAC AAAGTGGGAA TTCCGATAAT CAACCTCTGG ATTACAAAAT TTGTGAAAGA TTGACTGGTA
3201 TTCTTAACTA TGTTGCTCCT TTTACGCTAT GTGGATACGC TGCTTTAATG CCTTTGTATC ATGCTATTGC TTCCCGTATG GCTTTCATTT TCTCCTCCTT
3301 GTATAAATCC TGGTTGCTGT CTCTTTATGA GGAGTTGTGG CCCGTTGTCA GGCAACGTGG CGTGGTGTGC ACTGTGTTTG CTGACGCAAC CCCCACTGGT
3401 TGGGGCATTG CCACCACCTG TCAGCTCCTT TCCGGGACTT TCGCTTTCCC CCTCCCTATT GCCACGGCGG AACTCATCGC CGCCTGCCTT GCCCGCTGCT
3501
```

FIGURE 7 - continued

```
3601 GGACAGGGGC TCGGCTGTTG GGCACTGACA ATTCCGTGGT GTTGTCGGGG AAGCTGACGT CCTTTCCATG GCTGCTCGCC TGTGTTGCCA CCTGGATTCT
3701 GCGCGGGACG TCCTTCTGCT ACGTCCCTTC GGCCCTCAAT CCAGCGGACC TTCCTTCCCG CGGCCTGCTG CCGGCTCTGC GGCCTCTTCC GCGTCTTCGC
3801 CTTCGCCCTC AGACGAGTCG GATCTCCCTT TGGGCCGCCT CCCCGCATCG GGAATTCCTA GAGCTCGCTG ATCAGCCTCG ACTGTGCCTT CTAGTTGCCA
3901 GCCATCTGTT GTTTGCCCCT CCCCCGTGCC TTCCTTGACC CTGGAAGGTG CCACTCCCAC TGTCCTTTCC TAATAAAATG AGGAAATTGC ATCGCATTGT
4001 CTGAGTAGGT GTCATTCTAT TCTGGGGGGT GGGGTGGGGC AGGACAGCAA GGGGGAGGAT TGGGAAGAGA ATAGCAGGCA TGCTGGGGAG GGCCGCAGGA
4101 ACCCCTAGTG ATGGAGTTGG CCACTCCCTC TCTGCGCGCT CGCTCGCTCA CTGAGGCCGG GCGACCAAAG GTCGCCCGAC GCCCGGGCTT TGCCCGGGCG
4201 GCCTCAGTGA GCGAGCGAGC GCGCAGCTGC CTGCAGGGGC GCCTGATGCG GTATTTTCTC CTTACGCATC TGTGCGGTAT TTCACACCGC ATACGTCAAA
4301 GCAACCATAG TACGCGCCCT GTAGCGGCGC ATTAAGCGCG GCGGGGGTGG TGGTTACGCG CAGCGTGACC GCTACACTTG CCAGCGCCTT AGCGCCCGCT
4401 CCTTTCGCTT TCTTCCCTTC CTTTCTCGCC ACGTTCGCCG GCTTTCCCCG TCAAGCTCTA AATCGGGGGC TCCCTTTAGG GTTCCGATTT AGTGCTTTAC
4501 GGCACCTCGA CCCCAAAAAA CTTGATTTGG GTGATGGTTC ACGTAGTGGG CCATCGCCCT GATAGACGGT TTTTCGCCCT TTGACGTTGG AGTCCACGTT
4601 CTTTAATAGT GGACTCTTGT TCCAAACTGG AACAACACTC AACTCTATCT CGGGCTATTC TTTTGATTTA TAAGGGATTT TGCCGATTTC GGTCTATTGG
4701 TTAAAAAATG AGCTGATTTA ACAAAAATTT AACGCGAATT TTAACAAAAT ATTAACGTTT ACAATTTTAT GGTGCACTCT CAGTACAATC TGCTCTGATG
4801 CCGCATAGTT AAGCCAGCCC CGACACCCGC CAACACCCGC TGACGCGCCC TGACGGGCTT GTCTGCTCCC GGCATCCGCT TACAGACAAG CTGTGACCGT
4901 CTCCGGGAGC TGCATGTGTC AGAGGTTTTC ACCGTCATCA CCGAAACGCG CGAGACGAAA GGGCCTCGTG ATACGCCTAT TTTTATAGGT TAATGTCATG
5001 ATAATAATGG TTTCTTAGAC GTCAGGTGGC ACTTTTCGGG GAAATGTGCG CGGAACCCCT ATTTGTTTAT TTTTCTAAAT ACATTCAAAT ATGTATCCGC
5101 TCATGAGACA ATAACCCTGA TAAATGCTTC AATAATATTG AAAAAGGAAG AGTATGAGTA TTCAACATTT CCGTGTCGCC CTTATTCCCT TTTTTGCGGC
5201 ATTTTGCCTT CCTGTTTTTG CTCACCCAGA AACGCTGGTG AAAGTAAAAG ATGCTGAAGA TCAGTTGGGT GCACGAGTGG GTTACATCGA ACTGGATCTC
5301 AACAGCGGTA AGATCCTTGA GAGTTTTCGC CCCGAAGAAC GTTTTCCAAT GATGAGCACT TTTAAAGTTC TGCTATGTGG CGCGGTATTA TCCCGTATTG
5401 ACGCCGGGCA AGAGCAACTC GGTCGCCGCA TACACTATTC TCAGAATGAC TTGGTTGAGT ACTCACCAGT CACAGAAAAG CATCTTACGG ATGGCATGAC
5501 AGTAAGAGAA TTATGCAGTG CTGCCATAAC CATGAGTGAT AACACTGCGG CCAACTTACT TCTGACAACG ATCGGAGGAC CGAAGGAGCT AACCGCTTTT
5601 TTGCACAACA TGGGGGATCA TGTAACTCGC CTTGATCGTT GGGAACCGGA GCTGAATGAA GCCATACCAA ACGACGAGCG TGACACCACG ATGCCTGTAG
5701 CAATGGCAAC AACGTTGCGC AAACTATTAA CTGGCGAACT ACTTACTCTA GCTTCCCGGC AACAATTAAT AGACTGGATG GAGGCGGATA AAGTTGCAGG
5801 ACCACTTCTG CGCTCGGCCC TTCCGGCTGG CTGGTTTATT GCTGATAAAT CTGGAGCCGG TGAGCGTGGA AGCCGCGGTA TCATTGCAGC ACTGGGGCCA
5901 GATGGTAAGC CCTCCCGTAT CGTAGTTATC TACACGACGG GGAGTCAGGC AACTATGGAT GAACGAAATA GACAGATCGC TGAGATAGGT GCCTCACTGA
6001 TTAAGCATTG GTAACTGTCA GACCAAGTTT ACTCATATAT ACTTTAGATT GATTTAAAAC TTCATTTTTA ATTTAAAAGG ATCTAGGTGA AGATCCTTTT
6101 TGATAATCTC ATGACCAAAA TCCCTTAACG TGAGTTTTCG TTCCACTGAG CGTCAGACCC CGTAGAAAAG ATCAAAGGAT CTTCTTGAGA TCCTTTTTTT
6201 CTGCGCGTAA TCTGCTGCTT GCAAACAAAA AAACCACCGC TACCAGCGGT GGTTTGTTTG CCGGATCAAG AGCTACCAAC TCTTTTTCCG AAGGTAACTG
6301 GCTTCAGCAG AGCGCAGATA CCAAATACTG TTCTTCTAGT GTAGCCGTAG TTAGGCCACC ACTTCAAGAA CTCTGTAGCA CCGCCTACAT ACCTCGCTCT
6401 GCTAATCCTG TTACCAGTGG CTGCTGCCAG TGGCGATAAG TCGTGTCTTA CCGGGTTGGA CTCAAGACGA TAGTTACCGG ATAAGGCGCA GCGGTCGGGC
6501 TGAACGGGGG GTTCGTGCAC ACAGCCCAGC TTGGAGCGAA CGACCTACAC CGAACTGAGA TACCTACAGC GTGAGCTATG AGAAAGCGCC ACGCTTCCCG
6601 AAGGGAGAAA GGCGGACAGG TATCCGGTAA GCGGCAGGGT CGGAACAGGA GAGCGCACGA GGGAGCTTCC AGGGGGAAAC GCCTGGTATC TTTATAGTCC
6701 TGTCGGGTTT CGCCACCTCT GACTTGAGCG TCGATTTTTG TGATGCTCGT CAGGGGGGCG GAGCCTATGG AAAAACGCCA GCAACGCGGC CTTTTTACGG
     TTCCTGGCCT TTTGCTGGCC TTTTGCTCAC ATGT
```

Validation by Restriction Enzyme Digestion

| Restriction Enzymes | Cutting Sites | DNA Fragments (bp) |
|---|---|---|
| NcoI | 1945, 3567 | 1622, 5112 |
| ApaLI | 3368, 4673, 5170, 6416 | 1305, 497, 1246, 3686 |
| EcoRI | 3149, 3753 | 604, 6130 |
| ApaLI+NcoI | 1945, 3368, 3567, 4673, 5170, 6416 | 1423, 199, 1106, 497, 1246, 2263 |
| ApaLI+EcoRI | 3149, 3368, 3753, 4673, 5170, 6416 | 219, 385, 920, 497, 1246, 3467 |

FIGURE 8

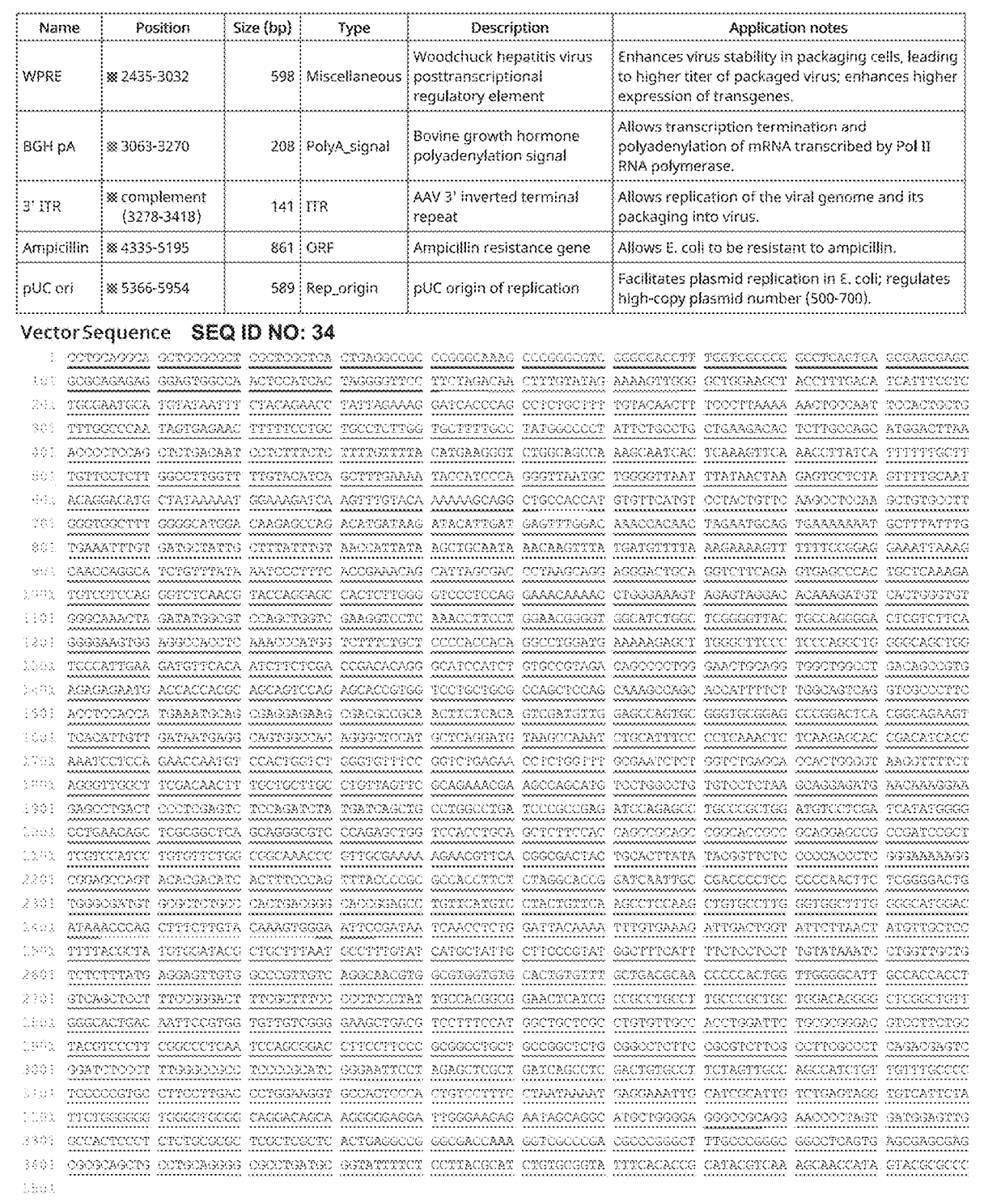

| Name | Position | Size (bp) | Type | Description | Application notes |
|---|---|---|---|---|---|
| WPRE | ※ 2435-3032 | 598 | Miscellaneous | Woodchuck hepatitis virus posttranscriptional regulatory element | Enhances virus stability in packaging cells, leading to higher titer of packaged virus; enhances higher expression of transgenes. |
| BGH pA | ※ 3063-3270 | 208 | PolyA_signal | Bovine growth hormone polyadenylation signal | Allows transcription termination and polyadenylation of mRNA transcribed by Pol II RNA polymerase. |
| 3' ITR | ※ complement (3278-3418) | 141 | ITR | AAV 3' inverted terminal repeat | Allows replication of the viral genome and its packaging into virus. |
| Ampicillin | ※ 4335-5195 | 861 | ORF | Ampicillin resistance gene | Allows E. coli to be resistant to ampicillin. |
| pUC ori | ※ 5366-5954 | 589 | Rep_origin | pUC origin of replication | Facilitates plasmid replication in E. coli; regulates high-copy plasmid number (500-700). |

Vector Sequence SEQ ID NO: 34

1 CCTGCAGGCA GCTGCGCGCT CGCTCGCTCA CTGAGGCCGC CCGGGCAAAG CCCGGGCGTC GGGCGACCTT TGGTCGCCCG GCCTCAGTGA GCGAGCGAGC
101 GCGCAGAGAG GGAGTGGCCA ACTCCATCAC TAGGGGTTCC TTCTAGACAA CTTTGTATAG AAAAGTTGGG GCTGGAAGCT ACCTTTGACA TCATTTCCTC
201 TGCGAATGCA TGTATAATTT CTACAGAACC TATTAGAAAG GATCACCCAG CCTCTGCTTT TGTACAACTT TCCCTTAAAA AACTGCCAAT TCCACTGCTG
301 TTTGGCCCAA TAGTGAGAAC TTTTTCCTGC TGCCTCTTGG TGCTTTTGCC TATGGCCCCT ATTCTGCCTG CTGAAGACAC TCTTGCCAGC ATGGACTTAA
401 ACCCCTCCAG CTCTGACAAT CCTCTTTCTC TTTTGTTTTA CATGAAGGGT CTGGCAGCCA AAGCAATCAC TCAAAGTTCA AACCTTATCA TTTTTTGCTT
501 TGTTCCTCTT GGCCTTGGTT TTGTACATCA GCTTTGAAAA TACCATCCCA GGGTTAATGC TGGGGTTAAT TTATAACTAA GAGTGCTCTA GTTTTGCAAT
601 ACAGGACATG CTATAAAAAT GGAAAGATCA AGTTTGTACA AAAAAGCAGG CTGCCACCAT GTGTTCATGT CCTACTGTTC AAGCCTCCAA GCTGTGCCTT
701 GGGTGGCTTT GGGGCATGGA CAAGAGCCAG ACATGATAAG ATACATTGAT GAGTTTGGAC AAACCACAAC TAGAATGCAG TGAAAAAAAT GCTTTATTTG
801 TGAAATTTGT GATGCTATTG CTTTATTTGT AACCATTATA AGCTGCAATA AACAAGTTTA TGATGTTTTA AAGAAAAGTT TTTTCCGGAG GAAATTAAAG
901 CAACCAGGCA TCTGTTTATA AATCCCTTTC ACCGAAACAG CATTAGCGAC CCTAAGCAGG AGGGACTGCA GGTCTTCAGA GTGAGCCCAC TGCTCAAAGA
1001 TGTCGTCCAG GGTCTCAACG TACCAGGAGC CACTCTTGGG GTCCCTCCAG GAAACAAAAC CTGGGAAAGT AGAGTAGGAC ACAAAGATGT CACTGGGTGT
1101 GGGCAAACTA GATATGGCGT CCAGCTGGTC GAAGGTCCTC AAACCTTCCT GGAACGGGGT GGCATCTGGC TCGGGGTTAC TGCCAGGGGA CTCGTCTTCA
1201 GGGGAAGTGG AGGCCACCTC AAACCCATGG TCTTTCTGCT CCCCACCACA GGCCTGGATG AAAAAGAGCT TGGGCTTCCC TCCCAGGCTG GGCCAGCTGG
1301 TCCCATTGAA GATGTTCACA ATCTTCTCGA CCGACACAGG GCATCCATCT GTGCCGTAGA CAGCCCCTGG GAACTGCAGG TGGCTGGCCT GACAGCCGTG
1401 AGAGAGAATG ACCACCACGC AGCAGTCCAG AGCACCGTGG TCCTGCTGCG CCAGCTCCAG CAAAGCCAGC ACCATTTTCT TGGCAGTCAG GTCGCCCTTC
1501 ACCTCCACCA TGAAATGCAG CGAGGAGAAG CGACGCCGCA ACTTCTCACA GTCGATGTTG GAGCCAGTGC GGGTGCGGAG CCCGGACTCA CGGCAGAAGT
1601 TCACATTGTT GATAATGAGG CAGTGGCCAC AGGGCTCCAT GCTCAGGATG TAAGCCAAAT CTGCATTTCC CCTCAAACTC TCAAGAGCAC CGACATCACC
1701 AAATCCTCCA GAACCAATGT CCACTGGTCT GGGTGTTTCC GGTCTGAGAA CCTCTGGTTT GCGAATCTCT GGTCTGAGCA CCACTGGGGT AAGGTTTTCT
1801 AGGGTTGGCT TCGACAACTT TGCTGCTTGC CTGTTAGTTC GCAGAAACGA AGCCAGCATG TCCTGGCCTG TGTCCTCTAA GCAGGAGATG AACAAAGGAA
1901 GAGCCTGACT CCCTCGAGTC TCCAGATCTA TGATCAGCTG CCTGGCCTGA TCCCGCCGAG ATCCAGAGCC TGCCCGCTGG ATGTCCTCGA TCATATGGGG
2001 CCTGAACAGC TCGCGGCTCA GCAGGGCGTC CCAGAGCTGG TCCACCTGCA GCTCTTCCAC CAGCCGCAGC CGGCACCGCC GCAGGAGCCG CCGATCCGCT
2101 TCGTCCATCC TGTGTTCTGG CGGCAAACCC GTTGCGAAAA AGAACGTTCA CGGCGACTAC TGCACTTATA TACGGTTCTC CCCCACCCTC GGGAAAAAGG
2201 CGGAGCCAGT ACACGACATC ACTTTCCCAG TTTACCCCGC GCCACCTTCT CTAGGCACCG GATCAATTGC CGACCCCTCC CCCCAACTTC TCGGGGACTG
2301 TGGGCGATGT GCGCTCTGCC CACTGACGGG CACCGGAGCC TGTTCATGTC CTACTGTTCA AGCCTCCAAG CTGTGCCTTG GGTGGCTTTG GGGCATGGAC
2401 ATAAACCCAG CTTTCTTGTA CAAAGTGGGA ATTCCGATAA TCAACCTCTG GATTACAAAA TTTGTGAAAG ATTGACTGGT ATTCTTAACT ATGTTGCTCC
2501 TTTTACGCTA TGTGGATACG CTGCTTTAAT GCCTTTGTAT CATGCTATTG CTTCCCGTAT GGCTTTCATT TTCTCCTCCT TGTATAAATC CTGGTTGCTG
2601 TCTCTTTATG AGGAGTTGTG GCCCGTTGTC AGGCAACGTG GCGTGGTGTG CACTGTGTTT GCTGACGCAA CCCCCACTGG TTGGGGCATT GCCACCACCT
2701 GTCAGCTCCT TTCCGGGACT TTCGCTTTCC CCCTCCCTAT TGCCACGGCG GAACTCATCG CCGCCTGCCT TGCCCGCTGC TGGACAGGGG CTCGGCTGTT
2801 GGGCACTGAC AATTCCGTGG TGTTGTCGGG GAAGCTGACG TCCTTTCCAT GGCTGCTCGC CTGTGTTGCC ACCTGGATTC TGCGCGGGAC GTCCTTCTGC
2901 TACGTCCCTT CGGCCCTCAA TCCAGCGGAC CTTCCTTCCC GCGGCCTGCT GCCGGCTCTG CGGCCTCTTC CGCGTCTTCG CCTTCGCCCT CAGACGAGTC
3001 GGATCTCCCT TTGGGCCGCC TCCCCGCATC GGGAATTCCT AGAGCTCGCT GATCAGCCTC GACTGTGCCT TCTAGTTGCC AGCCATCTGT TGTTTGCCCC
3101 TCCCCCGTGC CTTCCTTGAC CCTGGAAGGT GCCACTCCCA CTGTCCTTTC CTAATAAAAT GAGGAAATTG CATCGCATTG TCTGAGTAGG TGTCATTCTA
3201 TTCTGGGGGG TGGGGTGGGG CAGGACAGCA AGGGGGAGGA TTGGGAAGAG AATAGCAGGC ATGCTGGGGA GGGCCGCAGG AACCCCTAGT GATGGAGTTG
3301 GCCACTCCCT CTCTGCGCGC TCGCTCGCTC ACTGAGGCCG GGCGACCAAA GGTCGCCCGA CGCCCGGGCT TTGCCCGGGC GGCCTCAGTG AGCGAGCGAG
3401 CGCGCAGCTG CCTGCAGGGG CGCCTGATGC GGTATTTTCT CCTTACGCAT CTGTGCGGTA TTTCACACCG CATACGTCAA AGCAACCATA GTACGCGCCC
3501

FIGURE 8 - continued

```
TGTAGCGGCG CATTAAGCGC GGCGGGGGTG GTGGTTACGC GCAGCGTGAC CGCTACACTT GCCAGCGCCT TAGCGCCCGC TCCTTTCGCT TTCTTCCCTT
CCTTTCTCGC CACGTTCGCC GGCTTTCCCC GTCAAGCTCT AAATCGGGGG CTCCCTTTAG GGTTCCGATT TAGTGCTTTA CGGCACCTCG ACCCCAAAAA
ACTTGATTTG GGTGATGGTT CACGTAGTGG GCCATCGCCC TGATAGACGG TTTTTCGCCC TTTGACGTTG GAGTCCACGT TCTTTAATAG TGGACTCTTG
TTCCAAACTG GAACAACACT CAACTCTATC TCGGGCTATT CTTTTGATTT ATAAGGGATT TTGCCGATTT CGGTCTATTG GTTAAAAAAT GAGCTGATTT
AACAAAAATT TAACGCGAAT TTTAACAAAA TATTAACGTT TACAATTTTA TGGTGCACTC TCAGTACAAT CTGCTCTGAT GCCGCATAGT TAAGCCAGCC
CCGACACCCG CCAACACCCG CTGACGCGCC CTGACGGGCT TGTCTGCTCC CGGCATCCGC TTACAGACAA GCTGTGACCG TCTCCGGGAG CTGCATGTGT
CAGAGGTTTT CACCGTCATC ACCGAAACGC GCGAGACGAA AGGGCCTCGT GATACGCCTA TTTTTATAGG TTAATGTCAT GATAATAATG GTTTCTTAGA
CGTCAGGTGG CACTTTTCGG GGAAATGTGC GCGGAACCCC TATTTGTTTA TTTTTCTAAA TACATTCAAA TATGTATCCG CTCATGAGAC AATAACCCTG
ATAAATGCTT CAATAATATT GAAAAAGGAA GAGTATGAGT ATTCAACATT TCCGTGTCGC CCTTATTCCC TTTTTTGCGG CATTTTGCCT TCCTGTTTTT
GCTCACCCAG AAACGCTGGT GAAAGTAAAA GATGCTGAAG ATCAGTTGGG TGCACGAGTG GGTTACATCG AACTGGATCT CAACAGCGGT AAGATCCTTG
AGAGTTTTCG CCCCGAAGAA CGTTTTCCAA TGATGAGCAC TTTTAAAGTT CTGCTATGTG GCGCGGTATT ATCCCGTATT GACGCCGGGC AAGAGCAACT
CGGTCGCCGC ATACACTATT CTCAGAATGA CTTGGTTGAG TACTCACCAG TCACAGAAAA GCATCTTACG GATGGCATGA CAGTAAGAGA ATTATGCAGT
GCTGCCATAA CCATGAGTGA TAACACTGCG GCCAACTTAC TTCTGACAAC GATCGGAGGA CCGAAGGAGC TAACCGCTTT TTTGCACAAC ATGGGGGATC
ATGTAACTCG CCTTGATCGT TGGGAACCGG AGCTGAATGA AGCCATACCA AACGACGAGC GTGACACCAC GATGCCTGTA GCAATGGCAA CAACGTTGCG
CAAACTATTA ACTGGCGAAC TACTTACTCT AGCTTCCCGG CAACAATTAA TAGACTGGAT GGAGGCGGAT AAAGTTGCAG GACCACTTCT GCGCTCGGCC
CTTCCGGCTG GCTGGTTTAT TGCTGATAAA TCTGGAGCCG GTGAGCGTGG AAGCCGCGGT ATCATTGCAG CACTGGGGCC AGATGGTAAG CCCTCCCGTA
TCGTAGTTAT CTACACGACG GGGAGTCAGG CAACTATGGA TGAACGAAAT AGACAGATCG CTGAGATAGG TGCCTCACTG ATTAAGCATT GGTAACTGTC
AGACCAAGTT TACTCATATA TACTTTAGAT TGATTTAAAA CTTCATTTTT AATTTAAAAG GATCTAGGTG AAGATCCTTT TTGATAATCT CATGACCAAA
ATCCCTTAAC GTGAGTTTTC GTTCCACTGA GCGTCAGACC CCGTAGAAAA GATCAAAGGA TCTTCTTGAG ATCCTTTTTT TCTGCGCGTA ATCTGCTGCT
TGCAAACAAA AAAACCACCG CTACCAGCGG TGGTTTGTTT GCCGGATCAA GAGCTACCAA CTCTTTTTCC GAAGGTAACT GGCTTCAGCA GAGCGCAGAT
ACCAAATACT GTTCTTCTAG TGTAGCCGTA GTTAGGCCAC CACTTCAAGA ACTCTGTAGC ACCGCCTACA TACCTCGCTC TGCTAATCCT GTTACCAGTG
GCTGCTGCCA GTGGCGATAA GTCGTGTCTT ACCGGGTTGG ACTCAAGACG ATAGTTACCG GATAAGGCGC AGCGGTCGGG CTGAACGGGG GGTTCGTGCA
CACAGCCCAG CTTGGAGCGA ACGACCTACA CCGAACTGAG ATACCTACAG CGTGAGCTAT GAGAAAGCGC CACGCTTCCC GAAGGGAGAA AGGCGGACAG
GTATCCGGTA AGCGGCAGGG TCGGAACAGG AGAGCGCACG AGGGAGCTTC CAGGGGGAAA CGCCTGGTAT CTTTATAGTC CTGTCGGGTT TCGCCACCTC
TGACTTGAGC GTCGATTTTT GTGATGCTCG TCAGGGGGGC GGAGCCTATG GAAAAACGCC AGCAACGCGG CCTTTTTACG GTTCCTGGCC TTTTGCTGGC
CTTTTGCTCA CATGT
```

Validation by Restriction Enzyme Digestion

| Restriction Enzymes | Cutting Sites | DNA Fragments (bp) |
|---|---|---|
| XhoI | 1914 | 6015 |
| NdeI | 1994 | 6015 |
| XmnI | 322, 1313, 4523 | 991, 3210, 1814 |
| NcoI | 1226, 2848 | 1622, 4393 |
| ApaLI | 2649, 3954, 4451, 5697 | 1305, 497, 1246, 2967 |
| ApaLI+XhoI | 1914, 2649, 3954, 4451, 5697 | 735, 1305, 497, 1246, 2232 |
| ApaLI+NdeI | 1994, 2649, 3954, 4451, 5697 | 655, 1305, 497, 1246, 2312 |
| ApaLI+XmnI | 322, 1313, 2649, 3954, 4451, 4523, 5697 | 991, 1336, 1305, 497, 72, 1174, 640 |
| ApaLI+NcoI | 1226, 2649, 2848, 3954, 4451, 5697 | 1423, 199, 1106, 497, 1246, 1544 |

FIGURE 11A
FIGURE 11B
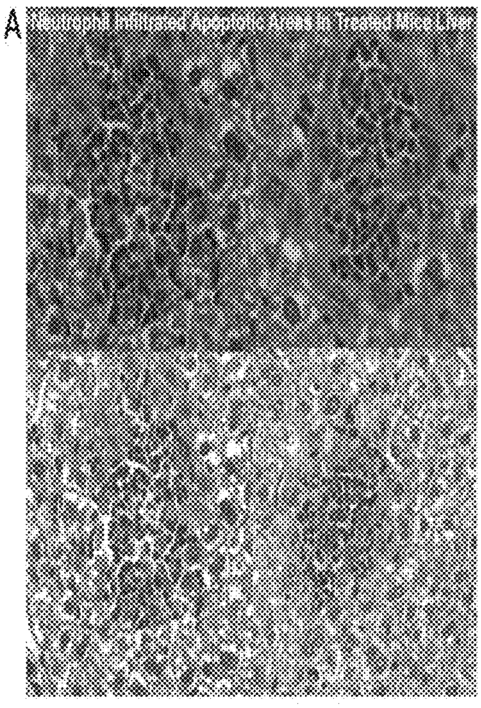
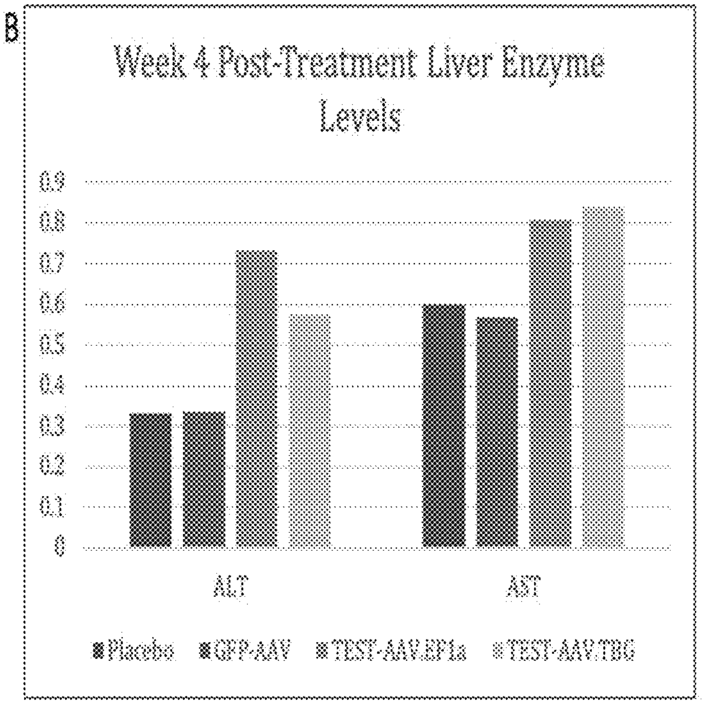

FIGURE 14

SEQ ID NO: 35

1 TAATACGACT CACTATAGGC ATGAAGACAG TGTTTAGCAA GATTGTTTTT TTGTCATTCT CCTAAGAAGC TATTAAAATC
81 ACATGGGGAT AGCACTACTA AAATTAATTT TACACATTAG GGCTCTTCCA TATAGGCAGC TCTCCCTAGC ATTGTTCACT
161 GTACACTCGA TCGTACTCCG CGTGGCCTCG GTGAAAATGT GGTGGCTCTT TCAAGTCCTC CCTAATGTTA CACACTGATT
241 AAAGATTGTT ACAATGAGCT ACCTACTGAT CGCCTGACAC GATTTCCTGC ACAGGCTTGA GCCATATACT CATACATCGC
321 ATCTTGGCCA CGTTTTCCAC GGGTTTCAAA ATTAATCTCA AGTTCTACGC TTAACGCTTT CGCCTGTTCC CAGTTATTAA
401 TATATTCAAC GCTAGAACTC CCCTCAGCGA AGGGAAGGCT GAGCACTACA CGCGAAGCAC CATCACCGAA CCTTTTGATA
481 AACTCTTCCG TTCCGACTTG CTCCATCAAC GGTTCAGTGA GACTTAAACC TAACTCTTTC TTAATAGTTT CGGCATTATC
561 CACTTTTAGT GCGAGAACCT TCGTCAGTCC TGGATACGTC ACTTTGACCA CGCCTCCAGC TTTTCCAGAG AGCGGGTTTT
641 CATTATCTAC AGAGTATCCC GCAGCGTCGT ATTTATTGTC GGTACTATAA AACCCTTTCC AATCATCGTC ATAATTTCCT
721 TGTGTACCAG ATTTTGGCTT TTGTATACCT TTTTGAATGG AATCTACATA ACCAGGTTTA GTCCCGTGGT ACGAAGAAAA
801 GTTTTCCATC ACAAAAGATT TAGAAGAATC AACAACATCA TCAGCGCCCA TCTTACCTTT CGGTCACACC CGGACGAAAC
881 CTAGATGTGC TGATGATCGG CTGCAACACG GACGAAACCG TAAGCAGCCT GCAGAAGATA GACGAGTTAC TCGTGTCCTG
961 TCAACGACAG TAATTAGTTA TTAATTATAC TGCGTGAGTG CACTAAGCAT GCAGCCGAGT GACAGCCACA CAGATTTTAA
1041 AGTTCGTTTA GAGAACAGAT CTACAAGAGA TCGAAAGTTG GTTGGTTTGT TACCTGGGAA GGTATAAACC TTTAATAAAA
1121 AAAAAAAAAA AAAAAAAAAA AAAAAATGAA GAGCCGTACG GGCGCGCCTA GGCGCGATTC CGCTTCCTCG CTCACTGACT
1201 CGCTGCGCTC GGTCGTTCGG CTGCGGCGAG CGGTATCAGC TCACTCAAAG GCGGTAATAC GGTTATCCAC AGAATCAGGG
1281 GATAACGCAG GAAAGAACAT GTGAGCAAAA GGCCAGCAAA AGGCCAGGAA CCGTAAAAAG GCCGCGTTGC TGGCGTTTTT
1361 CCATAGGCTC CGCCCCCCTG ACGAGCATCA CAAAAATCGA CGCTCAAGTC AGAGGTGGCG AAACCCGACA GGACTATAAA
1441 GATACCAGGC GTTTCCCCCT GGAAGCTCCC TCGTGCGCTC TCCTGTTCCG ACCCTGCCGC TTACCGGATA CCTGTCCGCC
1521 TTTCTCCCTT CGGGAAGCGT GGCGCTTTCT CATAGCTCAC GCTGTAGGTA TCTCAGTTCG GTGTAGGTCG TTCGCTCCAA
1601 GCTGGGCTGT GTGCACGAAC CCCCCGTTCA GCCCGACCGC TGCGCCTTAT CCGGTAACTA TCGTCTTGAG TCCAACCCGG
1681 TAAGACACGA CTTATCGCCA CTGGCAGCAG CCACTGGTAA CAGGATTAGC AGAGCGAGGT ATGTAGGCGG TGCTACAGAG
1761 TTCTTGAAGT GGTGGCCTAA CTACGGCTAC ACTAGAAGAA CAGTATTTGG TATCTGCGCT CTGCTGAAGC CAGTTACCTT
1841 CGGAAAAAGA GTTGGTAGCT CTTGATCCGG CAAACAAACC ACCGCTGGTA GCGGTGGTTT TTTTGTTTGC AAGCAGCAGA
1921 TTACGCGCAG AAAAAAAGGA TCTCAAGAAG ATCCTTTGAT CTTTTCTACG GGGTCTGACG CTCAGTGGAA CGAAAACTCA
2001 CGTTAAGGGA TTTTGGTCAT GAGATTATCA AAAAGGATCT TCACCTAGAT CCTTTTAAAT TAAAAATGAA GTTTTAAATC
2081 AATCTAAAGT ATATATGAGT AAACTTGGTC TGACAGTTAC CAATGCTTAA TCAGTGAGGC ACCTATCTCA GCGATCTGTC
2161 TATTTCGTTC ATCCATAGTT GCCTGACTCC CCGTCGTGTA GATAACTACG ATACGGGAGG GCTTACCATC TGGCCCCAGT
2241 GCTGCAATGA TACCGCGAGA TCCACGCTCA CCGGCTCCAG ATTTATCAGC AATAAACCAG CCAGCCGGAA GGGCCGAGCG
2321 CAGAAGTGGT CCTGCAACTT TATCCGCCTC CATCCAGTCT ATTAATTGTT GCCGGGAAGC TAGAGTAAGT AGTTCGCCAG
2401 TTAATAGTTT GCGCAACGTT GTTGCCATTG CTACAGGCAT CGTGGTGTCA CGCTCGTCGT TTGGTATGGC TTCATTCAGC
2481 TCCGGTTCCC AACGATCAAG GCGAGTTACA TGATCCCCCA TGTTGTGCAA AAAAGCGGTT AGCTCCTTCG GTCCTCCGAT
2561 CGTTGTCAGA AGTAAGTTGG CCGCAGTGTT ATCACTCATG GTTATGGCAG CACTGCATAA TTCTCTTACT GTCATGCCAT
2641 CCGTAAGATG CTTTTCTGTG ACTGGTGAGT ACTCAACCAA GTCATTCTGA GAATAGTGTA TGCGGCGACC GAGTTGCTCT
2721 TGCCCGGCGT CAATACGGGA TAATACCGCG CCACATAGCA GAACTTTAAA AGTGCTCATC ATTGGAAAAC GTTCTTCGGG
2801 GCGAAAACTC TCAAGGATCT TACCGCTGTT GAGATCCAGT TCGATGTAAC CCACTCGTGC ACCCAACTGA TCTTCAGCAT
2881 CTTTTACTTT CACCAGCGTT TCTGGGTGAG CAAAAACAGG AAGGCAAAAT GCCGCAAAAA AGGGAATAAG GGCGACACGG
2961 AAATGTTGAA TACTCATACT CTTCCTTTTT CAATATTATT GAAGCATTTA TCAGGGTTAT TGTCTCATGA GCGGATACAT
3041 ATTTGAATGT ATTTAGAAAA ATAAACAAAT AGGGGTTCCG CGCACATTTC CCCGAAAAGT GCCACCTGAC GTCTAAGAAA
3121 CCATTATTAT CATGACATTA ACCTATAAAA ATAGGCGTAT CACGAGGCCC TTTCGTC

FIGURE 15

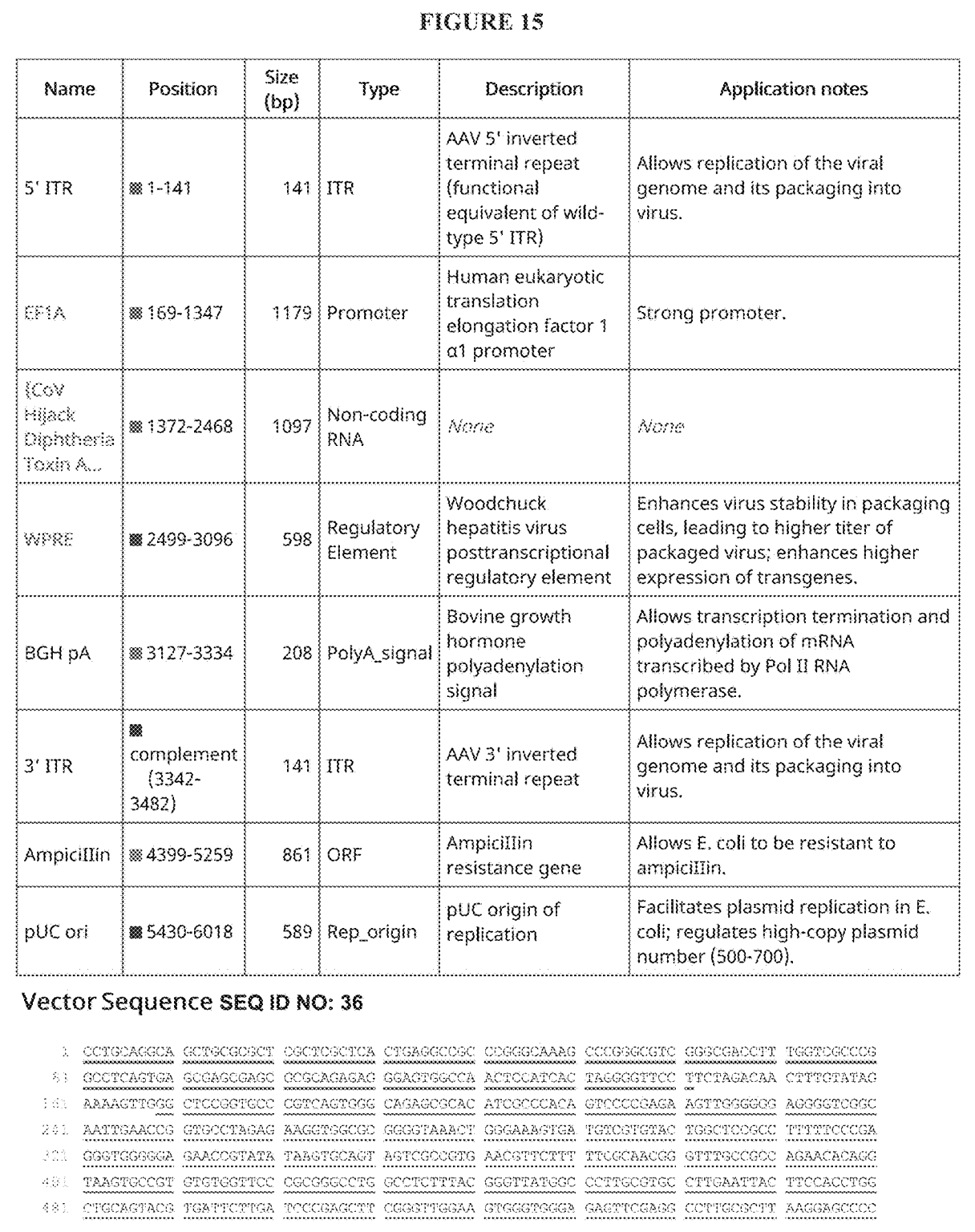

| Name | Position | Size (bp) | Type | Description | Application notes |
|---|---|---|---|---|---|
| 5' ITR | 1-141 | 141 | ITR | AAV 5' inverted terminal repeat (functional equivalent of wild-type 5' ITR) | Allows replication of the viral genome and its packaging into virus. |
| EF1A | 169-1347 | 1179 | Promoter | Human eukaryotic translation elongation factor 1 α1 promoter | Strong promoter. |
| (CoV Hijack Diphtheria Toxin A... | 1372-2468 | 1097 | Non-coding RNA | *None* | *None* |
| WPRE | 2499-3096 | 598 | Regulatory Element | Woodchuck hepatitis virus posttranscriptional regulatory element | Enhances virus stability in packaging cells, leading to higher titer of packaged virus; enhances higher expression of transgenes. |
| BGH pA | 3127-3334 | 208 | PolyA_signal | Bovine growth hormone polyadenylation signal | Allows transcription termination and polyadenylation of mRNA transcribed by Pol II RNA polymerase. |
| 3' ITR | complement (3342-3482) | 141 | ITR | AAV 3' inverted terminal repeat | Allows replication of the viral genome and its packaging into virus. |
| Ampicillin | 4399-5259 | 861 | ORF | Ampicillin resistance gene | Allows E. coli to be resistant to ampicillin. |
| pUC ori | 5430-6018 | 589 | Rep_origin | pUC origin of replication | Facilitates plasmid replication in E. coli; regulates high-copy plasmid number (500-700). |

Vector Sequence SEQ ID NO: 36

```
  1 CCTGCAGGCA GCTGCGCGCT CGCTCGCTCA CTGAGGCCGC CCGGGCAAAG CCCGGGCGTC GGGCGACCTT TGGTCGCCCG
 81 GCCTCAGTGA GCGAGCGAGC GCGCAGAGAG GGAGTGGCCA ACTCCATCAC TAGGGGTTCC TTCTAGACAA CTTTGTATAG
161 AAAAGTTGGG CTCCGGTGCC CGTCAGTGGG CAGAGCGCAC ATCGCCCACA GTCCCCGAGA AGTTGGGGGG AGGGGTCGGC
241 AATTGAACCG GTGCCTAGAG AAGGTGGCGC GGGGTAAACT GGGAAAGTGA TGTCGTGTAC TGGCTCCGCC TTTTTCCCGA
321 GGGTGGGGGA GAACCGTATA TAAGTGCAGT AGTCGCCGTG AACGTTCTTT TTCGCAACGG GTTTGCCGCC AGAACACAGG
401 TAAGTGCCGT GTGTGGTTCC CGCGGGCCTG GCCTCTTTAC GGGTTATGGC CCTTGCGTGC CTTGAATTAC TTCCACCTGG
481 CTGCAGTACG TGATTCTTGA TCCCGAGCTT CGGGTTGGAA GTGGGTGGGA GAGTTCGAGG CCTTGCGCTT AAGGAGCCCC
```

FIGURE 15 - continued

561 TTCGCCTCGT GCTTGAGTTG AGGCCTGGCC TGGGCGCTGG GGCCGCCGCG TGCGAATCTG GTGGCACCTT CGCGCCTGTC
641 TCGCTGCTTT CGATAAGTCT CTAGCCATTT AAAATTTTTG ATGACCTGCT GCGACGCTTT TTTTCTGGCA AGATAGTCTT
721 GTAAATGCGG GCCAAGATCT GCACACTGGT ATTTCGGTTT TTGGGGCCGC GGGCGGCGAC GGGGCCCGTG CGTCCCAGCG
801 CACATGTTCG GCGAGGCGGG GCCTGCGAGC GCGGCCACCG AGAATCGGAC GGGGGTAGTC TCAAGCTGGC CGGCCTGCTC
881 TGGTGCCTGG TCTCGCGCCG CCGTGTATCG CCCCGCCCTG GGCGGCAAGG CTGGCCCGGT CGGCACCAGT TGCGTGAGCG
961 GAAAGATGGC CGCTTCCCGG CCCTGCTGCA GGGAGCTCAA AATGGAGGAC GCGGCGCTCG GGAGAGCGGG CGGGTGAGTC
1041 ACCCACACAA AGGAAAAGGG CCTTTCCGTC CTCAGCCGTC GCTTCATGTG ACTCCACGGA GTACCGGGCG CCGTCCAGGC
1121 ACCTCGATTA GTTCTCGAGC TTTTGGAGTA CGTCGTCTTT AGGTTGGGGG GAGGGGTTTT ATGCGATGGA GTTTCCCCAC
1201 ACTGAGTGGG TGGAGACTGA AGTTAGGCCA GCTTGGCACT TGATGTAATT CTCCTTGGAA TTTGCCCTTT TTGAGTTTGG
1281 ATCTTGGTTC ATTCTCAAGC CTCAGACAGT GGTTCAAAGT TTTTTTCTTC CATTTCAGGT GTCGTGACAA GTTTGTACAA
1361 AAAAGCAGGC TCATGAAGAC AGTGTTTAGC AAGATTGTTT TTTTGTCATT CTCCTAAGAA GCTATTAAAA TCACATGGGG
1441 ATAGCACTAC TAAAATTAAT TTTACACATT AGGGCTCTTC CATATAGGCA GCTCTCCCTA GCATTGTTCA CTGTACACTC
1521 GATCGTACTC CGCGTGGCCT CGGTGAAAAT GTGGTGGCTC TTTCAAGTCC TCCCTAATGT TACACACTGA TTAAAGATTG
1601 TTACAATGAG CTACCTACTG ATCGCCTGAC ACGATTTCCT GCACAGGCTT GAGCCATATA CTCATACATC GCATCTTGGC
1681 CACGTTTTCC ACGGGTTTCA AAATTAATCT CAAGTTCTAC GCTTAACGCT TTCGCCTGTT CCCAGTTATT AATATATTCA
1761 ACGCTAGAAC TCCCCTCAGC GAAGGGAAGG CTGAGCACTA CACGCGAAGC ACCATCACCG AACCTTTTGA TAAACTCTTC
1841 CGTTCCGACT TGCTCCATCA ACGGTTCAGT GAGACTTAAA CCTAACTCTT TCTTAATAGT TTCGGCATTA TCCACTTTTA
1921 GTGCGAGAAC CTTCGTCAGT CCTGGATACG TCACTTTGAC CACGCCTCCA GCTTTTCCAG AGAGCGGGTT TTCATTATCT
2001 ACAGAGTATC CCGCAGCGTC GTATTTATTG TCGGTACTAT AAAACCCTTT CCAATCATCG TCATAATTTC CTTGTGTACC
2081 AGATTTTGGC TTTTGTATAC CTTTTTGAAT GGAATCTACA TAACCAGGTT TAGTCCCGTG GTACGAAGAA AAGTTTTCCA
2161 TCACAAAAGA TTTAGAAGAA TCAACAACAT CATCAGCGCC CATCTTACCT TTCGGTCACA CCCGGACGAA ACCTAGATGT
2241 GCTGATGATC GGCTGCAACA CGGACGAAAC CGTAAGCAGC CTGCAGAAGA TAGACGAGTT ACTCGTGTCC TGTCAACGAC
2321 AGTAATTAGT TATTAATTAT ACTGCGTGAG TGCACTAAGC ATGCAGCCGA GTGACAGCCA CACAGATTTT AAAGTTCGTT
2401 TAGAGAACAG ATCTACAAGA GATCGAAAGT TGGTTGGTTT GTTACCTGGG AAGGTATAAA CCTTTAATAC CCAGCTTTCT
2481 TGTACAAAGT GGGAATTCCG ATAATCAACC TCTGGATTAC AAAATTTGTG AAAGATTGAC TGGTATTCTT AACTATGTTG
2561 CTCCTTTTAC GCTATGTGGA TACGCTGCTT TAATGCCTTT GTATCATGCT ATTGCTTCCC GTATGGCTTT CATTTTCTCC
2641 TCCTTGTATA AATCCTGGTT GCTGTCTCTT TATGAGGAGT TGTGGCCCGT TGTCAGGCAA CGTGGCGTGG TGTGCACTGT
2721 GTTTGCTGAC GCAACCCCCA CTGGTTGGGG CATTGCCACC ACCTGTCAGC TCCTTTCCGG GACTTTCGCT TTCCCCCTCC
2801 CTATTGCCAC GGCGGAACTC ATCGCCGCCT GCCTTGCCCG CTGCTGGACA GGGGCTCGGC TGTTGGGCAC TGACAATTCC
2881 GTGGTGTTGT CGGGGAAGCT GACGTCCTTT CCATGGCTGC TCGCCTGTGT TGCCACCTGG ATTCTGCGCG GGACGTCCTT
2961 CTGCTACGTC CCTTCGGCCC TCAATCCAGC GGACCTTCCT TCCCGCGGCC TGCTGCCGGC TCTGCGGCCT CTTCCGCGTC
3041 TTCGCCTTCG CCCTCAGACG AGTCGGATCT CCCTTTGGGC CGCCTCCCCG CATCGGGAAT TCCTAGAGCT CGCTGATCAG
3121 CCTCGACTGT GCCTTCTAGT TGCCAGCCAT CTGTTGTTTG CCCCTCCCCC GTGCCTTCCT TGACCCTGGA AGGTGCCACT
3201 CCCACTGTCC TTTCCTAATA AAATGAGGAA ATTGCATCGC ATTGTCTGAG TAGGTGTCAT TCTATTCTGG GGGGTGGGGT
3281 GGGGCAGGAC AGCAAGGGGG AGGATTGGGA AGAGAATAGC AGGCATGCTG GGGAGGGCCG CAGGAACCCC TAGTGATGGA
3361 GTTGGCCACT CCCTCTCTGC GCGCTCGCTC GCTCACTGAG GCCGGGCGAC CAAAGGTCGC CCGACGCCCG GGCTTTGCCC
3441 GGGCGGCCTC AGTGAGCGAG CGAGCGCGCA GCTGCCTGCA GGGGCGCCTG ATGCGGTATT TTCTCCTTAC GCATCTGTGC
3521 GGTATTTCAC ACCGCATACG TCAAAGCAAC CATAGTACGC GCCCTGTAGC GGCGCATTAA GCGCGGCGGG GGTGGTGGTT
3601 ACGCGCAGCG TGACCGCTAC ACTTGCCAGC GCCTTAGCGC CCGCTCCTTT CGCTTTCTTC CCTTCCTTTC TCGCCACGTT
3681 CGCCGGCTTT CCCCGTCAAG CTCTAAATCG GGGGCTCCCT TTAGGGTTCC GATTTAGTGC TTTACGGCAC CTCGACCCCA
3761 AAAAACTTGA TTTGGGTGAT GGTTCACGTA GTGGGCCATC GCCCTGATAG ACGGTTTTTC GCCCTTTGAC GTTGGAGTCC
3841 ACGTTCTTTA ATAGTGGACT CTTGTTCCAA ACTGGAACAA CACTCAACTC TATCTCGGGC TATTCTTTTG ATTTATAAGG
3921 GATTTTGCCG ATTTCGGTCT ATTGGTTAAA AAATGAGCTG ATTTAACAAA AATTTAACGC GAATTTTAAC AAAATATTAA
4001 CGTTTACAAT TTTATGGTGC ACTCTCAGTA CAATCTGCTC TGATGCCGCA TAGTTAAGCC AGCCCCGACA CCCGCCAACA
4081 CCCGCTGACG CGCCCTGACG GGCTTGTCTG CTCCCGGCAT CCGCTTACAG ACAAGCTGTG ACCGTCTCCG GGAGCTGCAT
4161 GTGTCAGAGG TTTTCACCGT CATCACCGAA ACGCGCGAGA CGAAAGGGCC TCGTGATACG CCTATTTTTA TAGGTTAATG
4241 TCATGATAAT AATGGTTTCT TAGACGTCAG GTGGCACTTT TCGGGGAAAT GTGCGCGGAA CCCCTATTTG TTTATTTTTC
4321 TAAATACATT CAAATATGTA TCCGCTCATG AGACAATAAC CCTGATAAAT GCTTCAATAA TATTGAAAAA GGAAGAGTAT

COMPOSITIONS AND METHODS FOR TREATING VIRAL INFECTIONS

CROSS-REFERENCE TO RELATED APPLICATIONS

This application claims priority to U.S. Provisional Application No. 62/893,460, filed Aug. 29, 2019; U.S. Provisional Application No. 62/968,387, filed Jan. 31, 2020; U.S. Provisional Application No. 62/976,491, filed Feb. 14, 2020; and U.S. Provisional Application No. 62/985,597, filed Mar. 5, 2020, each of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Sep. 18, 2024, is named 12004_011626-US0_SL.txt and is 57,622 bytes in size.

FIELD

The disclosure provides methods and compositions utilizing recombinant nucleic acid constructs or a replication incompetent virus-like particle encoding a chemokine, cytokine, or apoptosis inducing protein (e.g. Caspase 9 (Casp9)), in a form which will only be transcribed in the presence of a viral polymerase. These methods can be adapted to target many viral infections and reduce or eliminate viral load, and provide a fundamentally different treatment for viral infections.

BACKGROUND

Viral infections are a challenging issue of global public health. Some progress has been made in treating certain viral infections, but many of these treatments are ineffective or cost-prohibitive for much of the world. For example, hepatitis B virus (HBV) infection, taken as a model for difficult to treat, chronic viral infections, remains a tremendous public health challenge. Since the introduction of HBV vaccination, the risk of transmission, including vertical mother-to-child transmission and horizontal transmission, has decreased dramatically. However, it is estimated that 248 million persons are still chronically infected by HBV worldwide. This imposes a high socioeconomic burden in the endemic regions and countries. The clinical outcomes of chronic hepatitis B (CHB) vary greatly, ranging from spontaneous resolution of hepatitis B to severe detrimental consequences, including the development of hepatic failure, cirrhosis, and hepatocellular carcinoma (HCC). Persistent or recurrent hepatic necroinflammation mediated by the host antiviral immunity is the major cause for the disease progression, eventually leading to advanced fibrosis and carcinogenesis of liver. The lifetime risk of severe adverse outcomes of CHB is as high as 15%-40%. Early diagnosis and timely antiviral treatment for those at risk are required to prevent the development of adverse clinical outcomes.

Thus, new, more effective and more widely available treatments are needed for treating viral infections, such as HBV. One of the challenging aspects in developing effective viral treatments are their complex life cycles, which are intimately connected to that of the host cell. For example HBV persistence in infected hepatocytes is due to the presence of covalently closed circular DNA (cccDNA), the template for the transcription of viral RNAs. Antiviral therapies with nucleoside analogues inhibit replication of HBV DNA in capsids present in the cytoplasm of infected cells, but do not reduce or destroy nuclear cccDNA. Despite some progress, antiviral drugs are currently only effective against a few viral diseases.

Thus, fundamentally different treatment approaches are needed to change the landscape for treating viral infections.

SUMMARY

Provided herein is a recombinant nucleic acid sequence comprising: a negative strand nucleic acid molecule or a pgRNA nucleic acid molecule encoding a chemokine, a cytokine, an apoptosis inducing protein, or a combination thereof, flanked by a first and second viral transcription recognition signal, and further comprising a first promoter upstream (5') of the first viral transcription recognition signal and a second promoter adjacent and 5' to the negative strand nucleic acid molecule or pgRNA nucleic acid molecule encoding a chemokine, a cytokine, a apoptosis inducing protein, or combination thereof.

In certain embodiments, the negative strand nucleic acid molecule is negative sense RNA, negative sense DNA, single or double strand DNA that expresses a non-coding, negative sense RNA, or pgRNA, or any combination thereof.

In additional embodiments, the viral transcription recognition signal is selected from a virus selected from a negative strand virus, an RNA reverse transcribing virus, or a DNA reverse transcribing virus.

In additional embodiments, the recombinant nucleic acid further comprises a poly A tail downstream (3') of the negative strand nucleic acid molecule or pgRNA nucleic acid molecule encoding a chemokine, a cytokine, an apoptosis inducing protein, or combination thereof.

In additional embodiments, the apoptosis inducing protein is selected from the group consisting of BAX, BID, BAK, BAD, caspase 2, caspase 8, caspase 9, caspase 10, caspase 11, caspase 12, cytochrome C, SMAC, and apoptosis-inducing factor, or combinations thereof.

In yet additional embodiments, the first promoter comprises a strong ubiquitous promoter or a liver-tissue-specific promoter, selected from the group consisting of TBG (Thyroxine Binding Globulin), albumin promoter and/or enhancing element, AFP (alpha-fetoprotein) promoter, AAT (Alpha-1-antitrypsin) promoter, ApoE (Apolipoprotein E) promoter or PEPCK (Phosphoenolpyruvate carboxykinase) promoter.

In yet additional embodiments, the second promoter comprises elongation factor 1alpha binding sequence (EFS).

In additional embodiments, the chemokine is selected from CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL8, CXCL9, CXCL10, CXCL11, CXCL12, CXCL13, CXCL14, CXCL15, CXCL16, CXCL17, XCL1, XCL2, and CX3CL1.

In further embodiments, the cytokine is selected from the group consisting of IL-15, IL-2, IL-8, IL-10, IL-12, IL-6, IFN-α, IFN-β, IFN-γ, TNF-α, CD40L, Mig, and Crg-2.

In additional embodiments, the viral transcription recognition signal comprises epsilon recognition signal (SEQ ID NO: 1).

In additional embodiments, the virus is Hepatitis B virus, Hepatitis D virus, ebola virus, Marburg virus, human parainfluenza virus 1, measles virus, mumps virus, human respiratory syncytial virus, vesicular stomatitis Indiana virus, rabies virus, bovine ephemeral fever virus, lymphocytic choriomeningitis virus, Bunyamwera virus, Hantaan virus, Nairobi sheep disease virus, sandfly fever Sicilian virus, influenza virus A, influenza virus C, Thogoto virus, mouse mammary tumor virus, murine leukemia virus, avian leukosis virus, Mason-Pfizer monkey virus, bovine leukemia virus, human immunodeficiency virus 1, human spumavirus, duck hepatitis B virus, and a combination thereof.

In additional embodiments, the nucleic acid molecule does not comprise sequences (coding or noncoding) for viral polymerase, reverse transcriptase, capsid, envelope, a packaging signal, or a translocation motif.

Provided herein is a vector comprising any of the recombinant nucleic acid sequences described herein.

In additional embodiments, the vector comprises a delivery vector or vehicle for delivery to a mammalian cell.

In additional embodiments, the vector or vehicle comprises a VLP, an adeno-associated virus (AAV), a liposome, a nanoparticle, a micelle, a polymeric vesicle, or a polymersome.

Provided herein is a pharmaceutical composition comprising any of the recombinant nucleic acid sequences described herein or any of the vectors described herein.

Provided herein is a replication incompetent virus-like particle (VLP) comprising:

- an optional translocation motif (TLM) fused to a capsid protein from a hepatitis B viral capsid or a hepatitis D viral capsid; and
- a negative strand nucleic acid molecule or a pgRNA nucleic acid molecule encoding a chemokine, a cytokine, a apoptosis inducing protein, or a combination thereof, flanked by a first and second viral transcription recognition signal, and further comprising a first promoter upstream (5') of the first viral transcription recognition signal and a second promoter adjacent and 5' to the negative strand nucleic acid molecule or pgRNA nucleic acid molecule encoding a chemokine, a cytokine, a apoptosis inducing protein, or a combination thereof.

Further provided herein is a replication incompetent virus-like particle (VLP) comprising:

- a negative strand nucleic acid molecule or a pgRNA nucleic acid molecule encoding a chemokine, a cytokine, a apoptosis inducing protein, or a combination thereof, flanked by a first and second target viral transcription recognition signal, and further comprising a first promoter upstream (5') of the first viral transcription recognition signal and a second promoter adjacent and 5' to the negative strand nucleic acid molecule or pgRNA nucleic acid molecule encoding a chemokine, a cytokine, a apoptosis inducing protein, or a combination thereof, wherein the VLP exhibits tropism for the target virally infected cells.

In additional embodiments, the negative strand nucleic acid molecule is negative sense RNA, negative sense DNA, single or double strand DNA that expresses a non-coding, negative sense RNA, or pgRNA, or any combination thereof.

In additional embodiments, the replication incompetent virus-like particle (VLP) further comprises a poly A tail downstream (3') of the negative strand nucleic acid molecule or pgRNA nucleic acid molecule encoding a chemokine, a cytokine, a apoptosis inducing protein, or combination thereof.

In additional embodiments, the first promoter comprises a strong ubiquitous promoter or a liver-tissue-specific promoter selected from the group consisting of TBG (Thyroxine Binding Globulin), albumin promoter and/or enhancing element, AFP (alpha-fetoprotein) promoter, AAT (Alpha-1-antitrypsin) promoter, ApoE (Apolipoprotein E) promoter or PEPCK (Phosphoenolpyruvate carboxykinase) promoter.

In additional embodiments, the second promoter comprises elongation factor 1alpha binding sequence (EFS).

In additional embodiments, the viral transcription recognition signal is selected from a virus selected from a negative strand virus, an RNA reverse transcribing virus, or a DNA reverse transcribing virus.

In additional embodiments, the viral transcription recognition signal comprises the epsilon recognition signal (SEQ ID NO: 1).

In additional embodiments, the apoptosis inducing protein is selected from the group consisting of BAX, BID, BAK, BAD, caspase 2, caspase 8, caspase 9, caspase 10, caspase 11, caspase 12, cytochrome C, SMAC, and apoptosis-inducing factor.

In additional embodiments, the chemokine is selected from CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL8, CXCL9, CXCL10, CXCL11, CXCL12, CXCL13, CXCL14, CXCL15, CXCL16, CXCL17, XCL1, XCL2, and CX3CL1.

In additional embodiments, the cytokine is selected from the group consisting of IL-15, IL-2, IL-8, IL-10, IL-12, IL-6, IFN-α, IFN-β, IFN-γ, TNF-α, CD40L, Mig, and Crg-2.

In additional embodiments, the virus is Hepatitis B virus, Hepatitis D virus, ebola virus, Marburg virus, human parainfluenza virus 1, measles virus, mumps virus, human respiratory syncytial virus, vesicular stomatitis Indiana virus, rabies virus, bovine ephemeral fever virus, lymphocytic choriomeningitis virus, Bunyamwera virus, Hantaan virus, Nairobi sheep disease virus, sandfly fever Sicilian virus, influenza virus A, influenza virus C, Thogoto virus, mouse mammary tumor virus, murine leukernia virus, avian leukosis virus, Mason-Pfizer monkey virus, bovine leukemia virus, human immunodeficiency virus 1, human spumavirus, duck hepatitis B virus, and a combination thereof.

In additional embodiments, the nucleic acid molecule does not comprise sequences (coding or noncoding) for viral capsid, polymerase, reverse transcriptase, envelope, packaging signal, or translocation motifs.

Further provided is a pharmaceutical composition comprising any of the incompetent virus-like particles described herein.

Further provided is a method of treating a viral infection in a subject in need thereof, the method comprising administering to the subject a recombinant nucleic acid molecule described herein, or the vector described herein, or pharmaceutical compositions described herein, or the replication incompetent virus-like particle described herein.

In additional embodiments, the viral infection comprises an infection from a virus classified under Baltimore Classification IV, V, VI, or VII.

In additional embodiments, the viral infection comprises an infection from a virus selected from the group consisting of Hepatitis B virus, Hepatitis D virus, ebola virus, Marburg virus, human parainfluenza virus 1, measles virus, mumps virus, human respiratory syncytial virus, vesicular stomatitis Indiana virus, rabies virus, bovine ephemeral fever virus, lymphocytic choriomeningitis virus, Bunyamwera virus, Hantaan virus, Nairobi sheep disease virus, sandfly fever Sicilian virus, influenza virus A, influenza virus C, Thogoto virus, mouse mammary tumor virus, murine leukernia virus, avian leukosis virus, Mason-Pfizer monkey virus, bovine leukemia virus, human immunodeficiency virus 1, human spumavirus, duck hepatitis B virus, and a combination thereof.

In additional embodiments, the viral infection comprises an infection from a virus selected from the group consisting of influenza A, B, C, and/or any coronavirus, and/or any viruses from Baltimore Classification Group IV.

In additional embodiments, the viral infection comprises an infection from a virus selected from the group consisting of filovirus, paramyxovirus, morbillivirus, rubulavirus, pneumovirus, vesiculovirus, lyssavrius, ephemerovirus, arenavirus, bunyavirus, hantavirus, nairovirus, phlebovirus, Orthohepadnavirus, Avihepadnavirus, Mammalian type B retroviruses, Mammalian type C retroviruses, Avian type C retroviruses, Type D retroviruses, BLV-HTLV retroviruses, Lentivirus, Spumavirus, and a combination thereof.

In some embodiments, the viral infection comprises an infection from a coronavirus, such as the virus referred to as COVID-19, SARS, or MERS.

In additional embodiments, the nucleic acid molecule, vector, pharmaceutical composition, or replication incompetent virus-like particle upon administration enters a liver cell.

In additional embodiments, the nucleic acid molecule, vector, pharmaceutical composition, or replication incompetent virus-like particle upon administration delivers the nucleic acid molecule to a liver cell and the nucleic molecule is expressed in the liver cell.

In additional embodiments, the subject has an acute, chronic, or latent viral infection.

In additional embodiments, administration induces an immune response against a cell infected with the virus causing the viral infection.

In additional embodiments, administration induces apoptosis in cells infected with the virus causing the viral infection.

Further provided is a method of inducing an immune response against a cell infected with a virus, in a subject in need thereof, the method comprising contacting the subject with any of the recombinant nucleic acid molecules described herein, or the vectors described herein, or the pharmaceutical compositions described herein, or the replication incompetent virus-like particles described herein.

Further provided is a method of inducing an apoptotic response against a cell infected with a virus, in a subject in need thereof, the method comprising contacting the subject with any of the recombinant nucleic acid molecules described herein, or the vectors described herein, or the pharmaceutical compositions described herein, or the replication incompetent virus-like particles described herein.

In additional embodiments, the virus is HBV, HDV, hepatitis A virus (HAV), hepatitis C virus (HCV), or any combination thereof.

Further provided is a method of treating hepatitis B in a subject, the method comprising administering to the subject a recombinant nucleic acid molecule described herein, or a vector described herein, or the pharmaceutical compositions described herein, or the replication incompetent virus-like particle described herein.

In additional embodiments, the method further comprises administering at least one antiviral agent, HBV polymerase inhibitor, interferon, TLR modulators such as TLR-7 agonists or TLR-9 agonists, therapeutic vaccines, immune activator of certain cellular viral RNA sensors, viral entry inhibitor, viral maturation inhibitor, distinct capsid assembly modulator, antiviral compounds of distinct or unknown mechanism, and any combination thereof.

In additional embodiments, the method further comprises administering at least one antiviral agent 3TC, FTC, L-FMAU, interferon, adefovir dipivoxil, entecavir, telbivudine (L-dT), valtorcitabine (3'-valinyl L-dC), .beta.-D-dioxolanyl-guanine (DXG), .beta.-D-dioxolanyl-2,6-diaminopurine (DAPD), .beta.-D-dioxolanyl-6-chloropurine (ACP), famciclovir, penciclovir, lobucavir, ganciclovir, ribavirin, and any combination thereof.

In additional embodiments, the treatment is administered periodically, including once every week, once every 2 weeks, once every 3 weeks, once a month, to once every two months, to once every 3 months, to once every 4 months, to once every 5 months, to once every 6 months, or once every 7 months, or once every 8 months, or once every 9 months, or once every 10 months, or every 11 months, or once annually as a maintenance treatment, or for as long as the patient requires to achieve stable or undetectable disease.

BRIEF DESCRIPTION OF THE DRAWINGS

FIG. 1A and FIG. 1B include a plasmid map and recombinant construct schematic showing features of the AAV8-HBV-DRS2 construct (6005 bp).

FIG. 2A, FIG. 2B, and FIG. 2C illustrate a non-limiting plasmid map, a graph showing viable cell data of test and control constructs in HepG2 (wild-type) and HepAD38 cells, along with the numeric data for experiment 1.

FIG. 3A and FIG. 3B illustrate a non-limiting plasmid map and chemical structure of a Caspase-9 inhibitor and a graph showing viable cell data of test and control constructs in HepG2 (wild-type) cells for experiment 2.

FIG. 4A, FIG. 4B, and FIG. 4C illustrate a non-limiting plasmid map and chemical structure of the Caspase-9 inhibitor (FIG. 4A), a graph showing viable cell data of test and control constructs in HepAD38 cells (HBV model cells) (FIG. 4B), along with the numeric data for experiment 2 (FIG. 4C).

FIG. 5A and FIG. 5B show a plasmid map (FIG. 5A) and comparative graph (FIG. 5B) showing the results for test and control constructs in HepG2 vs HepAD38 cells for experiment 2.

FIG. 6A, FIG. 6B, and FIG. 6C show a plasmid map for test construct AAV-HBV-DRS2 (TBG>HBV-rcCasp9) and chemical structure of the Caspase-9 inhibitor (FIG. 6A), and a comparative graph showing viable cell data of test and control constructs in HepG2 vs. HepAD38 cells (FIG. 6B), along with the numeric data for experiment 3 (FIG. 6C).

FIG. 7 is a plasmid map and construct schematic showing features of the AAV8-HBV-DRS1 construct and sequences (SEQ ID. NO: 33).

FIG. 8 is a plasmid map and construct schematic showing features of the AAV8-HBV-DRS2 construct and sequences (SEQ ID. NO: 34).

FIG. 11A, FIG. 11B, and FIG. 11C are images, graphs and a schematic showing results using the HBV hijack constructs in mouse models.

FIG. 14 illustrates a non-limiting plasmid map and construct schematic showing features and sequence of the Cov-2 Hijack DTA in vitro transcription vector (SEQ ID. NO: 35).

FIG. 15 illustrates a non-limiting plasmid map and construct schematic showing features and sequence of the SARS-CoV-2 hijack RNA construct (SEQ ID. NO: 36).

DETAILED DESCRIPTION

Figure 2A:
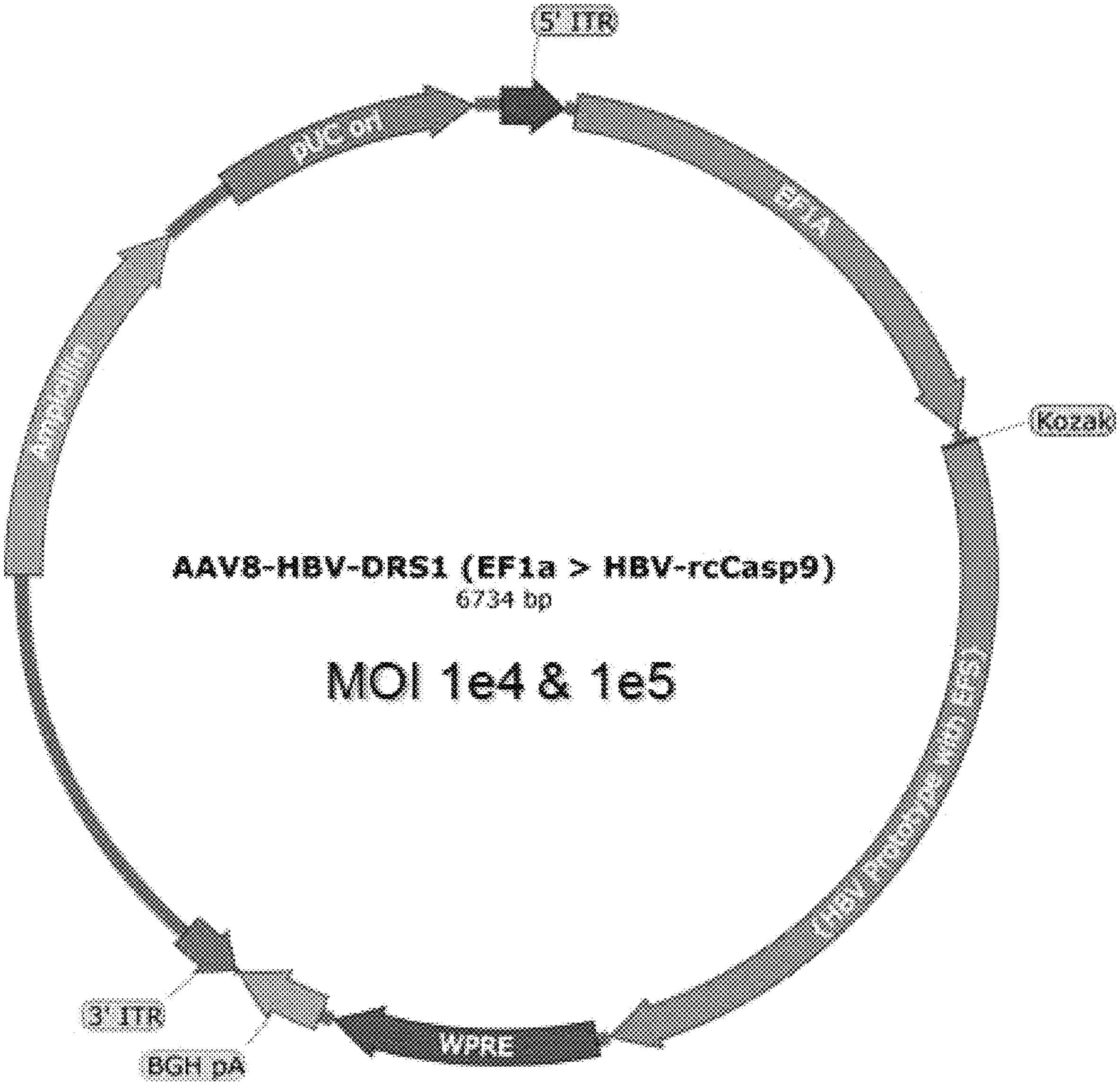
Figure 2B:
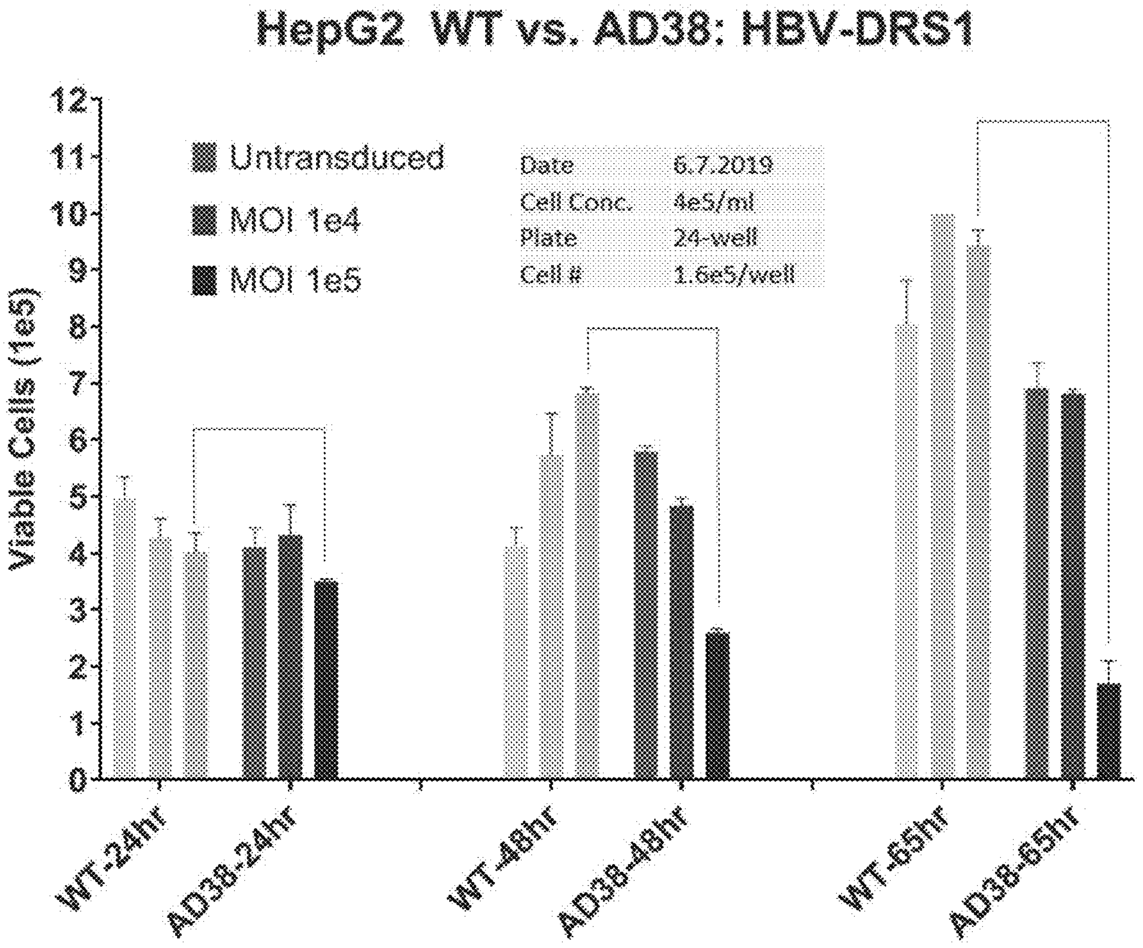
Figure 3B:
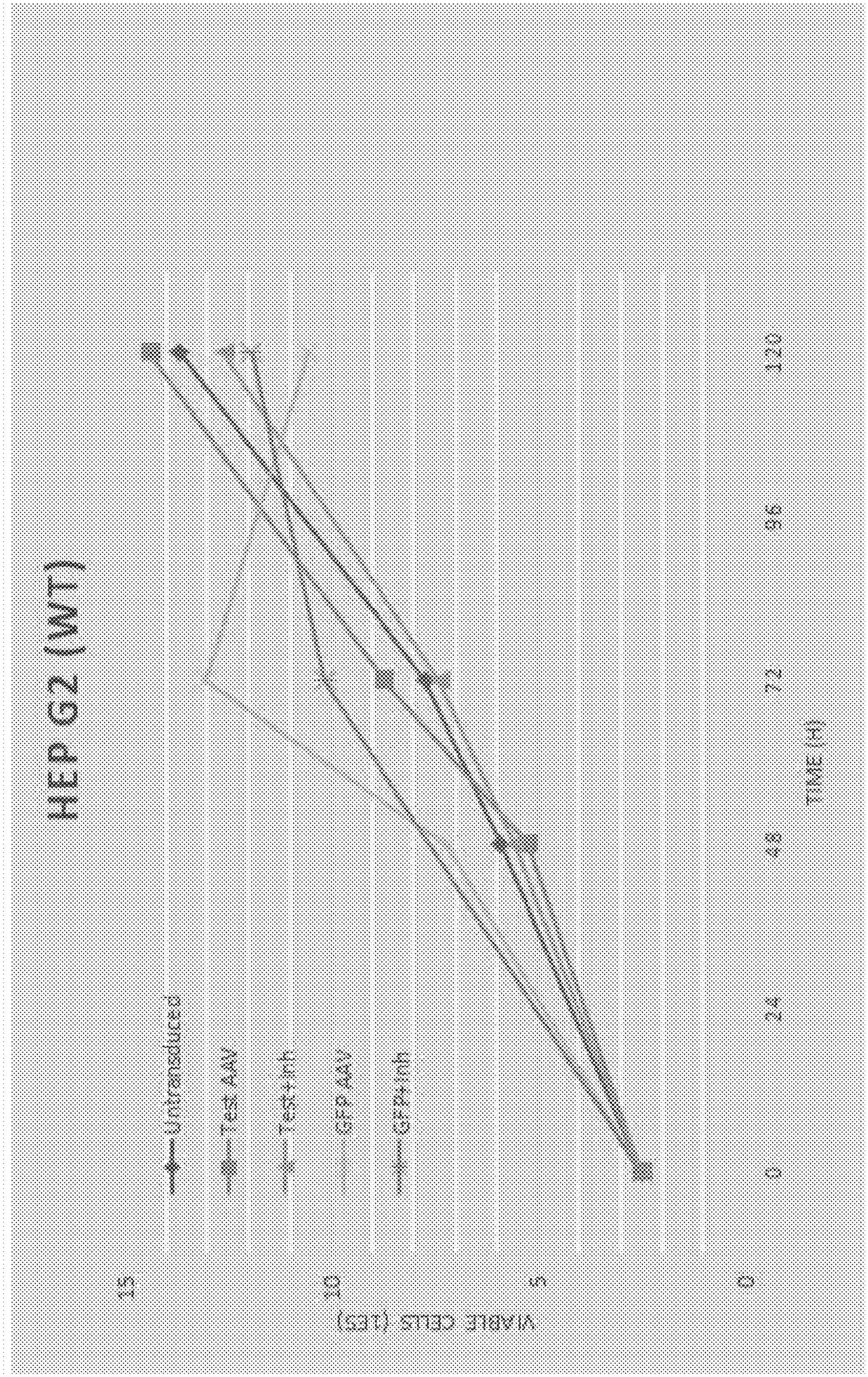
Figure 4B:
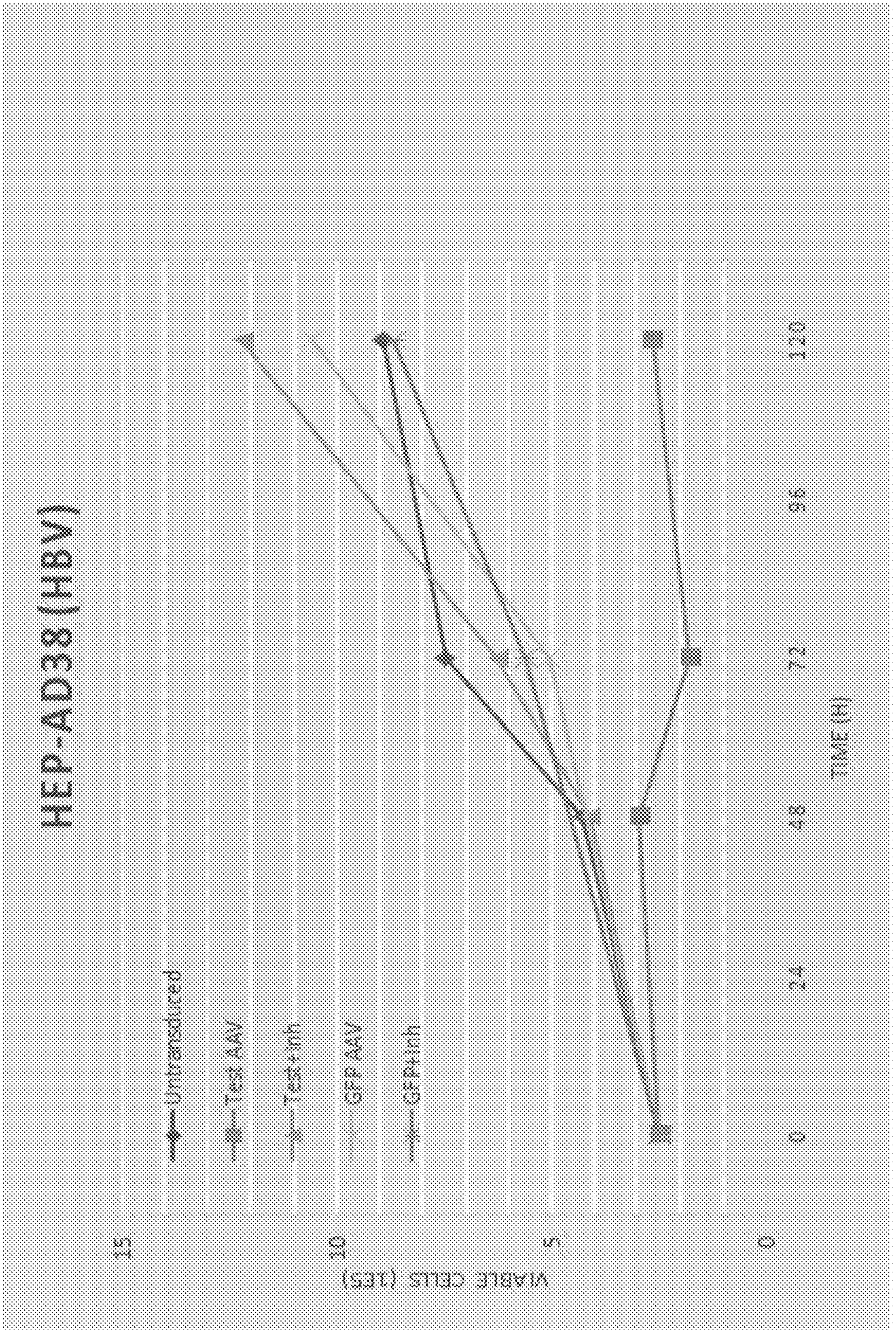

In certain embodiments, methods and compositions utilizing recombinant nucleic acid constructs or a replication incompetent virus-like particle encoding a chemokine, cytokine, or apoptosis inducing protein (e.g. Caspase 9 (Casp9) and others as provided herein), which will only be transcribed in the presence of a viral polymerase are provided. In certain embodiments, constructs carry sequences encoding for Casp9, which will result in killing of virally infected cells. These methods can be adapted to target many viral infections and reduce or eliminate viral load, and provide a fundamentally different treatment for viral infections.

Utilizing Viral Machinery to Destroy Virally Infected Cells

While not wishing to be bound by theory, the present methods and compositions are based at least in part on utilizing the viral machinery present typically in the cytoplasm of an infected cell. In certain embodiments, directing or injecting a recombinant nucleic acid construct or a replication incompetent virus-like particle (VLP) into a virally infected cell, wherein the construct or VLP comprises a single stranded RNA nucleic acid construct containing a sequence coding for a chemokine, cytokine, or apoptosis inducing protein, e.g., Casp 9 (and its promoter), flanked by hepatitis B epsilon signal binding sequences, to form a construct that will only be transcribed when recognized by the hepatitis B reverse transcriptase, will engage the epsilon sequence to transcribe the segment and result in translation of the coding sequence for Casp 9, which will trigger apoptosis of the hepatitis B infected cell. These constructs will effectively function as "viral specific suicide constructs" which will otherwise be degraded in non-virally infected cells.

Thus, in certain embodiments, the present compositions and methods encompass recombinant nucleic acid constructs and replication incompetent virus-like particles designed to target Hepatitis B infected cells. HBV is from Baltimore Group VII, which include double-stranded DNA viruses that replicate through a single-stranded RNA intermediate. This small group of viruses, exemplified by the Hepatitis B virus, have a double-stranded, gapped genome that is subsequently filled in to form a covalently closed circle (cccDNA) that serves as a template for production of viral mRNAs and a subgenomic RNA. The pregenome RNA serves as template for the viral reverse transcriptase for production of the DNA genome. This viral polymerase is what recognizes the flanking epsilon sequences in the recombinant nucleic acid constructs and replication incompetent virus-like particles described herein, and results in production of the toxic agent. Thus, only the virally infected cells will be killed by the production of the chemokine, cytokine, or apoptosis inducing protein (e.g. Caspase 9 (Casp9)).

In some embodiments, the chemokine, cytokine, or apoptosis inducing protein is flanked by the viral 5' UTR and the viral 3' UTR, such that the nucleic acid can be represented by the formula X—Y—Z, wherein X is the viral 5' UTR, Y is the protein of interest, such as a chemokine, cytokine, or apoptosis inducing protein (e.g. Caspase 9 or others as provided for herein, or diphtheria toxin A fragment), and Z is the viral 3' UTR. There may be intervening sequences between the 5' UTR and the protein of interest or the 3' UTR and the protein of interest. When the transcript is recognized by the cell it will produce a 5'-3' reverse complement encoding the protein of interest. This can be delivered as well in an AAV expression vector or other appropriate viral vector.

In some embodiments, the 5'-UTR is the 5' Leading Sequence of a coronavirus such as the virus that is referred to as COVID-19 (or COVD-19), SARS, or MERS. In some embodiments, the 5'-UTR comprises the sequence, or complement thereof, of:

```
                                          (SEQ ID NO: 25)
ATTAAAGGTTTATACCTTCCCAGGTAACAAACCAACCAACTTTCGATCT

CTTGTAGATCTGTTCTCTAAACGAACTTTAAAATCTGTGTGGCTGTCAC

TCGGCTGCATGCTTAGTGCACTCACGCAGTATAATTAATAACTAATTAC

TGTCGTTGACAGGACACGAGTAACTCGTCTATCTTCTGCAGGCTGCTTA

CGGTTTCGTCCGTGTTGCAGCCGATCATCAGCACATCTAGGTTTCGTCC

GGGTGTGACCGAAAGGTAAG
```

In some embodiments, the 3'UTR comprises the sequence, or complement thereof, of:

```
                                          (SEQ ID NO: 26)
CAATCTTTAATCAGTGTGTAACATTAGGGAGGACTTGAAAGAGCCACCA

CATTTTCACCGAGGCCACGCGGAGTACGATCGAGTGTACAGTGAACAAT

GCTAGGGAGAGCTGCCTATATGGAAGAGCCCTAATGTGTAAAATTAATT

TTAGTAGTGCTATCCCCATGTGATTTTAATAGCTTCTTAGGAGAATGAC

AAAAAAACAATCTTGCTAAACACTGTCTTCATG
```

In some embodiments, the nucleic acid sequence encoding diphtheria toxin A fragment comprises (or the complement thereof):

```
                                          (SEQ ID NO: 27)
ATGGGCGCTGATGATGTTGTTGATTCTTCTAAATCTTTTGTGATGGAAA

ACTTTTCTTCGTACCACGGGACTAAACCTGGTTATGTAGATTCCATTCA

AAAAGGTATACAAAAGCCAAAATCTGGTACACAAGGAAATTATGACGAT

GATTGGAAAGGGTTTTATAGTACCGACAATAAATACGACGCTGCGGGAT

ACTCTGTAGATAATGAAAACCCGCTCTCTGGAAAAGCTGGAGGCGTGGT
```

-continued

```
CAAAGTGACGTATCCAGGACTGACGAAGGTTCTCGCACTAAAAGTGGAT

AATGCCGAAACTATTAAGAAAGAGTTAGGTTTAAGTCTCACTGAACCGT

TGATGGAGCAAGTCGGAACGGAAGAGTTTATCAAAAGGTTCGGTGATGG

TGCTTCGCGTGTAGTGCTCAGCCTTCCCTTCGCTGAGGGGAGTTCTAGC

GTTGAATATATTAATAACTGGGAACAGGCGAAAGCGTTAAGCGTAGAAC

TTGAGATTAATTTTGAAACCCGTGGAAAACGTGGCCAAGATGCGATGTA

TGAGTATATGGCTCAAGCCTGTGCAGGAAATCGTGTCAGGCGATCAGTA

GGTAGCTCATTGTAA
```

In some embodiments, a composition comprising the sequence of:

```
                                          (SEQ ID NO: 28)
ATTAAAGGTTTATACCTTCCCAGGTAACAAACCAACCAACTTTCGATCT

CTTGTAGATCTGTTCTCTAAACGAACTTTAAAATCTGTGTGGCTGTCAC

TCGGCTGCATGCTTAGTGCACTCACGCAGTATAATTAATAACTAATTAC

TGTCGTTGACAGGACACGAGTAACTCGTCTATCTTCTGCAGGCTGCTTA

CGGTTTCGTCCGTGTTGCAGCCGATCATCAGCACATCTAGGTTTCGTCC

GGGTGTGACCGAAAGGTAAGATGGGCGCTGATGATGTTGTTGATTCTTC

TAAATCTTTTGTGATGGAAAACTTTTCTTCGTACCACGGGACTAAACCT

GGTTATGTAGATTCCATTCAAAAAGGTATACAAAAGCCAAAATCTGGTA

CACAAGGAAATTATGACGATGATTGGAAAGGGTTTTATAGTACCGACAA

TAAATACGACGCTGCGGGATACTCTGTAGATAATGAAAACCCGCTCTCT

GGAAAAGCTGGAGGCGTGGTCAAAGTGACGTATCCAGGACTGACGAAGG

TTCTCGCACTAAAAGTGGATAATGCCGAAACTATTAAGAAAGAGTTAGG

TTTAAGTCTCACTGAACCGTTGATGGAGCAAGTCGGAACGGAAGAGTTT

ATCAAAAGGTTCGGTGATGGTGCTTCGCGTGTAGTGCTCAGCCTTCCCT

TCGCTGAGGGGAGTTCTAGCGTTGAATATATTAATAACTGGGAACAGGC

GAAAGCGTTAAGCGTAGAACTTGAGATTAATTTTGAAACCCGTGGAAAA

CGTGGCCAAGATGCGATGTATGAGTATATGGCTCAAGCCTGTGCAGGAA

ATCGTGTCAGGCGATCAGTAGGTAGCTCATTGTAACAATCTTTAATCAG

TGTGTAACATTAGGGAGGACTTGAAAGAGCCACCACATTTTCACCGAGG

CCACGCGGAGTACGATCGAGTGTACAGTGAACAATGCTAGGGAGAGCTG

CCTATATGGAAGAGCCCTAATGTGTAAAATTAATTTTAGTAGTGCTATC

CCCATGTGATTTTAATAGCTTCTTAGGAGAATGACAAAAAAACAATCTT

GCTAAACACTGTCTTCATG
```

is provided, which encodes the 5'UTR, the 3' UTR and the protein of interest, which can be any sequence as provided herein. In the example above, the sequence encodes a diphtheria toxin A fragment.

In some embodiments, the nucleic acid sequence encoding diphtheria toxin A fragment is provided as the reverse complement, which can comprise the sequence of:

```
                                          (SEQ ID NO: 29)
TTACAATGAGCTACCTACTGATCGCCTGACACGATTTCCTGCACAGGCT

TGAGCCATATACTCATACATCGCATCTTGGCCACGTTTTCCACGGGTTT

CAAAATTAATCTCAAGTTCTACGCTTAACGCTTTCGCCTGTTCCCAGTT

ATTAATATATTCAACGCTAGAACTCCCCTCAGCGAAGGGAAGGCTGAGC

ACTACACGCGAAGCACCATCACCGAACCTTTTGATAAACTCTTCCGTTC

CGACTTGCTCCATCAACGGTTCAGTGAGACTTAAACCTAACTCTTTCTT

AATAGTTTCGGCATTATCCACTTTTAGTGCGAGAACCTTCGTCAGTCCT

GGATACGTCACTTTGACCACGCCTCCAGCTTTTCCAGAGAGCGGGTTTT

CATTATCTACAGAGTATCCCGCAGCGTCGTATTTATTGTCGGTACTATA

AAACCCTTTCCAATCATCGTCATAATTTCCTTGTGTACCAGATTTTGGC

TTTTGTATACCTTTTTGAATGGAATCTACATAACCAGGTTTAGTCCCGT

GGTACGAAGAAAAGTTTTCCATCACAAAAGATTTAGAAGAATCAACAAC

ATCATCAGCGCCCAT
```

In some embodiments, sequence is provided as the reverse complement, which can comprise the sequence of:

```
                                          (SEQ ID NO: 30)
CATGAAGACAGTGTTTAGCAAGATTGTTTTTTTGTCATTCTCCTAAGAA

GCTATTAAAATCACATGGGGATAGCACTACTAAAATTAATTTTACACAT

TAGGGCTCTTCCATATAGGCAGCTCTCCCTAGCATTGTTCACTGTACAC

TCGATCGTACTCCGCGTGGCCTCGGTGAAAATGTGGTGGCTCTTTCAAG

TCCTCCCTAATGTTACACACTGATTAAAGATTGTTACAATGAGCTACCT

ACTGATCGCCTGACACGATTTCCTGCACAGGCTTGAGCCATATACTCAT

ACATCGCATCTTGGCCACGTTTTCCACGGGTTTCAAAATTAATCTCAAG

TTCTACGCTTAACGCTTTCGCCTGTTCCCAGTTATTAATATATTCAACG

CTAGAACTCCCCTCAGCGAAGGGAAGGCTGAGCACTACACGCGAAGCAC

CATCACCGAACCTTTTGATAAACTCTTCCGTTCCGACTTGCTCCATCAA

CGGTTCAGTGAGACTTAAACCTAACTCTTTCTTAATAGITTCGGCATTA

TCCACTTTTAGTGCGAGAACCTTCGTCAGTCCTGGATACGTCACTTTGA

CCACGCCTCCAGCTTTTCCAGAGAGCGGGTTTTCATTATCTACAGAGTA

TCCCGCAGCGTCGTATTTATTGTCGGTACTATAAAACCCTTTCCAATCA

TCGTCATAATTTCCTTGTGTACCAGATTTTGGCTTTTGTATACCTTTTT

GAATGGAATCTACATAACCAGGTTTAGTCCCGTGGTACGAAGAAAAGTT

TTCCATCACAAAAGATTTAGAAGAATCAACAACATCATCAGCGCCCATC

TTACCTTTCGGTCACACCCGGACGAAACCTAGATGTGCTGATGATCGGC

TGCAACACGGACGAAACCGTAAGCAGCCTGCAGAAGATAGACGAGTTAC

TCGTGTCCTGTCAACGACAGTAATTAGTTATTAATTATACTGCGTGAGT
```

-continued

```
GCACTAAGCATGCAGCCGAGTGACAGCCACACAGATTTTAAAGTTCGTT

TAGAGAACAGATCTACAAGAGATCGAAAGTTGGTTGGTTTGTTACCTGG

GAAGGTATAAACCTTTAAT
```

Although the sequences provided herein (above and below) are represented as DNA sequences, the corresponding RNA sequences are also provided.

The terms "nucleic acid sequence" and "nucleic acid molecule", as used herein, can be used interchangeably.

In some embodiments, a recombinant nucleic acid sequence is provided that comprises a negative strand nucleic acid molecule or a pgRNA nucleic acid molecule encoding a chemokine, a cytokine, an apoptosis inducing protein, or a combination thereof, flanked by a first and second viral transcription recognition signal, and further comprising a first promoter upstream (5') of the first viral transcription recognition signal and a second promoter adjacent and 5' to the negative strand nucleic acid molecule or pgRNA nucleic acid molecule encoding a chemokine, a cytokine, a apoptosis inducing protein, diphtheria toxin A (or fragment thereof), or any combination thereof. Non-limiting examples of chemokines, cytokines, and apoptosis inducing proteins are provided herein. The actual protein that is flanked by the first and second viral transcription recognition signal can be any suitable protein. This encoded protein can also be replaced with any protein of interest, not just that encode for a chemokine, a cytokine, a apoptosis inducing protein, or a diphtheria toxin A (or fragment thereof).

As provided herein the negative strand nucleic acid molecule can be a negative sense RNA, negative sense DNA, single or double strand DNA that expresses a non-coding, negative sense RNA, or pgRNA, or any combination thereof. In some embodiments, the negative strand nucleic acid molecule is a negative sense RNA. In some embodiments, the negative strand nucleic acid molecule is a negative sense DNA. In some embodiments, the negative strand nucleic acid molecule is a single or double strand DNA that expresses a non-coding, negative sense RNA. In some embodiments, the negative strand nucleic acid molecule is a pgRNA.

As provided herein, in some embodiments, the viral transcription recognition signal is derived from or based on a virus that is, for example, a negative strand virus, an RNA reverse transcribing virus, or a DNA reverse transcribing virus. In some embodiments, the viral transcription recognition signal is a negative strand virus viral transcription recognition signal. In some embodiments, the viral transcription recognition signal is a RNA reverse transcribing virus viral transcription recognition signal. In some embodiments, the viral transcription recognition signal is a DNA reverse transcribing virus viral transcription recognition signal.

In some embodiments, the recombinant nucleic acid sequence comprises a poly A tail downstream (3') of the negative strand nucleic acid molecule or pgRNA nucleic acid molecule that also encodes the protein of interest, such as a toxin, chemokine, a cytokine, an apoptosis inducing protein, or combination thereof.

The apoptosis inducing protein can be any protein that is capable of inducing apoptosis based on its expression in a cell. Examples include, but are not limited to, BAX, BID, BAK, BAD, caspase 2, caspase 8, caspase 9, caspase 10, caspase 11, caspase 12, cytochrome C, SMAC, and apoptosis-inducing factor, or combinations thereof. Thus, these proteins can be expressed as the protein of interest in the construct that is administered to an infected individual or contacted with an infected cell to induce the cell death through the expression of these proteins of interest.

In some embodiments, the protein of interest is not a viral protein.

Examples of chemokines that can be used or encoded for by the present embodiments, include, but are not limited to, CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL8, CXCL9, CXCL10, CXCL11, CXCL12, CXCL13, CXCL14, CXCL15, CXCL16, CXCL17, XCL1, XCL2, and/or CX3CL1. In some embodiments, the cytokine is selected from the group consisting of IL-15, IL-2, IL-8, IL-10, IL-12, IL-6, IFN-α, IFN-β, IFN-γ, TNF-α, CD40L, Mig, and Crg-2.

As provided herein, in some embodiments, the recombinant nucleic acid sequence can further comprise a promoter that directs the expression of the nucleic acid sequences in the cell. In some embodiments, the promoter is a constitutive promoter. In some embodiments, the promoter is a tissue specific promoter. In some embodiments, the promoter is a liver-tissue-specific promoter. Examples of liver-tissue-specific promoters include, but are not limited to, TBG (Thyroxine Binding Globulin), albumin promoter and/or enhancing element, AFP (alpha-fetoprotein) promoter, AAT (Alpha-1-antitrypsin) promoter, ApoE (Apolipoprotein E) promoter or PEPCK (Phosphoenolpyruvate carboxykinase) promoter. The promoters can be used as the first promoter as referenced herein.

In some embodiments, the recombinant nucleic acid sequence comprises a second promoter. A non-limiting example of such a second promoter is elongation factor 1alpha binding sequence (EFS).

In some embodiments, the viral transcription recognition signal (sequence) comprises epsilon recognition signal (SEQ ID NO: 1) or a corona virus recognition sequence (such as those found in SEQ ID: 25, SEQ ID: 26, SEQ ID: 28, or SEQ ID: 30). Other viral transcription recognition signal sequences can also be used and be substituted for one that is specific for the virus or viral infection to be treated.

As provided herein, the present embodiments can be used to treat viral infections. And in some embodiments, the compositions and methods can be used to specifically kill virally infected cells. The benefit of specifically killing virally infected cells is that it can lead to the destruction of only of the cells that harbor the virus. Examples of viruses that can be used for the viral transcription recognition signal include, but are not limited to, corona virus (e.g. COVID-19, SARS, MERS), Hepatitis B virus, Hepatitis D virus, ebola virus, Marburg virus, human parainfluenza virus 1, measles virus, mumps virus, human respiratory syncytial virus, vesicular stomatitis Indiana virus, rabies virus, bovine ephemeral fever virus, lymphocytic choriomeningitis virus, Bunyamwera virus, Hantaan virus, Nairobi sheep disease virus, sandfly fever Sicilian virus, influenza virus A, influenza virus C, Thogoto virus, mouse mammary tumor virus, murine leukemia virus, avian leukosis virus, Mason-Pfizer monkey virus, bovine leukemia virus, human immunodeficiency virus 1, human spumavirus, duck hepatitis B virus, coronavirus, and a combination thereof. Without being bound to any particular theory, the choice of the viral transcription recognition signal sequence can be used to determine which type of viral infection is treated. For example, if the viral transcription recognition signal sequence is the COVID-19 viral transcription recognition signal sequence the nucleic acid molecules provided herein would only be expressed in cells infected COVID-19. COVID-19 is merely used as non-limiting example and should not be used to limit the embodiments provided herein.

In some embodiments, the nucleic acid molecules does not comprise sequences (coding or noncoding) for viral polymerase, reverse transcriptase, capsid, envelope, a packaging signal, or a translocation motif. In some embodiments, the recombinant nucleic acid molecule does not comprise sequences (coding or noncoding) for a viral polymerase. In some embodiments, the recombinant nucleic acid molecule does not comprise sequences (coding or noncoding) for a reverse transcriptase. In some embodiments, the recombinant nucleic acid molecule does not comprise sequences (coding or noncoding) for a capsid protein. In some embodiments, the recombinant nucleic acid molecule does not comprise sequences (coding or noncoding) for an envelope protein. In some embodiments, the recombinant nucleic acid molecule does not comprise sequences (coding or noncoding) for a packaging signal. In some embodiments, the recombinant nucleic acid molecule does not comprise sequences (coding or noncoding) for a translocation motif.

The recombinant nucleic acid molecules provided herein can be provided in a vector. The vector, for example, can be a delivery vector or vehicle for delivery to, for example, a mammalian cell, such as a human cell. In some embodiments, the cell is a cyno (e.g. monkey) cell. In some embodiments, the vector is a vector that can deliver the recombinant nucleic acid molecule to a human and a cyno cell. In some embodiments, the vector is a vector that can deliver the recombinant nucleic acid molecule to a human cell, but not a cyno cell. In some embodiments, the vector is a vector that can deliver the recombinant nucleic acid molecule to a cyno cell, but not a human cell.

In some embodiments, the delivery vector or vehicle is a VLP, an adeno-associated virus (AAV), a liposome, a nanoparticle, a micelle, a polymeric vesicle, or a polymersome. In some embodiments, the delivery vector or vehicle is an AAV vector. In some embodiments, the delivery vector or vehicle is a liposome. In some embodiments, the delivery vector or vehicle is a nanoparticle. In some embodiments, the delivery vector or vehicle is a micelle. In some embodiments, the delivery vector or vehicle is a polymeric vesicle. In some embodiments, the delivery vector or vehicle is a polymersome. Non-limiting examples of delivery vectors or vehicles include those that are described in U.S. Patent Application Publication No. 20200206362, U.S. Patent Application Publication No. 20200246267, U.S. Patent Application Publication No. 20170273907, and U.S. Pat. No. 10,556,018, each of which is hereby incorporated by reference in its entirety.

17. Also provided herein are replication incompetent virus-like particle (VLP) that can comprise the recombinant nucleic acid molecules provided herein. In some embodiments, the VLPs comprise an optional translocation motif (TLM) fused to a capsid protein from a virus of interest. For example, the capsid protein can be a hepatitis B viral capsid or a hepatitis D viral capsid or coronavirus fusion protein.

In some embodiments, the recombinant nucleic acid molecule provided by the VLP is a negative strand nucleic acid molecule or a pgRNA nucleic acid molecule encoding a protein of interest. As provided herein, the protein of interest is a chemokine, a cytokine, an apoptosis inducing protein, diphtheria toxin A (or fragment thereof) or a combination thereof. As provided herein, the sequence encoding the protein of interest can be flanked by a first and second viral transcription recognition signal, and further comprising a first promoter upstream (5') of the first viral transcription recognition signal and a second promoter adjacent and 5' to the negative strand nucleic acid molecule or pgRNA nucleic acid molecule encoding the protein of interest (e.g. a chemokine, a cytokine, a apoptosis inducing protein, or a combination thereof.) Non-limiting examples of a chemokine, a cytokine, a apoptosis inducing protein, or a combination thereof are provided herein.

In some embodiments, a replication incompetent virus-like particle (VLP) is provided that comprises a recombinant nucleic acid molecule, such as those provided herein (e.g. negative strand nucleic acid molecule or a pgRNA nucleic acid molecule), encoding a protein of interest (e.g., chemokine, a cytokine, a apoptosis inducing protein, or a combination thereof), flanked by a first and second target viral transcription recognition signal, and further comprising a first promoter upstream (5') of the first viral transcription recognition signal and a second promoter adjacent and 5' to the negative strand nucleic acid molecule or pgRNA nucleic acid molecule encoding a chemokine, a cytokine, a apoptosis inducing protein, or a combination thereof, wherein the VLP exhibits tropism for the target virally infected cells. The tropism can be controlled by the expression of a viral protein that is expressed on the surface of the VLP as well as controlling the expression of the nucleic acid molecule by the source of the viral transcription recognition signal sequences encoded by the recombinant nucleic acid molecule.

As provided herein, in some embodiments, the negative strand nucleic acid molecule is negative sense RNA, negative sense DNA, single or double strand DNA that expresses a non-coding, negative sense RNA, or pgRNA, or any combination thereof.

In some embodiments, the replication incompetent virus-like particle further comprises a poly A tail sequence downstream (3') of the negative strand nucleic acid molecule or pgRNA nucleic acid molecule encoding a chemokine, a cytokine, a apoptosis inducing protein, or combination thereof.

In some embodiments, the replication incompetent virus-like particle comprises promoter (e.g. a first promoter and a second promoter). Non-limiting examples of such promoters ae provided herein.

The overall design and the recombinant nucleic acid constructs and replication incompetent virus-like particles, as described herein can be adapted to encompass viruses from Baltimore Groups IV, V, VI, and VII. To target one of the Group IV-VII viruses, a specific viral polymerase recognition signal is utilized that would replace for example, the epsilon recognition signal sequence (SEQ ID NO: 1), as described for the HBV example. The Baltimore groups are described as follows:

Baltimore Group IV viruses: possess positive-sense single stranded RNA genomes, including the picornaviruses (which is a family of viruses that includes well-known viruses like Hepatitis A virus, enteroviruses, rhinoviruses, poliovirus, and foot-and-mouth virus), SARS virus, hepatitis C virus, yellow fever virus, and rubella virus. This group also includes the coronaviruses, hepeviruses (Hepatitis E), as well as the flaviviruses, such as Dengue virus, hepatitis C virus, yellow fever virus, and Zika virus.

Baltimore Group V viruses: single stranded RNA viruses; negative sense (e.g. Orthomyxoviruses, Rhabdoviruses).

Baltimore Group VI viruses: positive-sense single stranded RNA viruses that replicate through a DNA intermediate. (e.g. Retroviruses).

Baltimore Group VII viruses: double-stranded DNA viruses that replicate through a single-stranded RNA intermediate.

NSV Life Cycle and Replication

Negative-strand RNA viruses (NSV, or Baltimore Group V viruses) can be classified into 21 distinct families. The families consisting of nonsegmented genomes include Rhabdo-, Paramyxo-, Filo- and Borna-. Orthomyxo-, Bunya-, Arenaviridae-contain genomes of six to eight, three, or two negative-sense RNA segments, respectively. (See, Palese, P., et al., Proc. Natl. Acad. Sci. USA 93:11354-11358, 1996; and Boritz, Eli et al. *Journal of Virology.* 73 (8): 6937-6945, 1999).

Many highly prevalent human pathogens such as the respiratory syncytial virus (RSV), parainfluenza viruses, influenza viruses, Ebola virus, Marburg virus are included within the NSV. The life cycle of NSV has a number of steps. The virus first infects the host cell by binding to the host cell receptor through a viral surface glycoprotein. The fusion of the glycoprotein viral membrane with the plasma membrane of the host cell in an acidic environment allows for the release of viral ribonucleoprotein (RNP) complexes into the cytoplasm. Most NSV replicate in the cytoplasm of infected cells. Newly synthesized RNP complexes are assembled with viral structural proteins at the plasma membrane or at membranes of the Golgi apparatus. This is all followed by the release of the newly synthesized viruses.

Regarding the replication and transcription of non-segmented NSV, the genes of these NSV are made up of three regulatory regions: a gene end signal, an intergenic region, and a gene start signal. One example of gene end signals are in a specific virus called the vesicular stomatitis virus (VSV) contains gene end signals that are highly conservative. The intergenic region is highly variable and consists of conserved dinucleotide, trinucleotide, or regions of up to 143 nucleotides. The various lengths of the intergenic regions correlate with transcriptional attenuation, however diverse intergenic regions do not alter the gene expression. The gene start signals are highly specific as the first three nucleotides are critical for the gene expression.

Hepatitis B virus (HBV), a member of the Hepadnaviridae family, is a small DNA virus with unusual features similar to retroviruses. HBV replicates through an RNA intermediate and can integrate into the host genome. The unique features of the HBV replication cycle confer a distinct ability of the virus to persist in infected cells. Virological and serological assays have been developed for diagnosis of various forms of HBV-associated disease and for treatment of chronic hepatitis B infection. HBV infection leads to a wide spectrum of liver disease ranging from acute (including fulminant hepatic failure) to chronic hepatitis, cirrhosis, and hepatocellular carcinoma. Acute HBV infection can be either asymptomatic or present with symptomatic acute hepatitis. Most adults infected with the virus recover, but 5%-10% are unable to clear the virus and become chronically infected. Many chronically infected persons have mild liver disease with little or no long-term morbidity or mortality. Other individuals with chronic HBV infection develop active disease, which can progress to cirrhosis and liver cancer. Additionally, some individuals are infected with other hepatitis viruses in addition to HBV, such as hepatitis A, (HAV), hepatitis C (HCV), hepatitis D (HDV), or hepatitis E (HEV). Thus, treating HBV will assist in overcoming these co-infections, especially HDV, which requires HBV for its replication. Treating HBV will also lessen the likelihood of oncogenic abnormalities and cirrhosis.

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein and unless otherwise indicated, the term "about" is intended to mean±5% of the value it modifies. Thus, about 100 means 95 to 105. Additionally, the term "about" modifies a term in a series of terms, such as "about 1, 2, 3, 4, or 5" it should be understood that the term "about" modifies each of the members of the list, such that "about 1, 2, 3, 4, or 5" can be understood to mean "about 1, about 2, about 3, about 4, or about 5." The same is true for a list that is modified by the term "at least" or other quantifying modifier, such as, but not limited to, "less than," "greater than," and the like.

As used herein and in the appended claims, the singular forms "a", "an" and "the" include plural reference unless the context clearly dictates otherwise.

As used herein, the terms "comprise," "have," "has," and "include" and their conjugates, as used herein, mean "including but not limited to." While various compositions, and methods are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

Vector maps of the exemplary constructs used to test recombinant variants described herein are shown in FIG. 1A, FIG. 1B, FIG. 2A, FIG. 3A, FIG. 4A, FIG. 5A, FIG. 6A, FIG. 7, AND FIG. 8. While graphs of results testing these constructs are shown in FIG. 2B, FIG. 3B, FIG. 4B FIG. 4C, FIG. 5B, FIG. 6B and FIG. 6C. Exemplary sequences useful in these constructs are provided in SEQ ID NOs: 1-9. These are non-limiting examples and can be modified or tailored based on the virus of interest to be treated.

The terms "co-administration" or the like, are meant to encompass administration of the selected therapeutic agents to a single patient, and are intended to include treatment regimens in which the agents are administered by the same or different route of administration or at the same or different time.

As used herein, the term "agonist" refers to a compound, the presence of which results in a biological activity of a protein that is the same as the biological activity resulting from the presence of a naturally occurring ligand for the protein.

As used herein, the term "partial agonist" refers to a compound the presence of which results in a biological activity of a protein that is of the same type as that resulting from the presence of a naturally occurring ligand for the protein, but of a lower magnitude.

As used herein, the term "antagonist" refers to a compound, the presence of which results in a decrease in the magnitude of a biological activity of a protein. In certain embodiments, the presence of an antagonist results in complete inhibition of a biological activity of a protein. In certain embodiments, an antagonist is an inhibitor.

"Administering" when used in conjunction with a therapeutic composition (e.g. recombinant nucleic acid constructs and replication incompetent virus-like particles and compositions comprising these products) means to administer a therapeutic directly into or onto a target tissue or to administer a therapeutic to a patient whereby the therapeutic positively impacts the tissue to which it is targeted.

The term “subject” or “patient” as used herein includes, but is not limited to, humans and non-human vertebrates such as wild, domestic, and farm animals. In certain embodiments, the subject or patient described herein is an animal. In certain embodiments, the subject or patient is a mammal. In certain embodiments, the subject is a human. In certain embodiments, the subject or patient is a non-human animal. In certain embodiments, the subject or patient is a non-human mammal. In certain embodiments, the subject or patient is a domesticated animal, such as a dog, cat, cow, pig, horse, sheep, or goat. In certain embodiments, the subject or patient is a companion animal such as a dog or cat. In certain embodiments, the subject or patient is a livestock animal such as a cow, pig, horse, sheep, or goat. In certain embodiments, the subject or patient is a zoo animal. In another embodiment, the subject or patient is a research animal such as a rodent, dog, or non-human primate. In certain embodiments, the subject or patient is a non-human transgenic animal such as a transgenic mouse or transgenic pig.

The term “inhibit” includes the administration of a therapeutic of embodiments herein to prevent the onset of the symptoms, alleviating the symptoms, or eliminating the disease, condition or disorder.

By “pharmaceutically acceptable”, it is meant the carrier, diluent or excipient must be compatible with the other ingredients of the therapeutic and not deleterious to the recipient thereof.

The terms “treat,” “treated,” or “treating” as used herein refers to both therapeutic treatment and prophylactic or preventative measures, wherein the object is to inhibit, prevent or slow down (lessen) an undesired physiological condition, disorder or disease, or to improve, inhibit, or otherwise obtain beneficial or desired clinical results. For the purposes of this invention, beneficial or desired clinical results include, but are not limited to, improvement or alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

The term “antibody,” as used herein, refers to an immunoglobulin molecule which specifically binds with an antigen. Antibodies can be intact immunoglobulins derived from natural sources or from recombinant sources and can be immunoreactive portions of intact immunoglobulins. The antibodies may exist in a variety of forms including, for example, polyclonal antibodies, monoclonal antibodies, Fv, Fab and F(ab)2, as well as single chain antibodies and humanized antibodies.

The term “antibody fragment” refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

The term “antigen” as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an “antigen” as that term is used herein. Furthermore, one skilled in the art will understand that an antigen need not be encoded solely by a full length nucleotide sequence of a gene. It is readily apparent that the embodiments include, but are not limited to, the use of partial nucleotide sequences of more than one gene and that these nucleotide sequences are arranged in various combinations to elicit the desired immune response. Moreover, a skilled artisan will understand that an antigen need not be encoded by a “gene” at all. It is readily apparent that an antigen can be generated synthesized or can be derived from a biological sample. Such a biological sample can include, but is not limited to a tissue sample, a tissue sample suspected of containing a virus, a cell or a biological fluid.

The term “antigen” as used herein is defined as a molecule that provokes an immune response. This immune response may involve either antibody production, or the activation of specific immunologically-competent cells, or both.

As used herein, the term “ex vivo” refers to “outside” the body.

A “disease” is a state of health of a subject wherein the subject cannot maintain homeostasis, and wherein if the disease is not ameliorated then the animal’s health continues to deteriorate. In contrast, a “disorder” in a subject is a state of health in which the subject is able to maintain homeostasis, but in which the subject’s state of health is less favorable than it would be in the absence of the disorder. Left untreated, a disorder does not necessarily cause a further decrease in the subject’s state of health.

An “effective amount” as used herein, means an amount which provides a therapeutic or prophylactic benefit.

“Encoding” refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein “endogenous” refers to any material from or produced inside an organism, cell, tissue or system.

As used herein, the term “exogenous” refers to any material introduced from or produced outside an organism, cell, tissue or system.

The term “expression” as used herein is defined as the transcription and/or translation of a particular nucleotide sequence driven by its promoter.

“Expression vector” refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

In some embodiments, protein is at least, or about, 90, 91, 92, 93, 94, 95, 96, 97, 98, 99% homologous to the sequences provided herein. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell. An "isolated" biological component (such as a nucleic acid, protein or cell) has been substantially separated or purified away from other biological components (such as cell debris, other proteins, nucleic acids or cell types). Biological components that have been "isolated" include those components purified by standard purification methods.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

As used herein, recombinant generally refers to the following: A recombinant nucleic acid or protein is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

As used herein, the following abbreviations for the commonly occurring nucleic acid bases are used. "A" refers to adenosine, "C" refers to cytosine, "G" refers to guanosine, "T" refers to thymidine, and "U" refers to uridine.

The term "leukocytes" or "white blood cell" as used herein refers to any immune cell, including monocytes, neutrophils, eosinophils, basophils, and lymphocytes. The term "lymphocytes" as used herein refer to cells commonly found in lymph, and include natural killer cells (NK cells), T-cells, and B-cells. It will be appreciated by one of skill in the art that the above listed immune cell types can be divided into further subsets.

The term "tumor infiltrating leukocytes" as used herein refers to leukocytes that are present in a solid tumor.

The term "blood sample" as used herein refers to any sample prepared from blood, such as plasma, blood cells isolated from blood, and so forth.

The term "purified sample" as used herein refers to any sample in which one or more cell subsets are enriched. A sample may be purified by the removal or isolation of cells based on characteristics such as size, protein expression, and so forth.

Pharmaceutically acceptable vehicles: The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic compositions, and additional pharmaceutical agents.

In general, the nature of a suitable carrier or vehicle for delivery will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

In some embodiments, compositions, whether they be solutions, suspensions or other like form, may include one or more of the following: DMSO, sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

Diseases that the compositions and methods described herein can treat include microbial infections such as a viral infection.

By a "viral infection" is meant an infection caused by the presence of a virus in the body. Viral infections include chronic or persistent viral infections, which are viral infections that are able to infect a host and reproduce within the cells of a host over a prolonged period of time-usually weeks, months or years, before proving fatal.

Viruses giving rise to chronic infections include, for example, the human papilloma viruses (HPV), Herpes simplex, and other herpes viruses, the viruses of hepatitis B and C as well as other hepatitis viruses, human immunodeficiency virus, and the measles virus, all of which can produce important clinical diseases. Prolonged infection may ultimately lead to the induction of disease which may be, e.g., in the case of hepatitis C virus liver cancer, fatal to the patient. Other chronic viral infections which may be treated in accordance with the present invention include any Group V-VII virus that utilizes a virus-specific polymerase that can be used as an activating enzyme for transcribing the inactive recombinant nucleotide vector/VLP as described herein.

In certain embodiments, the recombinant nucleic acid constructs and replication incompetent virus-like particles, or compositions comprising such constructs/particles can be administered simultaneously with anti-microbial, anti-viral and/or other therapeutic agents. Alternatively, constructs/particles or composition comprising such constructs/particles can be administered at selected times in advance of times when anti-microbial, anti-viral and other therapeutic agents are administered.

Antivirals include, but are not limited to, ritonavir, acyclovir, cidofovir, ganciclovir, foscarnet, zidovudine, ribavirin, and hydroxychloroquine.

Antivirals further include, and are not limited to HIV treatments such as:

small molecule HIV fusion or entry inhibitors include: bevirimat (DSB; PA-457); Vicriviroc, Maraviroc (a chemokine receptor antagonist" or a "CCR5 inhibitor"), T-20 (enfuvirtide, Fuzeon, developed by Roche and Trimeris), TRI-1144, and TRI-999 (See, Qian, K et al, Med Res Rev. 2009 March; 29 (2): 369-393, and Haggani and Tilton, *Antiviral Res.* 2013 May; 98 (2): 158-70). Similarly, examples of anti-HIV mAbs include those against CCR5 and a CD4, and specifically: Ibalizumab (trade name Trogarzo) is a non-immunosuppressive humanized monoclonal antibody that binds CD4; PRO 140 is a humanized monoclonal antibody targeted against the CCR5.

Antiviral agents for combination treatment can include any one or combination of: an HBV polymerase inhibitor, interferon, TLR modulators such as TLR-7 agonists or TLR-9 agonists, therapeutic vaccines, immune activator of certain cellular viral RNA sensors, viral entry inhibitor, viral maturation inhibitor, distinct capsid assembly modulator, antiviral compounds of distinct or unknown mechanism.

Antiviral agents can also be any one or combination of: 3TC, FTC, L-FMAU, interferon, adefovir dipivoxil, entecavir, telbivudine (L-dT), valtorcitabine (3'-valinyl L-dC), .beta.-D-dioxolanyl-guanine (DXG), .beta.-D-dioxolanyl-2, 6-diaminopurine (DAPD), .beta.-D-dioxolanyl-6-chloropurine (ACP), famciclovir, penciclovir, lobucavir, ganciclovir, ribavirin, tenofovir, bictegravir, emtricitabine, Biktarvy, and any combination thereof.

In some embodiments, a "therapeutically effective amount" is an amount of recombinant nucleic acid constructs and replication incompetent virus-like particles, or composition comprising such constructs/particles, as described herein that results in a reduction in viral titer by at least 2.5%, at least 5%, at least 10%, at least 15%, at least 25%, at least 35%, at least 45%, at least 50%, at least 75%, at least 85%, by at least 90%, at least 95%, or at least 99% in a subject/patient/animal administered the recombinant nucleic acid constructs and replication incompetent virus-like particles, or composition comprising such constructs/particles and treated with a related method described herein, relative to the viral titer or microbial titer in an animal or group of animals (e.g., two, three, five, ten or more animals) not administered a recombinant nucleic acid constructs and replication incompetent virus-like particles, or composition comprising such constructs/particles of the invention.

Examples of Methods of Viral Vector-Mediated Transfer

In certain embodiments, a recombinant nucleic acid construct is incorporated into a viral like particle (defective in its ability to self-replicate) to mediate gene transfer to a cell. Typically, the virus simply will be exposed to the appropriate host cell under physiologic conditions, permitting uptake of the virus. (See, U.S. Pat. No. 9,089,520) The present methods can be adapted to utilize a variety of viral vectors or viral-like particles to deliver the recombinant constructs to a desired cellular target, as discussed below, and includes adenoviral vector systems, which are optimized to be incompetent, or non-replicating VLPs.

1. Adenovirus

Adenovirus is particularly suitable for use as a gene transfer vector because of its mid-sized DNA genome, ease of manipulation, high titer, wide target-cell range, and high infectivity. The roughly 36 kb viral genome is bounded by 100-200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, M. J. (1990) Radiother Oncol., 19, 197-218). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence, which makes them useful for translation.

In certain instances, it is helpful to maximize the carrying capacity of AAVs so that large segments of DNA can be included. It also is very desirable to reduce the toxicity and immunologic reaction associated with certain adenoviral products. The two goals are, to an extent, coterminous in that elimination of adenoviral genes serves both ends.

The large displacement of DNA is possible because the cis elements required for viral DNA replication all are localized in the inverted terminal repeats (ITR) (100-200 bp) at either end of the linear viral genome. Plasmids containing ITR's can replicate in the presence of a non-defective adenovirus (Hay, R. T., et al., J Mol. Biol. 1984 Jun. 5; 175 (4): 493-510). Therefore, deletion of these elements in an adenoviral vector will prevent independent replication.

In addition, the packaging signal for viral encapsulation is localized between 194-385 bp (0.5-1.1 map units) at the left end of the viral genome (Hearing et al., J. (1987) Virol., 67, 2555-2558). This signal mimics the protein recognition site in bacteriophage lambda DNA where a specific sequence close to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells (Levrero et al., Gene, 101:195-202, 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

To produce VLP/replication-deficient adenoviral vectors in vitro, these deficient vectors can be complemented, in trans, by helper virus. However, this does not permit isolation of the replication-deficient vectors, however, since the presence of helper virus, needed to provide replicative functions, would contaminate any preparation. Thus, an additional element that would add specificity to the replication and/or packaging of the replication-deficient vector is needed. That element derives from the packaging function of adenovirus.

It has been shown that a packaging signal for adenovirus exists in the left end of the conventional adenovirus map (Tibbetts et. al. (1977) Cell, 12, 243-249). Later studies showed that a mutant with a deletion in the E1A (194-358 bp) region of the genome grew poorly even in a cell line that complemented the early (E1A) function (Hearing and Shenk, (1983) J. Mol. Biol. 167, 809-822). When a compensating adenoviral DNA (0-353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved toward the interior of the Ad5 DNA molecule (Hearing et al., J. (1987) Virol., 67, 2555-2558).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals is packaged selectively when compared to the helpers. If the preference is great enough, stocks approaching homogeneity may be achieved.

To improve the tropism of ADV constructs for particular tissues or species, the receptor-binding fiber sequences can often be substituted between adenoviral isolates. For example the Coxsackie-adenovirus receptor (CAR) ligand found in adenovirus 5 can be substituted for the CD46-binding fiber sequence from adenovirus 35, making a virus with greatly improved binding affinity for human hematopoietic cells. The resulting "pseudotyped" virus, Ad5f35, has been the basis for several clinically developed viral isolates. Moreover, various biochemical methods exist to modify the fiber to allow re-targeting of the virus to target cells. Methods include use of bifunctional antibodies (with one end binding the CAR ligand and one end binding the target sequence), and metabolic biotinylation of the fiber to permit association with customized avidin-based chimeric ligands. Alternatively, one could attach ligands (e.g. anti-CD205 by heterobifunctional linkers (e.g. PEG-containing), to the adenovirus particle.

2. Retrovirus

The retroviruses are a group of single-stranded RNA viruses characterized by an ability to convert their RNA to double-stranded DNA in infected cells by a process of reverse-transcription (Coffin, (1990) In: Virology, ed., New York: Raven Press, pp. 1437-1500). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed psi, functions as a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and psi components is constructed (Mann et al., (1983) Cell, 33, 153-159). When a recombinant plasmid containing a human cDNA, together with the retroviral LTR and psi sequences is introduced into this cell line (by calcium phosphate precipitation for example), the psi sequence allows the RNA transcript of the recombinant plasmid to be packaged into viral particles, which are then secreted into the culture media (Nicolas, J. F., and Rubenstein, J. L. R., (1988) In: Vectors: a Survey of Molecular Cloning Vectors and Their Uses, Rodriquez and Denhardt, Eds.). Nicolas and Rubenstein; Temin et al., (1986) In: Gene Transfer, Kucherlapati (ed.), New York: Plenum Press, pp. 149-188; Mann et al., 1983). The media containing the recombinant retroviruses is collected, optionally concentrated, and used for gene transfer. Retroviral vectors are able to infect a broad variety of cell types. However, integration and stable expression of many types of retroviruses require the division of host cells (Paskind et al., (1975) Virology, 67, 242-248). An approach designed to allow specific targeting of retrovirus vectors recently was developed based on the chemical modification of a retrovirus by the chemical addition of galactose residues to the viral envelope. This modification could permit the specific infection of cells such as hepatocytes via asialoglycoprotein receptors, may this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., (1989) Proc. Nat'l Acad. Sci. USA, 86, 9079-9083). Using antibodies against major histocompatibility complex class I and class II antigens, the infection of a variety of human cells that bore those surface antigens was demonstrated with an ecotropic virus in vitro (Roux et al., 1989).

3. Adeno-Associated Virus

AAV utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42-46, is the same for each transcript. The four non-structural proteins apparently are derived from the longer of the transcripts, and three virion proteins all arise from the smallest transcript.

AAV is not associated with any pathologic state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low-level expression of AAV rep proteins is believed to hold AAV structural expression in check, and helper virus infection is thought to remove this block.

The terminal repeats of the AAV vector can be obtained by restriction endonuclease digestion of AAV or a plasmid such as p201, which contains a modified AAV genome (Samulski et al., J. Virol., 61:3096-3101 (1987)), or by other methods, including but not limited to chemical or enzymatic synthesis of the terminal repeats based upon the published sequence of AAV. It can be determined, for example, by deletion analysis, the minimum sequence or part of the AAV ITRs which is required to allow function, i.e., stable and site-specific integration. It can also be determined which minor modifications of the sequence can be tolerated while maintaining the ability of the terminal repeats to direct stable, site-specific integration.

AAV-based vectors have proven to be safe and effective vehicles for gene delivery in vitro, and these vectors are being developed and tested in pre-clinical and clinical stages for a wide range of applications in potential gene therapy, both ex vivo and in vivo (Carter and Flotte, (1995) Ann. N.Y. Acad. Sci., 770; 79-90; Chatteijee, et al., (1995) Ann. N.Y. Acad. Sci., 770, 79-90; Ferrari et al., (1996) J. Virol., 70, 3227-3234; Fisher et al., (1996) J. Virol., 70, 520-532; Flotte et al., Proc. Nat'l Acad. Sci. USA, 90, 10613-10617, (1993); Goodman et al. (1994), Blood, 84, 1492-1500; Kaplitt et al., (1994) Nat'l Genet., 8, 148-153; Kaplitt, M. G., et al., Ann Thorac Surg. 1996 December; 62 (6): 1669-76; Kessler et al., (1996) Proc. Nat'l Acad. Sci. USA, 93, 14082-14087; Koeberl et al., (1997) Proc. Nat'l Acad. Sci. USA, 94, 1426-1431; Mizukami et al., (1996) Virology, 217, 124-130).

AAV-mediated efficient gene transfer and expression in the lung has led to clinical trials for the treatment of cystic fibrosis (Carter and Flotte, 1995; Flotte et al., Proc. Nat'l Acad. Sci. USA, 90, 10613-10617, (1993)). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., (1996) J. Virol., 70, 520-532; Flotte et al., 1993; Kaplitt et al., 1994; 1996; Koeberl et al., 1997; McCown et al., (1996) Brain Res., 713, 99-107; Ping et al., (1996) Microcirculation, 3, 225-228; Xiao et al., (1996) J. Virol., 70, 8098-8108).

The challenges associated with liver-directed gene therapy are efficient targeting of hepatocytes, stability of the vector genome, and persistent high level expression. Many of these obstacles can be overcome with adeno-associated viral (AAV) gene transfer vectors. The first AAV gene transfer vector developed for in vivo use was based on the AAV2 serotype. AAV2 has a broad tropism and transduces many cell types, including hepatocytes, relatively efficiently in vivo. The capsid protein confers the serological profile and at least 12 primate AAV serotypes have already been characterized. Importantly, pseudotyping a recombinant AAV vector with different capsid proteins can dramatically alter the tropism. Both AAV8 and AAV9 have higher affinities for hepatocytes when compared to AAV2. In particular, AAV8 can transduce 3-4 fold more hepatocytes and deliver 3-4 fold more genomes per transduced cell when compared to AAV2 (See, Mark S. Sands, *Methods Mol. Biol.* 2011; 807:141-157). Depending on the dose, AAV8 can transduce up to 90-95% of hepatocytes in the mouse liver following intraportal vein injection. Interestingly, comparable levels of transduction can be achieved following intravenous injection. Direct intraparenchymal injection of an AAV vector also mediates relatively high level long term expression. Additional specificity can be conferred by using liver-specific promoters in conjunction with AAV8 capsid proteins. In addition to treating primary hepatocyte defects, immune reactions to transgene products can be minimized by circumventing the fixed tissue macrophages of the liver, Kupffer cells, and limiting expression to hepatocytes. The ability to target hepatocytes by virtue of the AAV serotype and the use of liver-specific promoters allows testing novel therapeutic approaches.

4. Lentiviral Vectors

In certain embodiments, the recombinant nucleic acid or replication incompetent VLPs are transduced into the target cells, by electroporation, or by transfection of nucleic acids, proteins, site-specific nucleases, self-replicating RNA viruses or integration-deficient lentiviral vectors. (for such vectors see, U.S. Pat. No. 10,131,876).

In certain embodiments, transduction is performed with lentiviruses, gamma-, alpha-retroviruses or adenoviruses or with electroporation or transfection by nucleic acids (DNA, mRNA, miRNA, antagomirs, ODNs), proteins, site-specific nucleases (zinc finger nucleases, TALENs, CRISP/R), self-replicating RNA viruses (e.g. equine encephalopathy virus) or integration-deficient lentiviral vectors.

In further embodiments, delivery of the recombinant nucleic acid or replication incompetent VLPs may be performed by transducing said cells with lentiviral vectors (See, Cockrell Adam S et al., "Gene delivery by lentivirus vectors", Molecular Biotechnology, vol. 36, No. 3, July 2007.)

Lentiviral vectors with the VSVG pseudotype enable efficient transduction under automated manufacturing method. However, the present methods are entirely suitable for the use of any type of lentiviral vector (with e.g. measles virus (ML-LV), gibbon ape leukaemia virus (GALV), feline endogenous retrovirus (RD114), baboon endogenous retrovirus (BaEV) derived pseudotyped envelopes). Other viral vectors such as gamma or alpha retroviral vectors can be used. Transduction enhancer reagents can be added when necessary using the automated manufacturing described in this invention.

5. Other Viral Vectors

Other viral vectors can be employed as expression constructs in the present methods and compositions. Vectors derived from viruses such as vaccinia virus (Ridgeway, (1988) In: Vectors: A survey of molecular cloning vectors and their uses, pp. 467-492; Baichwal and Sugden, (1986) In, Gene Transfer, pp. 117-148; Coupar et al., Gene, 68:1-10, 1988) canary poxvirus, and herpes viruses are employed. These viruses offer several features for use in gene transfer into various mammalian cells.

Methods for Treating a Disease

The present methods also encompass methods of treatment or prevention of a viral disease or condition where administration of recombinant nucleic acids, VLP products, or pharmaceutical compositions can be delivered in various effective amounts.

The term "unit dose" as it pertains to the inoculum refers to physically discrete units suitable as unitary dosages for mammals, each unit containing a predetermined quantity of pharmaceutical composition calculated to produce the desired immunogenic effect in association with the required diluent. The specifications for the unit dose of an inoculum are dictated by and are dependent upon the unique characteristics of the pharmaceutical composition and the particular immunologic effect to be achieved.

An effective amount of the recombinant nucleic acids, VLP products or pharmaceutical compositions thereof, would be an amount, such that over 60%, 70%, 80%, 85%, 90%, 95%, or 97% of the virally infected, e.g. HBV, Covid-19, etc. infected cells are killed. The term is also synonymous with "sufficient amount."

The effective amount for any particular application can vary depending on such factors as the disease or condition being treated, the particular composition being administered, the size of the subject, and/or the severity of the disease or condition. One can empirically determine the effective amount of a particular composition presented herein without necessitating undue experimentation.

The terms "contacted" and "exposed," when applied to a cell, tissue or organism, are used herein to describe the process by which the pharmaceutical composition and/or another agent, such as for example an anti-viral agent, are delivered to a target cell, tissue or organism or are placed in direct juxtaposition with the target cell, tissue or organism. To achieve cell killing or stasis, recombinant nucleic acids, VLP products or pharmaceutical compositions thereof, and/or additional agent(s) are delivered to one or more cells in a combined amount effective to kill the virally infected cell(s) or prevent them from dividing. The administration of the recombinant nucleic acid, VLP products, or pharmaceutical composition may precede, be co-current with and/or follow the other agent(s) by intervals ranging from minutes to weeks. In embodiments where the pharmaceutical composition and other agent(s) are applied separately to a cell, tissue or organism, one would generally ensure that a significant period of time did not expire between the times of each delivery, such that the pharmaceutical composition and agent(s) would still be able to exert an advantageously combined effect on the cell, tissue or organism. For example, in such instances, it is contemplated that one may contact the cell, tissue or organism with two, three, four or more modalities substantially simultaneously (i.e., within less than about a minute) with the pharmaceutical composition. In other aspects, one or more agents may be administered substantially simultaneously, about 1 minute, to about 24 hours to about 7 days to about 1 to about 8 weeks or more, and any range derivable therein, prior to and/or after administering the recombinant nucleic acid, VLP, or pharmaceutical products. Yet further, various combination regimens of the pharmaceutical composition presented herein and one or more agents may be employed.

Formulations and Routes for Administration to Patients

Where clinical applications are contemplated, it will be necessary to prepare pharmaceutical compositions—expression constructs, expression vectors, fused proteins, transfected or transduced cells, in a form appropriate for the intended application. Generally, this will entail preparing compositions that are essentially free of pyrogens, as well as other impurities that could be harmful to humans or animals.

The recombinant nucleic acids, VLP products or pharmaceutical compositions thereof, may be delivered, for example at doses of about 1-5 million particles per dose. Vials or other containers may be provided containing the product, for example, a volume per vial of about 0.25 ml to about 10 ml, for example, about 0.25, 0.5, 1, 1.5, 2, 2.5, 3, 3.5, 4, 4.5, 5, 5.5, 6, 6.5, 7, 7.5, 8, 8.5, 9, 9.5, or 10 ml, for example, about 2 ml.

One may generally desire to employ appropriate salts and buffers when recombinant nucleic acid or VLP products are introduced into a patient. The phrase "pharmaceutically or pharmacologically acceptable" refers to molecular entities and compositions that do not produce adverse, allergic, or other untoward reactions when administered to an animal or a human. A pharmaceutically acceptable carrier includes any and all solvents, dispersion media, coatings, antibacterial and antifungal agents, isotonic and absorption delaying agents and the like. The use of such media and agents for pharmaceutically active substances is known. Except insofar as any conventional media or agent is incompatible with the vectors or cells, its use in therapeutic compositions is contemplated. Supplementary active ingredients also can be incorporated into the compositions.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution may be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media can be employed. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations may meet sterility, pyrogenicity, and general safety and purity standards as required by FDA Office of Biologics standards.

The compositions may be formulated for aerosolized delivery to a subject. For aerosol delivery, the compositions described may be formulated in aqueous solutions such as water or in physiologically compatible buffers such as Hanks's solution, Ringer's solution, or physiological saline buffer. The solution may contain one or more formulatory agents such as suspending, stabilizing or dispersing agents.

Delivery systems of the disclosure that deliver the polynucleotides of the disclosure to a desired cell of a subject are not limited to the VLPs of the disclosure. In some embodiments, the delivery vector comprises an adeno-associated virus (AAV) vector, a liposome, a nanoparticle, a micelle, a polymeric vesicle or a polymersome.

In some embodiments, the delivery vector comprises a vector derived from an AAV. AAV vectors are among the most frequently used vectors for gene therapy. AAV is a small, non-enveloped Class II virus, whose genome is encoded in one long single stranded DNA molecule. AAV derived vectors have the ability to attach and enter a target cell, transfer genetic material to the nucleus, and have that information be expressed for sustained periods of time with a general lack of toxicity. AAV derived vectors typically do not encode AAV components necessary for site specific integration into the host genome, and typically persist as extrachromosomal elements. AAV vectors are also capable, to some degree, of selective tissue and organ targeting. Thus, AAV vectors are a possible delivery mechanism for the single stranded DNA polynucleotides of the disclosure to a desired cell of a subject.

In some embodiments, the recombinant polynucleotides of the disclosure can be packaged into a non-viral delivery system to be delivered to a desired target cell of a subject. In some embodiments, the polynucleotides of the disclosure are packaged into a nanoparticle, a micelle, a polymeric vesicle or a polymersome to be delivered to a desired target cell of a subject. In some embodiments, the these products can be formulated into an aerosol for delivery by inhaler, or by nanoparticle. Additional routes of delivery include: topical, transdermal, intravenous, sub-cutaneous, and intrathecal delivery. In some embodiments, the nanoparticle encapsulates the ssRNA encoding the therapeutic, which can then be administered systemically or locally, such as by aerosol delivery. Aerosol delivery can be used to deliver the therapeutic to the lungs of a patient that is infected with a virus as provided herein, such as a coronavirus.

Additionally, in certain patients, it is expected that this treatment would be repeated periodically to reduce or eliminate any remaining virus/virions. Such periodic treatment can vary from once every week, once every 2 weeks, once every 3 weeks, once a month, to once every two months, to once every 3 months, to once every 4 months, to once every 5 months, to once every 6 months, or once every 7 months, or once every 8 months, or once every 9 months, or once every 10 months, or every 11 months, or once annually as a maintenance treatment for as long as the patient requires to achieve stable or undetectable disease.

Combination and Alternation Therapy

It has been recognized that drug-resistant variants of many viral infections including HIV, HBV and HCV can emerge after prolonged treatment with an antiviral agent. Drug resistance most typically occurs by mutation of a gene that encodes for a protein such as an enzyme used in viral replication, and most typically in the case of HIV, reverse transcriptase, protease, or DNA polymerase, and in the case of HBV, DNA polymerase, or in the case of HCV, RNA polymerase, protease, or helicase. Recently, it has been demonstrated that the efficacy of a drug against HIV infection can be prolonged, augmented, or restored by administering the compound in combination or alternation with a second, and perhaps third, antiviral compound that induces a different mutation from that caused by the principle drug. The compounds can be used for combination are selected from the group consisting of a HBV polymerase inhibitor, interferon, TLR modulators such as TLR-7 agonists or TLR-9 agonists, therapeutic vaccines, immune activator of certain cellular viral RNA sensors, viral entry inhibitor, viral maturation inhibitor, distinct capsid assembly modulator, antiviral compounds of distinct or unknown mechanism, and combination thereof. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

In certain embodiments, the method includes a regimen of controlling for cell death, by keeping the patient on anti-viral treatment such as tenofovir, etc. during delivery of the construct; then cycling the patient off of the anti-viral treatment for periods or time ranging from 2 weeks to 1 month, allowing for viral replication and limiting the viral cell death, so that there is not an overwhelming viral hepatic cell death situation, or similar cell death.

Following such a cycle, the patient is returned to anti-viral treatment, allowing for repair of the tissue; and repeating of the cycle every 8 weeks, every 12 weeks, every 16 weeks, every 20 weeks, etc. for as long as there is benefit to the patient.

Additional compounds for combination or alternation therapy for the treatment of HBV include 3TC, FTC, L-FMAU, interferon, adefovir dipivoxil, entecavir, telbivudine (L-dT), valtorcitabine (3'-valinyl L-dC), .beta.-D-dioxolanyl-guanine (DXG), .beta.-D-dioxolanyl-2,6-diaminopurine (DAPD), and .beta.-D-dioxolanyl-6-chloropurine (ACP), famciclovir, penciclovir, lobucavir, ganciclovir, and ribavirin.

Kits

Additionally, certain components or embodiments of these recombinant nucleic acids, VLP products or pharmaceutical compositions thereof, can be provided in a kit. For example, any of the recombinant nucleic acids, or VLP products, can be provided frozen and packaged as a kit, alone or along with separate containers of any of the other agents from the pre-conditioning or post-conditioning steps, and optional instructions for use.

Some embodiments are also directed to any of the aforementioned compositions in a kit. In some embodiments, the kit may comprise ampoules, disposable syringes, capsules, vials, tubes, or the like. In some embodiments, the kit may comprise a single dose container or multiple dose containers comprising the topical formulation of embodiments herein. In some embodiments, each dose container may contain one or more unit doses. In some embodiments, the kit may include an applicator. In some embodiments, the kits include all components needed for the stages of conditioning/treatment. In some embodiments, the cellular compositions may have preservatives or be preservative-free (for example, in a single-use container). In some embodiments, the recombinant nucleic acids or VLP products may be prepared and frozen at a desired stage, suitable for shipping to a hospital or treatment center.

Additionally, in certain patients, it is expected that any of the methods or treatment regimens would be repeated periodically to boost the immune system response to the viral agent/s. Such periodic treatment can vary from once every week, month, to once every two months, to once every 3 months, to once every 4 months, to once every 5 months, to once every 6 months, or once every 7 months, or once every 8 months, or once every 9 months, or once every 10 months, or every 11 months, or once annually as a maintenance treatment for as long as the patient requires.

Although the invention has been described with respect to various preferred embodiments, it is not intended to be limited thereto, but rather those skilled in the art will recognize that variations and modifications may be made therein which are within the spirit of the invention and the scope of the appended claims.

In certain embodiments, test constructs described herein utilize AAV8 as the delivery vector because it targets liver cells; non-specific targeting will be tested in the various controls as indicated. TBG (Thyroxine Binding Globulin) is utilized as a liver-specific promoter, it is turned on by specific transcription factors made only in liver cells. This will drive expression of the recombinant transcript, which is in reverse complementary structure, and hence deemed non-functional and further undergoes degradation, without the presence of the viral transcription recognition signal, which in this case is the epsilon sequence (SEQ ID NO: 1).

These experiments are designed to show that the test constructs will only be expressed in HBV-infected liver cells, where the HBV DNA polymerase is present, and interacts with the embedded HBV Epsilon transcription recognition sequences and transcribes the HBV "viral suicide" transcript. After this process, the sense HBV transcripts (which is the sense transcript recognized by the epsilon sequence, encoding Casp9) can now be transcribed and translated by host cell machinery to encode for Casp 9, which is under the strong constitutively active EFS promoter, that initiates the programmed cell death-apoptosis of the virally infected host cells, sparing any other uninfected cell from apoptosis.

These results are illustrated in the schematics, maps, graphs and tables from FIGS. 1-12, and are more fully explained below in Examples 1-6.

Example 1

The HepAD38 is a cell line that replicates human hepatitis B virus (HBV) under conditions that can be regulated with tetracycline. In the presence of the antibiotic, this cell line is free of virus due to the repression of pregenomic (pg) RNA synthesis. Upon removal of tetracycline from the culture medium, the cells express viral pg RNA, accumulate subviral particles in the cytoplasm that contain DNA intermediates characteristic of viral replication, and secrete virus-like particles into the supernatant. Since the HepAD38 cell line can produce high levels of HBV DNA, it should be useful for analyses of the viral replication cycle that depend upon viral DNA synthesis in a synchronized fashion. In addition, this cell line has been formatted into a high-throughput, cell-based assay that permits the large-scale screening of diverse compound libraries for new classes of inhibitors of HBV replication. See, Ladner S. K. et al. Antimicrob Agents Chemother. 1997 August; 41 (8): 1715-20. Thus, the HepAD38 cell line a suitable in vitro model system for the study of human hepatitis B virus (HBV).

Hep G2 is an immortal cell line which was derived from the liver tissue of a 15-year-old American adolescent boy of European ancestry with a well-differentiated hepatocellular carcinoma. These cells are epithelial in morphology, have a modal chromosome number of 55, and are not tumorigenic in nude mice. The cells secrete a variety of major plasma proteins, e.g., albumin, and the acute-phase proteins fibrinogen, alpha 2-macroglobulin, alpha 1-antitrypsin, transferrin and plasminogen. They have been grown successfully in large-scale cultivation systems. Hepatitis B virus surface antigens have not been detected on these cells. Hep G2 will respond to stimulation with human growth hormone. Thus, Hep G2 cells are a suitable in vitro model system for the study of polarized human hepatocytes.

For testing the "viral specific cytotoxic" constructs described herein, utilizing HepG2 cells served as a control for normal, healthy liver cells. Since HepG2 cells are liver cells that are not infected with HBV, they should be unaffected by the test replication incompetent: AAV8-HBV-DRS1 (EF1a>HBV-rcCasp9), used in Experiment 1, with results shown in FIG. 2A and FIG. 2C.

In contrast, the HepAD38 cell line was utilized as the HBV+ model for testing one of the "viral specific cytotoxic" constructs described herein: the replication incompetent construct: AAV8-HBV-DRS1 (EF1a>HBV-rcCasp9) (vector shown in FIG. 2A). The results shown for Experiment 1, Groups 1-3 illustrate that the Group 2 test construct AAV8-HBV-DRS1 (EF1a>HBV-rcCasp9) in HepAD38 cells, exhibited viral specific cell death, as shown in the graphic data of FIG. 2B, and corresponding cell numbers and viability described in FIG. 2C.

Example 2

Figure 5B:
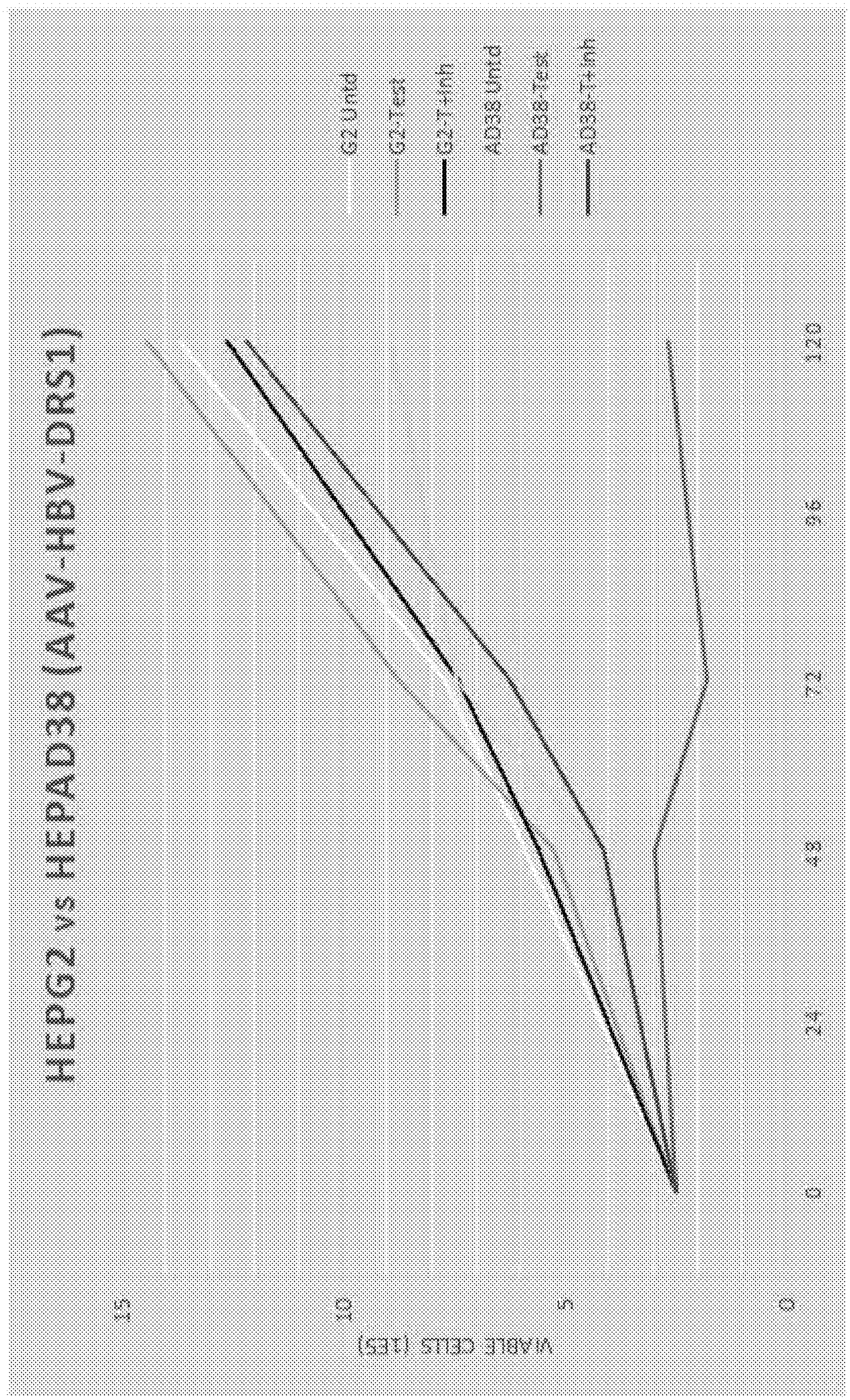

Additionally, in Experiment 2, shown in FIG. 3A and FIG. 3B, and FIG. 4A, FIG. 4B and FIG. 4C, the AAV8-HBV-DRS1 (EF1a>HBV-rcCasp9) construct was further tested in HepG2 cells and HepAD38 cells and in certain test groups the Caspase-9 inhibitor Z-LEHD-FMK was used to illustrate that the killing was the result of Casp9 expression (See Group 3 and Group 5). The results from these experiments illustrate the viral specific cell death in the Group 2 HepAD38 cells, which exhibited an almost 80% rate of cell death. FIG. 5A is a vector map and FIG. 5B is a combined graph showing the effects of the test constructs and various controls in the HepG2 cells and HepAD38 cells to highlight the drastic cell death in the HepAD38 cells infected with the AAV8-HBV-DRS1 (EF1a>HBV-rcCasp9) construct.

Example 3

Figure 6B:
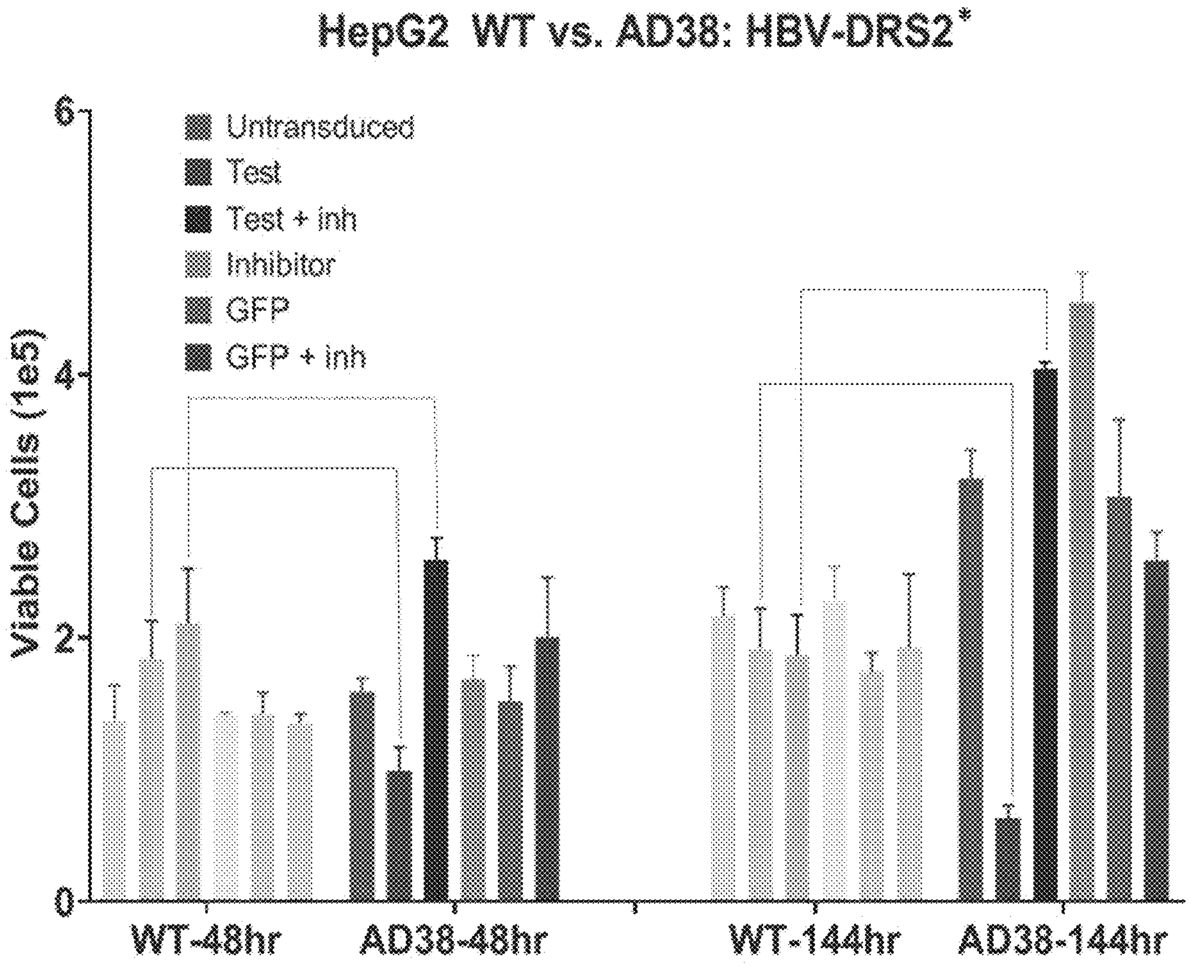

Finally, in Experiment 3, the AAV8-HBV-DRS2 (TBG>HBV-rcCasp9) construct was tested. This construct contains a liver-specific promoter, thyroxine binding globulin (TBG). The results from these experiments illustrate the viral specific cell death in the Group 2 HepAD38 cells, which exhibited an almost 80% rate of cell death (FIG. 6A and FIG. 6B). In this grouping, the Group 1 cells were untransduced, the Group 2 cells were the test cells transduced with AAV8-HBV-DRS2 (TBG>HBV-rcCasp9); the Group 3 cells were the same with the addition of the Casp9 inhibitor z-LEHD.fmk; the Group 4 cells were contacted with only the Casp9 inhibitor z-LEHD.fmk as a control; the Group 5 cells were transduced with a construct containing GFP to further track the construct expression; the Group 6 cells were transduced with the same GFP construct and also incubated with the Casp9 inhibitor z-LEHD.fmk.

The test vector+Casp9 Inhibitor control groups in Experiments 2-3 illustrated that the cell death is caspase-9 initiated, and not from vector/DNA toxicity.

The GFP-AAV control groups in Experiments 2-3 illustrated that the cell death was not due to AAV toxicity.

Example 4

In experiment 4, HBV-infected or HBV producing cells were treated with HBV RNA as provided herein, and mean percent cell death was calculated based on cell viability. By day 4, mean cell death in a variety of HBV-producing cells was 92% (ranging 88.6% to 95.8%). No significant cell death was observed in uninfected cells. RT and pan-caspase inhibitors individually prevented cell death in AAV-treated infected cells. These results show that HBV RNA construct selectively kills HBV-infected or producing cells.

Example 5

In Vivo Mouse Hepatitis Model Experiments

Figure 9:
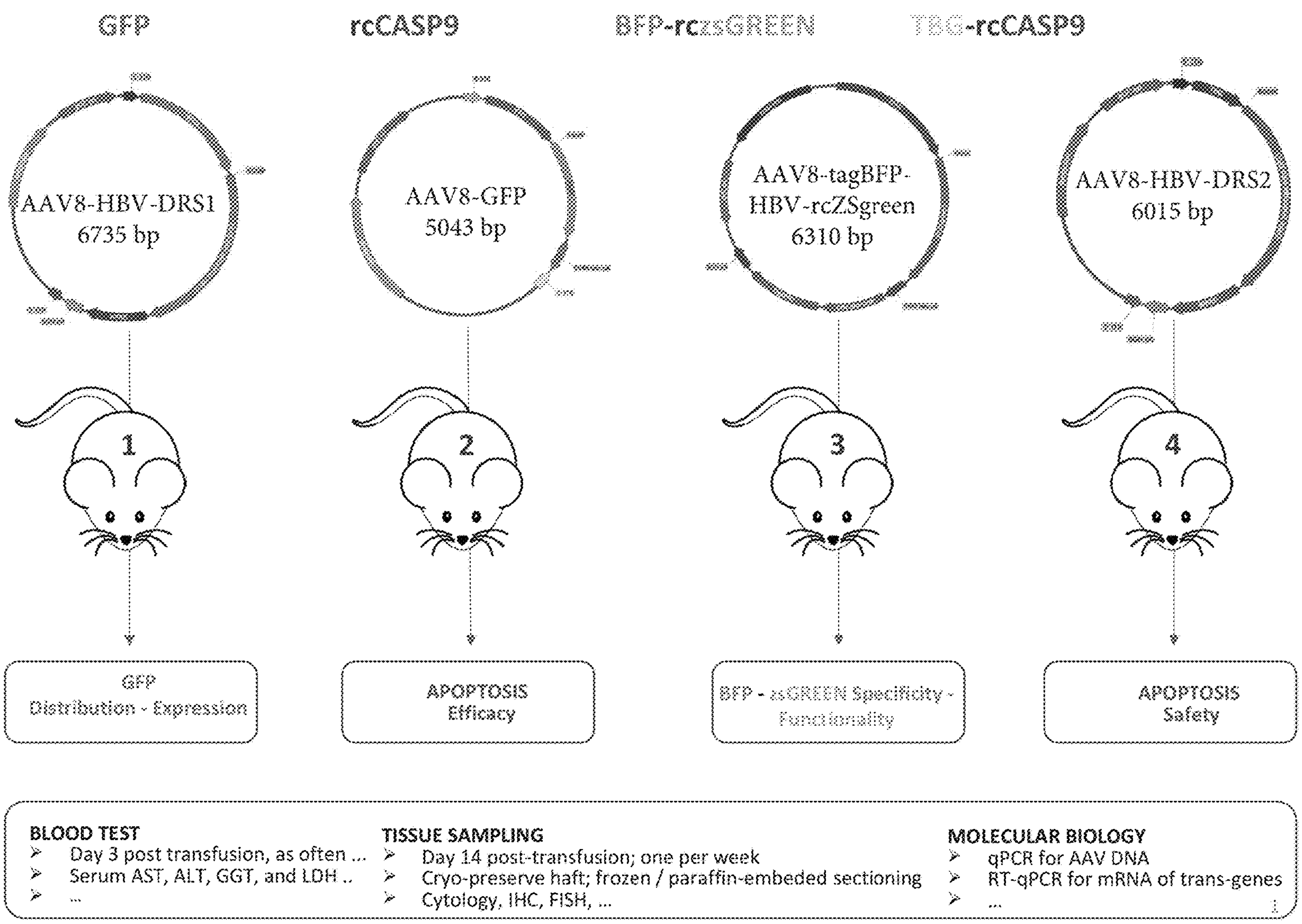
FIG. 9 is a schematic illustrating the in vivo testing utilizing model mice to evaluate distribution, efficacy, specificity/functionality, and safety of the targeted recombinant constructs.

These constructs were further tested in an in vivo mouse model, and the results illustrate the viral specific cell death for the test constructs AAV8-HBV-DRS1 (EF1a>HBV-rc-Casp9) and AAV8-HBV-DRS2 (TBG>HBV-rcCasp9) (FIG. 9).

In the above section, results from a novel in vitro proof-of-concept to co-opt the Hepatitis B Virus (HBV) polymerase (pol) to induce apoptosis of infected hepatocytes have been shown. An HBV transgenic mouse model was also used to evaluate in vivo the efficacy and specificity of the mechanism of these constructs and approach.

Methods

AAV particles were packaged with a proprietary vector construct that expresses a non-functional non-coding (nc) RNA flanked between sequences specific to the reverse transcriptase (RT) domain of HBV pol (HBV pol/RT). The ncRNA would be recognized by HBV pol/RT and get reversely transcribed into double-stranded (ds)DNA which is encoded to overexpress caspase-9 (casp-9) (FIG. 1A and FIG. 1B). HBV transgenic mice, five per group, were injected with AAV particles expressing vectors under EF1a or liver-specific thyroxine binding globulin (TBG) promoter, a GFP vector or placebo. Peripheral blood was monitored weekly for liver enzymes and HBeAg. Heart, lungs, kidneys and liver were harvested on days 14 or 28 and evaluated for tissue distribution of AAV VP by IHC and Western Blot. Casp-9, caspase cleavage products and double staining of HBV core proteins with casp-9 were also evaluated by IHC. In addition, HBV pol-expressing or non-expressing HepG2-Red-Fluc cells were implanted into the liver of nude mice with matrigel to facilitate local tumor growth. Mice were then treated with AAVs expressing the test vector. At various time points, mice were injected with D-Luciferin substrate to quantify the changes in tumor size using the IVIS Lumina S5 Imaging System.

Results

Organs harvested from transgenic mice on day 14 post-treatment showed significant casp-9 expression in liver and kidney cells expressing HBV but not in those not expressing HBV. Kidney tissues of mice treated with the vector carrying TBG promoter had no increased casp-9 expression compared to untreated and GFP controls. Moreover, cells in other organs that were stained positive for treatment AAV particles exhibited no casp-9 overexpression. Livers harvested on day 28 post-treatment showed diffuse apoptotic neutrophil-infiltrated areas in treatment groups but not in controls (FIG. 11A). At week 4 in treatment groups, ALT level increased 1.8-2.2-fold and AST levels increased 1.4-fold compared to GFP-AAV and placebo controls. (FIG. 11B). There were no significant changes in peripheral HBeAg. The results of the nude mice xenotransplantation cure study will be evaluated.

Conclusions

Figure 11C:
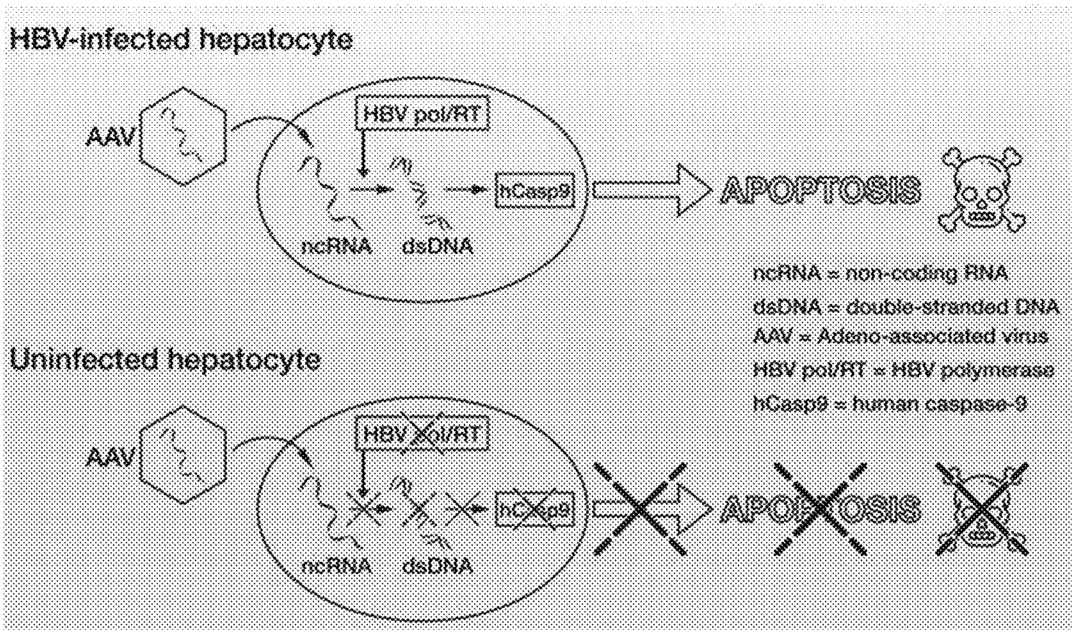

A novel AAV vector to hijack HBV pol specifically induced overexpression of Casp-9 and apoptosis in HBV-expressing cells in vitro and in vivo. A schematic showing an overview of this process is shown in FIG. 11C. The lack of decrease in peripheral HBeAg was expected because regenerating liver tissue in transgenic mice constitutively express the antigen. These data suggest a potentially new pathway to treat or cure HBV infection.

Sequences

```
SEQ ID NO: 1: HBV RNA Polymerase Epsilon Signal
UGUUCAUGUCCUACUGUUCAAGCCUCCAAGCUGUGCCUUGGGUGGCUUUGGGGCAUGGACA

SEQ ID NO: 2: EFS Promoter
GGCTCCGGTGCCCGTCAGTGGGCAGAGCGCACATCGCCCACAGTCCCCGAGAAGTTGGGGGGAGGGGTCGG
CAATTGATCCGGTGCCTAGAGAAGGTGGCGCGGGGTAAACTGGGAAAGTGATGTCGTGTACTGGCTCCGCC
TTTTTCCCGAGGGTGGGGGAGAACCGTATATAAGTGCAGTAGTCGCCGTGAACGTTCTTTTTCGCAACGGG
TTTGCCGCCAGAACACAGG

SEQ ID NO: 3: Caspase 9 (Casp9) Human ORF
ATGGACGAAGCGGATCGGCGGCTCCTGCGGCGGTGCCGGCTGCGGCTGGTGGAAGAGCTGCAGGTGGACCA
GCTCTGGGACGCCCTGCTGAGCCGCGAGCTGTTCAGGCCCCATATGATCGAGGACATCCAGCGGGCAGGCT
CTGGATCTCGGCGGGATCAGGCCAGGCAGCTGATCATAGATCTGGAGACTCGAGGGAGTCAGGCTCTTCCT
TTGTTCATCTCCTGCTTAGAGGACACAGGCCAGGACATGCTGGCTTCGTTTCTGCGAACTAACAGGCAAGC
AGCAAAGTTGTCGAAGCCAACCCTAGAAAACCTTACCCCAGTGGTGCTCAGACCAGAGATTCGCAAACCAG
AGGTTCTCAGACCGGAAACACCCAGACCAGTGGACATTGGTTCTGGAGGATTTGGTGATGTCGGTGCTCTT
GAGAGTTTGAGGGGAAATGCAGATTTGGCTTACATCCTGAGCATGGAGCCCTGTGGCCACTGCCTCATTAT
CAACAATGTGAACTTCTGCCGTGAGTCCGGGCTCCGCACCCGCACTGGCTCCAACATCGACTGTGAGAAGT
TGCGGCGTCGCTTCTCCTCGCTGCATTTCATGGTGGAGGTGAAGGGCGACCTGACTGCCAAGAAAATGGTG
CTGGCTTTGCTGGAGCTGGCGCAGCAGGACCACGGTGCTCTGGACTGCTGCGTGGTGGTCATTCTCTCTCA
CGGCTGTCAGGCCAGCCACCTGCAGTTCCCAGGGGCTGTCTACGGCACAGATGGATGCCCTGTGTCGGTCG
AGAAGATTGTGAACATCTTCAATGGGACCAGCTGCCCCAGCCTGGGAGGGAAGCCCAAGCTCTTTTTCATC
CAGGCCTGTGGTGGGGAGCAGAAAGACCATGGGTTTGAGGTGGCCTCCACTTCCCCTGAAGACGAGTCCCC
TGGCAGTAACCCCGAGCCAGATGCCACCCCGTTCCAGGAAGGTTTGAGGACCTTCGACCAGCTGGACGCCA
TATCTAGTTTGCCCACACCCAGTGACATCTTTGTGTCCTACTCTACTTTCCCAGGTTTTGTTTCCTGGAGG
GACCCCAAGAGTGGCTCCTGGTACGTTGAGACCCTGGACGACATCTTTGAGCAGTGGGCTCACTCTGAAGA
CCTGCAGTCCCTCCTGCTTAGGGTCGCTAATGCTGTTTCGGTGAAAGGGATTTATAAACAGATGCCTGGTT
GCTTTAATTTCCTCCGGAAAAAACTTTTCTTTAAAACATCATAA

SEQ ID NO: 4: Reverse Complement of Casp9
TTATGATGTTTTAAAGAAAAGTTTTTTCCGGAGGAAATTAAAGCAACCAGGCATCTGTTTATAAATCCCTT
TCACCGAAACAGCATTAGCGACCCTAAGCAGGAGGGACTGCAGGTCTTCAGAGTGAGCCCACTGCTCAAAG
ATGTCGTCCAGGGTCTCAACGTACCAGGAGCCACTCTTGGGGTCCCTCCAGGAAACAAAACCTGGGAAAGT
AGAGTAGGACACAAAGATGTCACTGGGTGTGGGCAAACTAGATATGGCGTCCAGCTGGTCGAAGGTCCTCA
```

-continued

AACCTTCCTGGAACGGGGTGGCATCTGGCTCGGGGTTACTGCCAGGGGACTCGTCTTCAGGGGAAGTGGAG
GCCACCTCAAACCCATGGTCTTTCTGCTCCCCACCACAGGCCTGGATGAAAAAGAGCTTGGGCTTCCCTCC
CAGGCTGGGGCAGCTGGTCCCATTGAAGATGTTCACAATCTTCTCGACCGACACAGGGCATCCATCTGTGC
CGTAGACAGCCCCTGGGAACTGCAGGTGGCTGGCCTGACAGCCGTGAGAGAGAATGACCACCACGCAGCAG
TCCAGAGCACCGTGGTCCTGCTGCGCCAGCTCCAGCAAAGCCAGCACCATTTTCTTGGCAGTCAGGTCGCC
CTTCACCTCCACCATGAAATGCAGCGAGGAGAAGCGACGCCGCAACTTCTCACAGTCGATGTTGGAGCCAG
TGCGGGTGCGGAGCCCGGACTCACGGCAGAAGTTCACATTGTTGATAATGAGGCAGTGGCCACAGGGCTCC
ATGCTCAGGATGTAAGCCAAATCTGCATTTCCCCTCAAACTCTCAAGAGCACCGACATCACCAAATCCTCC
AGAACCAATGTCCACTGGTCTGGGTGTTTCCGGTCTGAGAACCTCTGGTTTGCGAATCTCTGGTCTGAGCA
CCACTGGGGTAAGGTTTTCTAGGGTTGGCTTCGACAACTTTGCTGCTTGCCTGTTAGTTCGCAGAAACGAA
GCCAGCATGTCCTGGCCTGTGTCCTCTAAGCAGGAGATGAACAAAGGAAGAGCCTGACTCCCTCGAGTCTC
CAGATCTATGATCAGCTGCCTGGCCTGATCCCGCCGAGATCCAGAGCCTGCCCGCTGGATGTCCTCGATCA
TATGGGGCCTGAACAGCTCGCGGCTCAGCAGGGCGTCCCAGAGCTGGTCCACCTGCAGCTCTTCCACCAGC
CGCAGCCGGCACCGCCGCAGGAGCCGCCGATCCGCTTCGTCCAT

SEQ ID NO: 5: Reverse complement of EFS promoter
CCTGTGTTCTGGCGGCAAACCCGTTGCGAAAAAGAACGTTCACGGCGACTACTGCACTTATATACGGTTCT
CCCCCACCCTCGGGAAAAAGGCGGAGCCAGTACACGACATCACTTTCCCAGTTTACCCCGCGCCACCTTCT
CTAGGCACCGGATCAATTGCCGACCCCTCCCCCCAACTTCTCGGGGACTGTGGGCGATGTGCGCTCTGCCC
ACTGACGGGCACCGGAGCC SEQ ID NO: 6: SV40 polyA
ACTTGTTTATTGCAGCTTATAATGGTTACAAATAAAGCAATAGCATCACAAATTTCACAAATAAAGCATTT
TTTTCACTGCATTCTAGTTGTGGTTTGTCCAAACTCATCAATGTATCTTATCATGTCTGGCTCT SEQ ID NO: 7: Reverse complement of SV40 polyA
AGAGCCAGACATGATAAGATACATTGATGAGTTTGGACAAACCACAACTAGAATGCAGTGAAAAAAATGCT
TTATTTGTGAAATTTGTGATGCTATTGCTTTATTTGTAACCATTATAAGCTGCAATAAACAAGT SEQ ID NO: 8: Construct (transcript): (1746 bp)
ATGTGTTCATGTCCTACTGTTCAAGCCTCCAAGCTGTGCCTTGGGTGGCTTTGGGGCATGGACAAGAGCCA
GACATGATAAGATACATTGATGAGTTTGGACAAACCACAACTAGAATGCAGTGAAAAAAATGCTTTATTTG
TGAAATTTGTGATGCTATTGCTTTATTTGTAACCATTATAAGCTGCAATAAACAAGTTTATGATGTTTTAA
AGAAAAGTTTTTTCCGGAGGAAATTAAAGCAACCAGGCATCTGTTTATAAATCCCTTTCACCGAAACAGCA
TTAGCGACCCTAAGCAGGAGGGACTGCAGGTCTTCAGAGTGAGCCCACTGCTCAAAGATGTCGTCCAGGGT
CTCAACGTACCAGGAGCCACTCTTGGGGTCCCTCCAGGAAACAAAACCTGGGAAAGTAGAGTAGGACACAA
AGATGTCACTGGGTGTGGGCAAACTAGATATGGCGTCCAGCTGGTCGAAGGTCCTCAAACCTTCCTGGAAC
GGGGTGGCATCTGGCTCGGGGTTACTGCCAGGGGACTCGTCTTCAGGGGAAGTGGAGGCCACCTCAAACCC
ATGGTCTTTCTGCTCCCCACCACAGGCCTGGATGAAAAAGAGCTTGGGCTTCCCTCCCAGGCTGGGGCAGC
TGGTCCCATTGAAGATGTTCACAATCTTCTCGACCGACACAGGGCATCCATCTGTGCCGTAGACAGCCCCT
GGGAACTGCAGGTGGCTGGCCTGACAGCCGTGAGAGAGAATGACCACCACGCAGCAGTCCAGAGCACCGTG
GTCCTGCTGCGCCAGCTCCAGCAAAGCCAGCACCATTTTCTTGGCAGTCAGGTCGCCCTTCACCTCCACCA
TGAAATGCAGCGAGGAGAAGCGACGCCGCAACTTCTCACAGTCGATGTTGGAGCCAGTGCGGGTGCGGAGC
CCGGACTCACGGCAGAAGTTCACATTGTTGATAATGAGGCAGTGGCCACAGGGCTCCATGCTCAGGATGTA
AGCCAAATCTGCATTTCCCCTCAAACTCTCAAGAGCACCGACATCACCAAATCCTCCAGAACCAATGTCCA
CTGGTCTGGGTGTTTCCGGTCTGAGAACCTCTGGTTTGCGAATCTCTGGTCTGAGCACCACTGGGGTAAGG
TTTTCTAGGGTTGGCTTCGACAACTTTGCTGCTTGCCTGTTAGTTCGCAGAAACGAAGCCAGCATGTCCTG
GCCTGTGTCCTCTAAGCAGGAGATGAACAAAGGAAGAGCCTGACTCCCTCGAGTCTCCAGATCTATGATCA
GCTGCCTGGCCTGATCCCGCCGAGATCCAGAGCCTGCCCGCTGGATGTCCTCGATCATATGGGGCCTGAAC
AGCTCGCGGCTCAGCAGGGCGTCCCAGAGCTGGTCCACCTGCAGCTCTTCCACCAGCCGCAGCCGGCACCG
CCGCAGGAGCCGCCGATCCGCTTCGTCCATCCTGTGTTCTGGCGGCAAACCCGTTGCGAAAAAGAACGTTC
ACGGCGACTACTGCACTTATATACGGTTCTCCCCCACCCTCGGGAAAAAGGCGGAGCCAGTACACGACATC
ACTTTCCCAGTTTACCCCGCGCCACCTTCTCTAGGCACCGGATCAATTGCCGACCCCTCCCCCCAACTTCT
CGGGGACTGTGGGCGATGTGCGCTCTGCCCACTGACGGGCACCGGAGCCTGTTCATGTCCTACTGTTCAAG
CCTCCAAGCTGTGCCTTGGGTGGCTTTGGGGCATGGACATAA Reverse Complement sequence of "EFS promoter driving zsGreen gene" flanked between HBV epsilon signals:

SEQ ID NO:9

ATGTGTTCATGTCCTACTGTTCAAGCCTCCAAGCTGTGCCTTGGGTGGCTTTGGGGCATGGACAAGAGCCA
GACATGATAAGATACATTGATGAGTTTGGACAAACCACAACTAGAATGCAGTGAAAAAAATGCTTTATTTG
TGAAATTTGTGATGCTATTGCTTTATTTGTAACCATTATAAGCTGCAATAAACAAGTTTAGGGCAAGGCGG
AGCCGGAGGCGATGGCGTGCTCGGTCAGGTGCCACTTCTGGTTCTTGGCGTCGCTGCGGTCCTCGCGGGTC
AGCTTGTGCTGGATGAAGTGCCAGTCGGGCATCTTGCGGGGCACGGACTTGGCCTTGTACACGGTGTCGAA
CTGGCAGCGCAAGCGGCCACCGTCCTTCAGCAGCAGGTACATGCTCACGTCGCCCTTCAAGATGCCCTGCT
TGGGCACGGGGATGATCTTCTCGCAGGAGGGCTCCCAGTTGTCGGTCATCTTCTTCATCACGGGGCCGTCG
GCGGGGAAGTTCACGCCGTAGAACTTGGACTCGTGGTACATGCAGTTCTCCTCCACGCTCACGGTGATGTC
GGCGTTGCAGATGCACACGGCGCCGTCCTCGAACAGGAAGGAGCGGTCCCAGGTGTAGCCGGCGGGGCAGG
AGTTCTTGAAGTAGTCGACGATGTCCTGGGGGTACTCGGTGAACACGCGGTTGCCGTACATGAAGGCGGCG
GACAAGATGTCCTCGGCGAAGGGCAAGGGGCCGCCCTCCACCACGCACAGGTTGATGGCCTGCTTGCCCTT
GAAGGGGTAGCCGATGCCCTCGCCGGTGATCACGAACTTGTGGCCGTCCACGCAGCCCTCCATGCGGTACT
TCATGGTCATCTCCTTGGTCAGGCCGTGCTTGGACTGGGCCATCCTGTGTTCTGGCGGCAAACCCGTTGCG
AAAAAGAACGTTCACGGCGACTACTGCACTTATATACGGTTCTCCCCCACCCTCGGGAAAAAGGCGGAGCC
AGTACACGACATCACTTTCCCAGTTTACCCCGCGCCACCTTCTCTAGGCACCGGATCAATTGCCGACCCCT
CCCCCCAACTTCTCGGGGACTGTGGGCGATGTGCGCTCTGCCCACTGACGGGCACCGGAGCCTGTTCATGT
CCTACTGTTCAAGCCTCCAAGCTGTGCCTTGGGTGGCTTTGGGGCATGGACATAA

Example 6

Influenza-Specific Casp9 Construct and Experiments

Figure 10A:
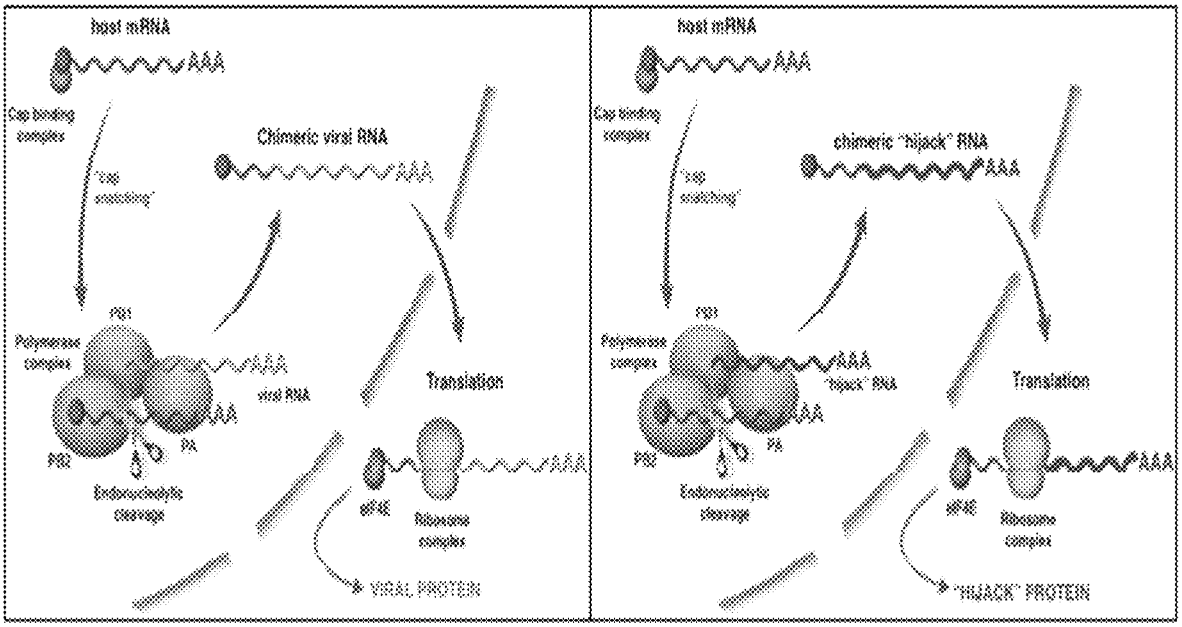
FIG. 10A and FIG. 10B are a schematic and a graph showing how the "influenza hijack/suicide vectors" hijack the viral machinery to induce apoptosis in infected cells (FIG. 10A), and in vitro results showing that the test constructs delivered in trans to engage with influenza polymerase hijacks the viral machinery to induce cell death in influenza infected cells 40% more rapidly than untreated infected cells (FIG. 10B).
Figure 10B:
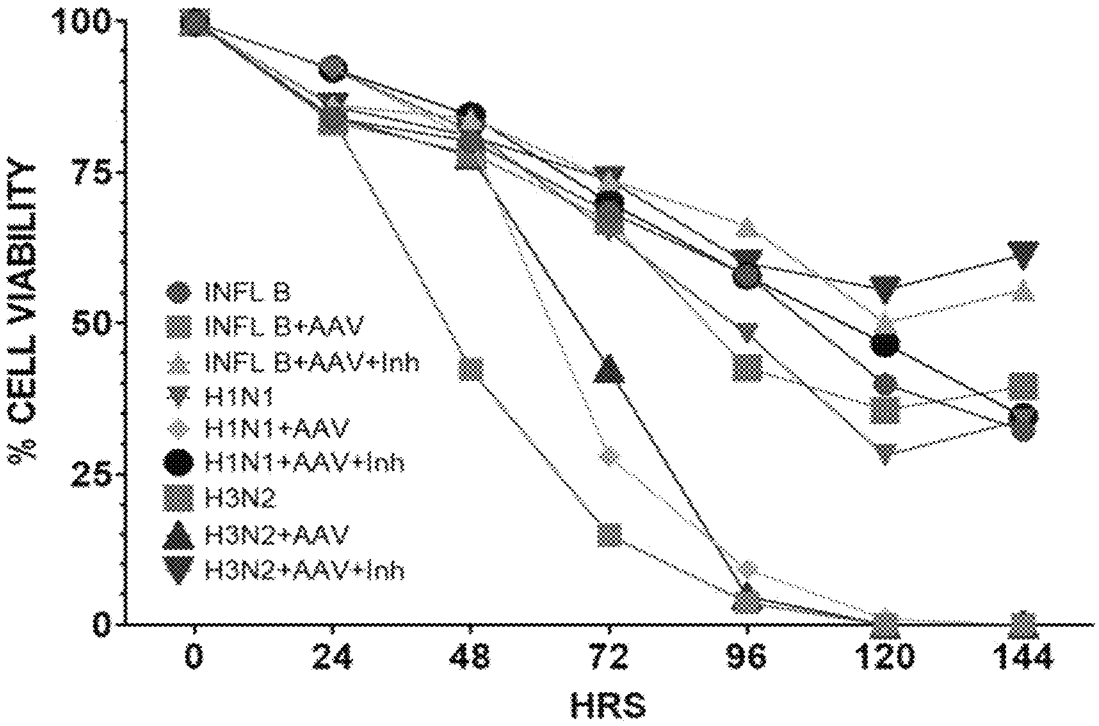

The following sequences and constructs will be utilized to test constructs designed to treat influenza viruses. Because influenza virus is a single-stranded negative-sense RNA virus that utilizes influenza polymerase complex to express viral proteins or replicate its viral genome, a vector construct expressing a negative-sense non-coding (nc)RNA has been designed to engage with influenza polymerase (in a similar manner to the ones designed specifically for HBV as described in Examples 1-4). The ncRNA "hijacks" the virus machinery to induce apoptosis specifically in infected cells, which is a potential anti-viral treatment (FIG. 10A and FIG. 10B).

Methods

Adeno-associated virus (AAV) was packaged with a novel vector expressing ncRNA, (which can be thought of as influenza "hijack RNA", or an RNA suicide vector for influenza infected cells), that transcribes the reverse complementary strand of zsGreen marker (AAV.infv.rcZsGreen) or caspase-9 (casp9) gene (AAV.infv.rcCasp9) between influenza genomic RNA non-coding sequence (NCS) regions that are highly conserved across several influenza virus strains. Embodiments of these sequences are shown below as SEQ ID NOs 10-24. Madin-Darby Canine Kidney (MDCK) cells were infected with influenza A H1N1 or H3N2, or influenza B virus at 0.1 MOI, as an in vitro system to test these influenza (nc)RNA constructs. Influenza infected and uninfected MDCK cells were transduced with AAV.infv.rcZsGreen vector, and with AAV.infv.rcCasp9 in the presence and absence of casp9 inhibitor Z-LEHD-FMK to determine the functionality of the hijack vector, or RNA suicide vector for influenza infected cells. Flow cytometry was used to determine zsGreen expression. Cell viability and proliferation were evaluated daily by FACS, Annexin assay, and automated cell count.

Results

All AAV.infv.rcZsGreen vector transduced influenza-infected cells successfully produced zsGreen protein, confirming that the hijack/suicide RNA constructs were recognized and transcribed by the polymerase complex in each influenza strain. Influenza infection killed 60%-68% of the untreated cells by day 6. 91%-95% of infected cells treated with casp9 hijack/suicide vector at 24 h post-influenza infection died on day 3 post-treatment. Casp-9 inhibition in the culture salvaged vector induced cell death and extended the lifespan of infected cells to 5-6 days (FIG. 10B). There was no significant cell death in uninfected control groups.

Conclusions

A vector delivered in trans to engage with influenza polymerase hijacks the virus machinery to induce death in influenza infected cells 40% more rapidly than untreated infected cells. This effect was seen across viral strains, likely due to conserved nature of influenza polymerase. This novel approach could be used to develop an effective treatment for influenza.

Sequences

SEQ ID NO: 10
3' Non-Coding Region of the Vector
5' CCTGCTTTTGCT 3'

SEQ ID NO: 11
5' Non-Coding Region of the Vector
5' AGTAGAAACAAGG 3'

Influenza-specific Casp9 Vector

SEQ ID NO: 12
AGTAGAAACAAGGGTGTTTTTTATCATTATGATGTTTTAAAGAAAAGTT
TTTTCCGGAGGAAATTAAAGCAACCAGGCATCTGTTTATAAATCCCTTT
CACCGAAACAGCATTAGCGACCCTAAGCAGGAGGGACTGCAGGTCTTCA
GAGTGAGCCCACTGCTCAAAGATGTCGTCCAGGGTCTCAACGTACCAGG
AGCCACTCTTGGGGTCCCTCCAGGAAACAAAACCTGGGAAAGTAGAGTA
GGACACAAAGATGTCACTGGGTGTGGGCAAACTAGATATGGCGTCCAGC
TGGTCGAAGGTCCTCAAACCTTCCTGGAACGGGGTGGCATCTGGCTCGG
GGTTACTGCCAGGGGACTCGTCTTCAGGGGAAGTGGAGGCCACCTCAAA
CCCATGGTCTTTCTGCTCCCCACCACAGGCCTGGATGAAAAAGAGCTTG
GGCTTCCCTCCCAGGCTGGGGCAGCTGGTCCCATTGAAGATGTTCACAA
TCTTCTCGACCGACACAGGGCATCCATCTGTGCCGTAGACAGCCCCTGG
GAACTGCAGGTGGCTGGCCTGACAGCCGTGAGAGAGAATGACCACCACG
CAGCAGTCCAGAGCACCGTGGTCCTGCTGCGCCAGCTCCAGCAAAGCCA
GCACCATTTTCTTGGCAGTCAGGTCGCCCTTCACCTCCACCATGAAATG
CAGCGAGGAGAAGCGACGCCGCAACTTCTCACAGTCGATGTTGGAGCCA
GTGCGGGTGCGGAGCCCGGACTCACGGCAGAAGTTCACATTGTTGATAA
TGAGGCAGTGGCCACAGGGCTCCATGCTCAGGATGTAAGCCAAATCTGC
ATTTCCCCTCAAACTCTCAAGAGCACCGACATCACCAAATCCTCCAGAA
CCAATGTCCACTGGTCTGGGTGTTTCCGGTCTGAGAACCTCTGGTTTGC
GAATCTCTGGTCTGAGCACCACTGGGGTAAGGTTTTCTAGGGTTGGCTT
CGACAACTTTGCTGCTTGCCTGTTAGITCGCAGAAACGAAGCCAGCATG
TCCTGGCCTGTGTCCTCTAAGCAGGAGATGAACAAAGGAAGAGCCTGAC
TCCCTCGAGTCTCCAGATCTATGATCAGCTGCCTGGCCTGATCCCGCCG
AGATCCAGAGCCTGCCCGCTGGATGTCCTCGATCATATGGGGCCTGAAC
AGCTCGCGGCTCAGCAGGGCGTCCCAGAGCTGGTCCACCTGCAGCTCTT
CCACCAGCCGCAGCCGGCACCGCCGCAGGAGCCGCCGATCCGCTTCGTC
CATTCCCCTGCTTTTGCT

Key Features 5':
  SEQ ID NO: 13: 5' non-coding region of the vector: AGTAGAAACAAGG SEQ ID NO: 14: Non-specific buffer sequence GTG SEQ ID NO: 15: $U_{5-7}$ repeat that will be "stuttered" into PolyA signal during reverse transcription: TTTTTT SEQ ID NO: 16: Non-specific buffer sequence, most common across influenza species: ATCA SEQ ID NO: 17: Stop codon of the "final+sense Casp9 transcript": TTA Key Features 3':
  SEQ ID NO: 18: Start codon of the "final+sense Casp9 transcript": CAT SEQ ID NO: 19: Non-specific buffer sequence: TCC SEQ ID NO: 20: 3' non-coding region of the vector: CCTGCTTTTGCT (-)ssRNA transcript for Influenza polymerase complex recognition and reverse transcription (transcript expressed by the test vector)

SEQ ID NO: 21

```
AGUAGAAACAAGGGUGUUUUUUAUCAUUAUGAUGUUUUAAAGAAAAGUU

UUUUCCGGAGGAAAUUAAAGCAACCAGGCAUCUGUUUAUAAAUCCCUUU

CACCGAAACAGCAUUAGCGACCCUAAGCAGGAGGGACUGCAGGUCUUCA

GAGUGAGCCCACUGCUCAAAGAUGUCGUCCAGGGUCUCAACGUACCAGG

AGCCACUCUUGGGGUCCCUCCAGGAAACAAAACCUGGGAAAGUAGAGUA

GGACACAAAGAUGUCACUGGGUGUGGGCAAACUAGAUAUGGCGUCCAGC

UGGUCGAAGGUCCUCAAACCUUCCUGGAACGGGGUGGCAUCUGGCUCGG

GGUUACUGCCAGGGGACUCGUCUUCAGGGGAAGUGGAGGCCACCUCAAA

CCCAUGGUCUUUCUGCUCCCCACCACAGGCCUGGAUGAAAAAGAGCUUG

GGCUUCCCUCCCAGGCUGGGGCAGCUGGUCCCAUUGAAGAUGUUCACAA

UCUUCUCGACCGACACAGGGCAUCCAUCUGUGCCGUAGACAGCCCCUGG

GAACUGCAGGUGGCUGGCCUGACAGCCGUGAGAGAGAAUGACCACCACG

CAGCAGUCCAGAGCACCGUGGUCCUGCUGCGCCAGCUCCAGCAAAGCCA

GCACCAUUUUCUUGGCAGUCAGGUCGCCCUUCACCUCCACCAUGAAAUG

CAGCGAGGAGAAGCGACGCCGCAACUUCUCACAGUCGAUGUUGGAGCCA

GUGCGGGUGCGGAGCCCGGACUCACGGCAGAAGUUCACAUUGUUGAUAA

UGAGGCAGUGGCCACAGGGCUCCAUGCUCAGGAUGUAAGCCAAAUCUGC

AUUUCCCCUCAAACUCUCAAGAGCACCGACAUCACCAAAUCCUCCAGAA

CCAAUGUCCACUGGUCUGGGUGUUUCCGGUCUGAGAACCUCUGGUUUGC

GAAUCUCUGGUCUGAGCACCACUGGGGUAAGGUUUUCUAGGGUUGGCUU

CGACAACUUUGCUGCUUGCCUGUUAGUUCGCAGAAACGAAGCCAGCAUG

UCCUGGCCUGUGUCCUCUAAGCAGGAGAUGAACAAAGGAAGAGCCUGAC

UCCCUCGAGUCUCCAGAUCUAUGAUCAGCUGCCUGGCCUGAUCCCGCCG

AGAUCCAGAGCCUGCCCGCUGGAUGUCCUCGAUCAUAUGGGGCCUGAAC

AGCUCGCGGCUCAGCAGGGCGUCCCAGAGCUGGUCCACCUGCAGCUCUU

CCACCAGCCGCAGCCGGCACCGCCGCAGGAGCCGCCGAUCCGCUUCGUC

CAUUCCCCUGCUUUUGCU
```

General Vector Structure

In some embodiments, the general vector structure has the following formula:

SEQ ID NO: 22-ORF-SEQ ID NO: 23, wherein

SEQ ID NO: 22 is AGTAGAAACAAGGGTGTTTTTTATCATTA;

ORF is any protein coding sequence; and

SEQ ID NO: 23 is CATTCCCCTGCTTTTGCT.

GFP marker construct (in place of Casp9) for experimental detection

SEQ ID NO:24

```
AGTAGAAACAAGGGTGTTTTTTATCATTACTTGTACAGCTCGTCCATGC

CGAGAGTGATCCCGGCGGCGGTCACGAACTCCAGCAGGACCATGTGATC

GCGCTTCTCGTTGGGGTCTTTGCTCAGGGCGGACTGGGTGCTCAGGTAG

TGGTTGTCGGGCAGCAGCACGGGGCCGTCGCCGATGGGGGTGTTCTGCT
```

-continued

```
GGTAGTGGTCGGCGAGCTGCACGCTGCCGTCCTCGATGTTGTGGCGGAT

CTTGAAGTTCACCTTGATGCCGTTCTTCTGCTTGTCGGCCATGATATAG

ACGTTGTGGCTGTTGTAGTTGTACTCCAGCTTGTGCCCCAGGATGTTGC

CGTCCTCCTTGAAGTCGATGCCCTTCAGCTCGATGCGGTTCACCAGGGT

GTCGCCCTCGAACTTCACCTCGGCGCGGGTCTTGTAGTTGCCGTCGTCC

TTGAAGAAGATGGTGCGCTCCTGGACGTAGCCTTCGGGCATGGCGGACT

TGAAGAAGTCGTGCTGCTTCATGTGGTCGGGGTAGCGGCTGAAGCACTG

CACGCCGTAGGTCAGGGTGGTCACGAGGGTGGGCCAGGGCACGGGCAGC

TTGCCGGTGGTGCAGATGAACTTCAGGGTCAGCTTGCCGTAGGTGGCAT

CGCCCTCGCCCTCGCCGGACACGCTGAACTTGTGGCCGTTTACGTCGCC

GTCCAGCTCGACCAGGATGGGCACCACCCCGGTGAACAGCTCCTCGCCC

TTGCTCACCATTCCCCTGCTTTTGCT
```

Example 7

In this experiment, Madin-Darby Canine Kidney (MDCK) cells were uninfected, infected with influenza A (H1N1 or H3N2) or influenza B virus. Next, the uninfected and infected cells were treated with AAV particles comprising hijack RNA coding for human casp9 or AAV particles comprising GFP. Three independent experiments, each in triplicates, were run.

Casp9 expression and its cleavage products (caspase 3 and 7) were measured via flow cytometry. Casp9 expression increased 4× with H1N1 influenza infection compared to uninfected cells. The hijack RNA AAV had no effect on uninfected cells, but when used on infected cells the "hijack" RNA AAV increased casp9 by 10× as compared to uninfected cells, and by 3× as compared to untreated infected cells.

The effectiveness of the hijack RNA AAV was measured daily by monitoring cell viability and proliferation with automated cell count and FACS analysis. Treatment of uninfected cells with the "hijack" RNA AAV produced no effect on cell viability. However, treatment of influenza B, H1N1, or H3N2 infected cells with the hijack RNA AAV increased cell viability by 120 hours as compared to untreated infected cells, or GFP AAV treated infected cells.

Infected cell percentage in the culture was monitored via influenza nucleoprotein intracellular staining using FACS analysis. Treatment with the hijack RNA AAV reduced percentage of H1N1, H3N2, or influenza B infected cells by 72 hours, and completely eradicated influenza infection by 96 hours.

These results show that the hijack RNA AAV that expresses caspase-9 effectively kills influenza infection in cell culture.

Example 8

Coronavirus Construct Design

Subgenomic (−)ssRNA synthesis from (+)ssRNA through CoV polymerase (RNA-dependent RNA-polymerase or RdRp). The coronaviral RdRp pauses at intergenic template-switching donor signals and is transferred by a copy-choice mechanism to a highly similar acceptor site near the 5' end of the genome to copy the 5'-terminal leader. The transcription regulation sequences (TRS) function as template-switching signal. TRS is 5'ACGAAC3' (SEQ ID NO: 31) on positive strand and 3'UGCUUG5' (SEQ ID NO: 32) on negative strand. If the subgnomic mRNA (sgmRNA) still has multiple TRS in it, RdRp sees the new smRNA as a small genome, initiates negative strand synthesis on it, and switches template at an internal donor signal to make a negative strand template to synthesize a shorter internally nested sgmRNA. The leader RNA (60-80 nt) sequence always stays on the 3' end of the subgenomic negative strand and 5' end of the subgenomic mRNA.

Figure 12A:
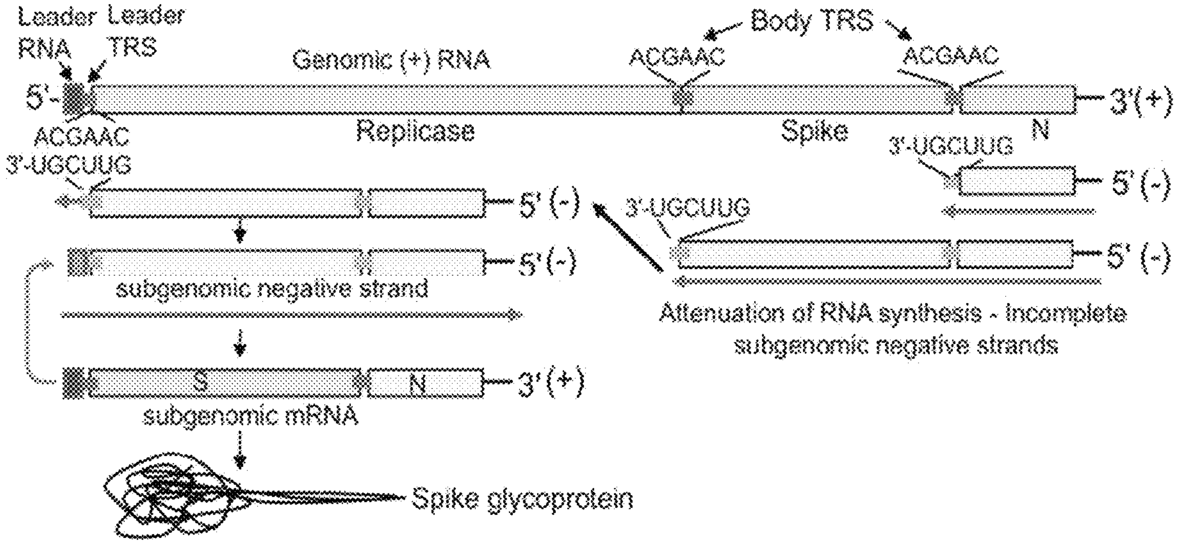
FIG. 12A and FIG. 12B are schematics showing the overview of design for a coronavirus "hijack-RNA" construct.
Figure 12B:
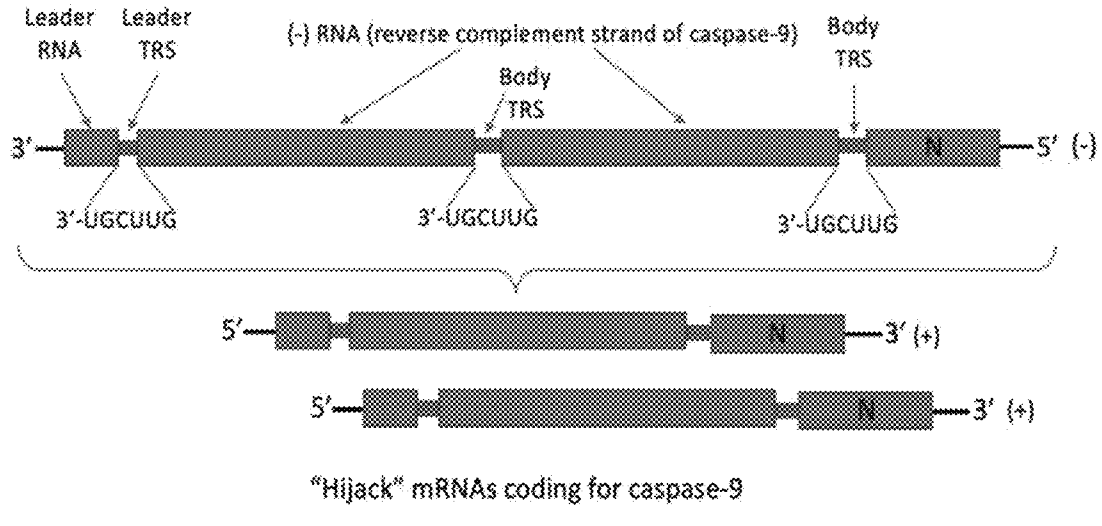

The subgenomic (−)ssRNA is an intermediate to produce new mRNAs for the viral protein synthesis. Thus, coronavirus "hijack RNAs" can be designed that are (−)ssRNA which mimic the leader RNA and TRS sequences but carry the negative strand of a gene of interest (e.g. caspase-9, for example). An overview of this strategy is shown in FIG. 12A and FIG. 12B.

Standard Methods

Standard methods in molecular biology are described Sambrook, Fritsch and Maniatis (1982 & 1989 2nd Edition, 2001 3rd Edition) Molecular Cloning, A Laboratory Manual, Cold Spring Harbor Laboratory Press, Cold Spring Harbor, NY; Sambrook and Russell (2001) Molecular Cloning, 3rd ed., Cold Spring Harbor Laboratory Press, Cold Spring Harbor, NY; Wu (1993) Recombinant DNA, Vol. 217, Academic Press, San Diego, CA). Standard methods also appear in Ausbel, et al. (2001) Current Protocols in Molecular Biology, Vols. 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) Current Protocols in Protein Science, Vol. 1, John Wiley and Sons, Inc., New York). Chemical analysis, chemical modification, post-translational modification, production of fusion proteins, glycosylation of proteins are described (see, e.g., Coligan, et al. (2000) Current Protocols in Protein Science, Vol. 2, John Wiley and Sons, Inc., New York; Ausubel, et al. (2001) Current Protocols in Molecular Biology, Vol. 3, John Wiley and Sons, Inc., NY, NY, pp. 16.0.5-16.22.17; Sigma-Aldrich, Co. (2001) Products for Life Science Research, St. Louis, MO; pp. 45-89; Amersham Pharmacia Biotech (2001) BioDirectory, Piscataway, N.J., pp. 384-391). Production, purification, and fragmentation of polyclonal and monoclonal antibodies are described (Coligan, et al. (2001) Current Protcols in Immunology, Vol. 1, John Wiley and Sons, Inc., New York; Harlow and Lane (1999) Using Antibodies, Cold Spring Harbor Laboratory Press, Cold Spring Harbor, NY; Harlow and Lane, supra). Standard techniques for characterizing ligand/receptor interactions are available (see, e.g., Coligan, et al. (2001) Current Protocols in Immunology, Vol. 4, John Wiley, Inc., New York).

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

Example 9

Figure 13:
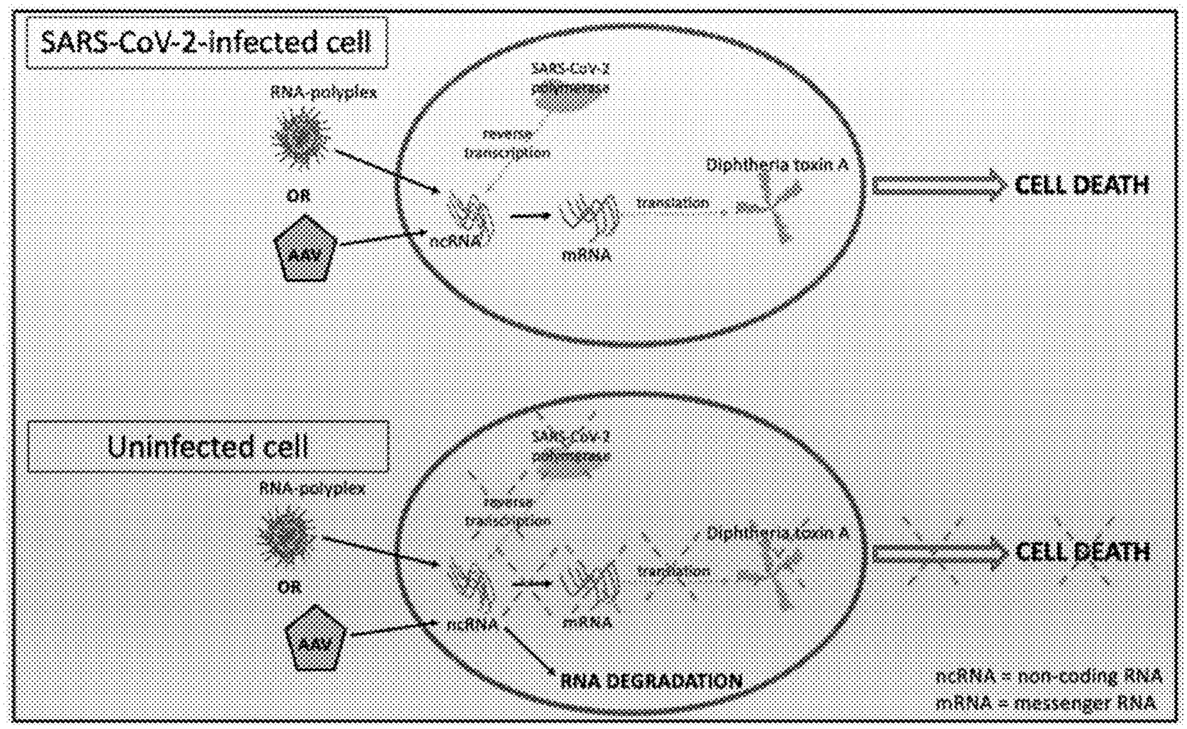
FIG. 13 illustrates a schematic showing the mechanism of action of SARS-CoV-2 hijack RNA in SARS-CoV-2-infected cells.

In this experiment, a synthetic RNA ("hijack RNA") that was designed to be recognized by SARS-CoV-2 RNA-dependent-RNA-polymerase (RdRp) was tested for its ability to eradicate SARS-CoV-2 infection in cell culture. Upon recognition, hijack RNA would be transcribed into diphtheria toxin fragment A (DT-A), to induce apoptosis specifically in infected cells, which could be a potential treatment (FIG. 13).

Methods

Adeno-associated virus (AAV) was packaged with a novel vector expressing SARS-CoV-2 hijack RNA (FIG. 15), which contains reverse complementary strand of DT-A cDNA and secondary structures of SARS-CoV-2 sgRNA. Vero cells were infected with SARS-CoV-2 USA-WA1/2020 strain at 0.1 MOI. SARS-CoV-2-infected and uninfected vero cells were transduced with test (FIG. 15) or control (GFP) AAVs. Uninfected jurkat, HEK and BHK-21 cells were also transduced with test AAV to further investigate potential off-target effects of hijack RNA in uninfected cells. Cell death and viability were evaluated daily by FACS and automated cell count. Eradication of infection in the cell cultures was established by the observation of cytopathic effects (CPE) via cell imaging and by FACS via intracellular staining of viral proteins. DT-A production in infected and uninfected cells was measured by western blot (WB) analysis of culture supernatants and cell lysates. Same experiments were repeated by transfecting the cells with in vitro transcribed hijack RNA (FIG. 14) at various (0-100 ng) concentrations. SARS-CoV-2 RdRp expressing stable vero and jurkat cell lines were also generated to assess RdRp-specific expression of the hijack RNA.

Results

Figure 16A:
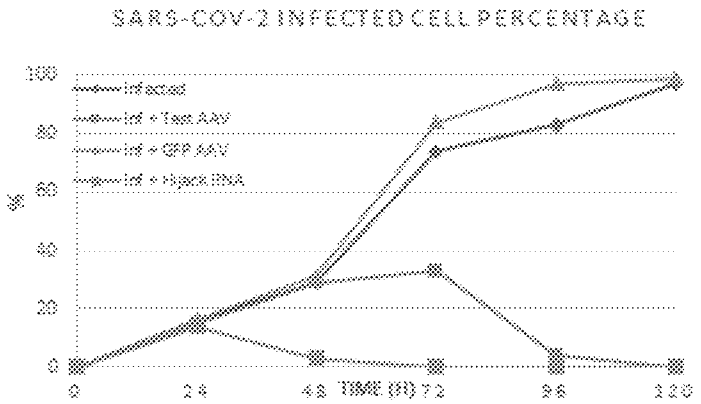
FIG. 16A and FIG. 16B are comparative graphs showing viability of SARS-CoV-2-infected or uninfected cells following treatment with test or control constructs.
Figure 16B:
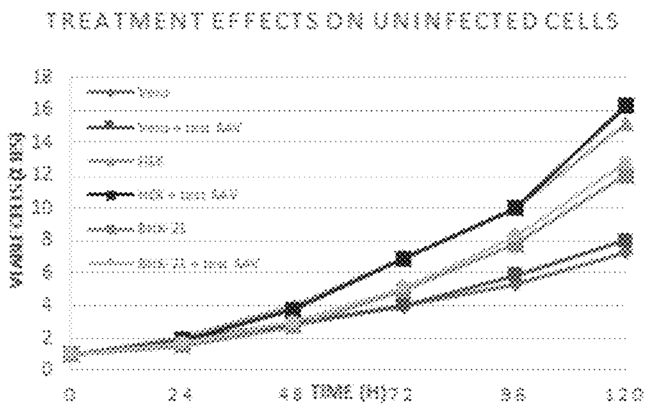

SARS-CoV-2 infection was successfully eradicated from the cultures within 48 h of test AAV transduction, confirmed by cell proliferation assays and the absence of CPE in cell imagery, as well as FACS analysis (FIG. 16A). Same results were observed within 24 h of hijack RNA transfection. Test AAV or hijack RNA had no effect on uninfected cells (FIG. 16B). Similar results were observed in RdRp expressing cell lines, confirming the hypothesized mechanism of action.

Conclusion

An RNA delivered or expressed in trans to engage with SARS-CoV-2 RdRp hijacked the virus machinery and induced rapid death in infected cells but not in uninfected cells. Hijack RNA's translation into the kill molecule DT-A was dependent on viral RdRp as demonstrated in several different cell lines, confirming specificity and sensitivity of the treatment. This novel approach could be used to develop an effective treatment to eradicate COVID-19 infection.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A recombinant nucleic acid molecule comprising:

a negative strand nucleic acid molecule or a pregenomic RNA (pgRNA) nucleic acid molecule encoding a chemokine, a cytokine, an apoptosis inducing protein, a diphtheria toxin A, a diphtheria toxin A fragment, or any combination thereof, flanked by a first viral transcription recognition signal and a second viral transcription recognition signal, wherein the negative strand nucleic acid molecule or pgRNA nucleic acid molecule is from a virus selected from the group consisting of hepatitis B virus, influenza virus and coronavirus;

a first promoter upstream (5') of the first viral transcription recognition signal and the 3' end of the negative strand nucleic acid molecule or pgRNA nucleic acid molecule, and a second promoter located between the second viral transcription recognition signal and the 5' end of the negative strand nucleic acid molecule or pgRNA nucleic acid molecule encoding a chemokine, a cytokine, an apoptosis inducing protein, a diphtheria toxin A, a diphtheria toxin A fragment, or any combination thereof, wherein (i) the first promoter and the second promoter are oriented in opposite direction and toward each other;

(ii) the second promoter and the second viral transcription recognition signal are upstream (5') of the 5' end of the negative strand nucleic acid molecule or pgRNA nucleic acid molecule;

(iii) the first and second viral transcription recognition signals are oriented in the same direction; and (iv) wherein a. if the negative strand nucleic acid molecule or pgRNA nucleic acid molecule is from a hepatitis B virus, each of the first and second viral transcription recognition signals comprises the epsilon recognition signal sequence of SEQ ID NO: 1;

b. if the negative strand nucleic acid molecule or pgRNA nucleic acid molecule is from an influenza virus, the second viral transcription recognition signal comprises the sequence of SEQ ID NO: 22 and the first viral transcription recognition signal comprises the sequence of SEQ ID NO: 23; or c. if the negative strand nucleic acid molecule or pgRNA nucleic acid molecule is from a coronavirus, each of the first and second viral transcription recognition signals comprises the sequence of SEQ ID NO: 25, SEQ ID NO: 26, SEQ ID NO: 28, or SEQ ID NO: 30.

2. The recombinant nucleic acid molecule of claim 1 further comprising a poly A tail downstream (3') of the negative strand nucleic acid molecule or pgRNA nucleic acid molecule encoding a chemokine, a cytokine, an apoptosis inducing protein, or combination thereof.

3. The recombinant nucleic acid molecule of claim 1 wherein the apoptosis inducing protein is selected from the group consisting of BAX, BID, BAK, BAD, caspase 2, caspase 8, caspase 9, caspase 10, caspase 11, caspase 12, cytochrome C, SMAC, and apoptosis-inducing factor, and any combination thereof.

4. The recombinant nucleic acid molecule of claim 1 wherein the first promoter comprises a ubiquitous promoter or a liver-tissue specific promoter, selected from the group consisting of TBG (Thyroxine Binding Globulin) promoter, albumin promoter and enhancing element, AFP (alpha-fetoprotein) promoter, AAT (Alpha-1-antitrypsin) promoter, ApoE (Apolipoprotein E) promoter and PEPCK (Phosphoenolpyruvate carboxykinase) promoter.

5. The recombinant nucleic acid molecule of claim 1 wherein the second promoter comprises elongation factor 1alpha binding sequence (EFS).

6. The recombinant nucleic acid molecule of claim 1 wherein the chemokine is selected from the group consisting of CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL8, CXCL9, CXCL10, CXCL11, CXCL12, CXCL13, CXCL14, CXCL15, CXCL16, CXCL17, XCL1, XCL2, and CX3CL1.

7. The recombinant nucleic acid molecule of claim 1 wherein the cytokine is selected from the group consisting of IL-15, IL-2, IL-8, IL-10, IL-12, IL-6, IFN-$\alpha$, IFN-, IFN-$\gamma$, TNF-a, CD40L, Mig, and Crg-2.

8. A vector comprising the recombinant nucleic acid molecule of claim 1.

9. The vector of claim 8, wherein the vector comprises a delivery vector or vehicle for delivery to a mammalian cell.

10. The vector of claim 9, wherein the delivery vector or vehicle comprises a virus-like particle (VLP), an adeno-associated virus (AAV), a liposome, a nanoparticle, a micelle, a polymeric vesicle, or a polymersome.

11. A pharmaceutical composition comprising the vector of claim 9.

12. A replication incompetent virus-like particle (VLP) comprising:

an optional translocation motif (TLM) fused to a capsid protein from a hepatitis B viral capsid or an influenza viral capsid or coronavirus fusion protein;

a negative strand nucleic acid molecule or a pregenomic RNA (pgRNA) nucleic acid molecule encoding a chemokine, a cytokine, an apoptosis inducing protein, a diphtheria toxin A, a diphtheria toxin A fragment, or any combination thereof, flanked by a first and second viral transcription recognition signals, wherein the negative strand nucleic acid molecule or pgRNA nucleic acid molecule is from a virus selected from the group consisting of hepatitis B virus, influenza virus and coronavirus;

a first promoter upstream (5') of the first viral transcription recognition signal and the 3' end of the negative strand nucleic acid molecule or pgRNA nucleic acid molecule, and a second promoter located between the second viral transcription recognition signal and the 5' end of the negative strand nucleic acid molecule or pgRNA nucleic acid molecule encoding a chemokine, a cytokine, an apoptosis inducing protein, a diphtheria toxin A, a diphtheria toxin A fragment, or any combination thereof, wherein (i) the first promoter and the second promoter are oriented in opposite direction and toward each other;

(ii) the second promoter and the second viral transcription recognition signal are upstream (5') of the 5' end of the negative strand nucleic acid molecule or pgRNA nucleic acid molecule;

(iii) the first and second viral transcription recognition signals are oriented in the same direction; and (iv) wherein a. if the negative strand nucleic acid molecule or pgRNA nucleic acid molecule is from a hepatitis B virus, each of the first and second viral transcription recognition signals comprises the epsilon recognition signal sequence of SEQ ID NO: 1;

b. if the negative strand nucleic acid molecule or pgRNA nucleic acid molecule is from an influenza virus, the second viral transcription recognition signal comprises the sequence of SEQ ID NO: 22 and the first viral transcription recognition signal comprises the sequence of SEQ ID NO: 23; or c. if the negative strand nucleic acid molecule or pgRNA nucleic acid molecule is from a coronavirus, each of the first and second viral transcription recognition signals comprises the sequence of SEQ ID NO: 25, SEQ ID NO: 26, SEQ ID NO: 28, or SEQ ID NO: 30.

13. A replication incompetent virus-like particle (VLP) comprising:

a negative strand nucleic acid molecule or a pregenomic RNA (pgRNA) nucleic acid molecule encoding a chemokine, a cytokine, an apoptosis inducing protein, a diphtheria toxin A, a diphtheria toxin A fragment, or any combination thereof, flanked by a first and second viral transcription recognition signals, wherein the negative strand nucleic acid molecule or pgRNA nucleic acid molecule is from a virus selected from the group consisting of hepatitis B virus, influenza virus and coronavirus;

a first promoter upstream (5') of the first viral transcription recognition signal and the 3' end of the negative strand nucleic acid molecule or pgRNA nucleic acid molecule; and a second promoter located between the second viral transcription recognition signal and the 5' end of the negative strand nucleic acid molecule or pgRNA nucleic acid molecule encoding a chemokine, a cytokine, an apoptosis inducing protein, a diphtheria toxin A, a diphtheria toxin A fragment, or any combination thereof, wherein (i) the first promoter and the second promoter are oriented in opposite direction and toward each other;

(ii) the second promoter and the second viral transcription recognition signal are upstream (5') of the 5' end of the negative strand nucleic acid molecule or pgRNA nucleic acid molecule;

(iii) the first and second viral transcription recognition signals are oriented in the same direction; and (iv) wherein a. if the negative strand nucleic acid molecule or pgRNA nucleic acid molecule is from a hepatitis B virus, each of the first and second viral transcription recognition signals comprises the epsilon recognition signal sequence of SEQ ID NO: 1;

b. if the negative strand nucleic acid molecule or pgRNA nucleic acid molecule is from an influenza virus, the second viral transcription recognition signal comprises the sequence of SEQ ID NO: 22 and the first viral transcription recognition signal comprises the sequence of SEQ ID NO: 23; or c. if the negative strand nucleic acid molecule or pgRNA nucleic acid molecule is from a coronavirus, each of the first and second viral transcription recognition signals comprises the sequence of SEQ ID NO: 25, SEQ ID NO: 26, SEQ ID NO: 28, or SEQ ID NO: 30.

14. A pharmaceutical composition comprising the replication incompetent virus-like particle of claim 12.

15. A method of inducing an apoptotic response against a cell infected with a virus selected from the group consisting of hepatitis B virus, influenza virus and coronavirus, in a mammalian subject in need thereof, the method comprising contacting the subject with the pharmaceutical composition of claim 11 or the pharmaceutical composition of claim 14.

16. A method of treating a hepatitis B, influenza, or coronavirus infection in a mammalian subject, the method comprising administering to the subject the pharmaceutical composition of claim 11 or the pharmaceutical composition of claim 14.

17. A method of inducing an apoptotic response against a cell infected with a virus selected from the group consisting of hepatitis B virus, influenza virus and coronavirus, in a mammalian subject in need thereof, the method comprising contacting the subject with the pharmaceutical composition of claim 14.

18. A method of treating a hepatitis B, influenza, or coronavirus infection in a mammalian subject, the method comprising administering to the subject the pharmaceutical composition of claim 14.

* * * * *

SEQUENCE LISTING

<160> NUMBER OF SEQ ID NOS: 36

<210> SEQ ID NO 1
<211> LENGTH: 61
<212> TYPE: RNA
<213> ORGANISM: Hepatitis B virus

<400> SEQUENCE: 1

```
uguucauguc cuacuguuca agccuccaag cugugccuug gguggcuuug gggcauggac     60

a                                                                     61
```

<210> SEQ ID NO 2
<211> LENGTH: 232
<212> TYPE: DNA
<213> ORGANISM: Homo sapiens

<400> SEQUENCE: 2

```
ggctccggtg cccgtcagtg ggcagagcgc acatcgccca cagtccccga gaagttgggg     60

ggaggggtcg gcaattgatc cggtgcctag agaaggtggc gcggggtaaa ctgggaaagt    120

gatgtcgtgt actggctccg cctttttccc gagggtgggg gagaaccgta tataagtgca    180

gtagtcgccg tgaacgttct ttttcgcaac gggtttgccg ccagaacaca gg            232
```

<210> SEQ ID NO 3
<211> LENGTH: 1251
<212> TYPE: DNA
<213> ORGANISM: Homo sapiens

<400> SEQUENCE: 3

```
atggacgaag cggatcggcg gctcctgcgg cggtgccggc tgcggctggt ggaagagctg     60

caggtggacc agctctggga cgccctgctg agccgcgagc tgttcaggcc ccatatgatc    120

gaggacatcc agcgggcagg ctctggatct cggcgggatc aggccaggca gctgatcata    180

gatctggaga ctcgagggag tcaggctctt cctttgttca tctcctgctt agaggacaca    240

ggccaggaca tgctggcttc gtttctgcga actaacaggc aagcagcaaa gttgtcgaag    300

ccaaccctag aaaaccttac cccagtggtg ctcagaccag agattcgcaa accagaggtt    360

ctcagaccgg aaacacccag accagtggac attggttctg gaggatttgg tgatgtcggt    420

gctcttgaga gtttgagggg aaatgcagat ttggcttaca tcctgagcat ggagccctgt    480

ggccactgcc tcattatcaa caatgtgaac ttctgccgtg agtccgggct ccgcacccgc    540

actggctcca acatcgactg tgagaagttg cggcgtcgct tctcctcgct gcatttcatg    600

gtggaggtga agggcgacct gactgccaag aaaatggtgc tggctttgct ggagctggcg    660

cagcaggacc acggtgctct ggactgctgc gtggtggtca ttctctctca cggctgtcag    720

gccagccacc tgcagttccc aggggctgtc tacggcacag atggatgccc tgtgtcggtc    780

gagaagattg tgaacatctt caatgggacc agctgcccca gcctgggagg gaagcccaag    840

ctctttttca tccaggcctg tggtggggag cagaaagacc atgggtttga ggtggcctcc    900

acttcccctg aagacgagtc ccctggcagt aaccccgagc cagatgccac cccgttccag    960

gaaggtttga ggaccttcga ccagctggac gccatatcta gtttgcccac acccagtgac   1020

atctttgtgt cctactctac tttcccaggt tttgtttcct ggagggaccc caagagtggc   1080

tcctggtacg ttgagaccct ggacgacatc tttgagcagt gggctcactc tgaagacctg   1140

cagtccctcc tgcttagggt cgctaatgct gtttcggtga aagggattta taaacagatg   1200

cctggttgct ttaatttcct ccggaaaaaa cttttcttta aaacatcata a            1251
```

<210> SEQ ID NO 4
<211> LENGTH: 1251
<212> TYPE: DNA
<213> ORGANISM: Homo sapiens

<400> SEQUENCE: 4
ttatgatgtt ttaaagaaaa gttttttccg gaggaaatta aagcaaccag gcatctgttt 60
ataaatccct ttcaccgaaa cagcattagc gaccctaagc aggagggact gcaggtcttc 120
agagtgagcc cactgctcaa agatgtcgtc cagggtctca acgtaccagg agccactctt 180
ggggtccctc caggaaacaa aacctgggaa agtagagtag gacacaaaga tgtcactggg 240
tgtgggcaaa ctagatatgg cgtccagctg gtcgaaggtc ctcaaacctt cctggaacgg 300
ggtggcatct ggctcggggt tactgccagg ggactcgtct tcaggggaag tggaggccac 360
ctcaaaccca tggtctttct gctccccacc acaggcctgg atgaaaaaga gcttgggctt 420
ccctcccagg ctggggcagc tggtcccatt gaagatgttc acaatcttct cgaccgacac 480
agggcatcca tctgtgccgt agacagcccc tgggaactgc aggtggctgg cctgacagcc 540
gtgagagaga atgaccacca cgcagcagtc cagagcaccg tggtcctgct gcgccagctc 600
cagcaaagcc agcaccattt tcttggcagt caggtcgccc ttcacctcca ccatgaaatg 660
cagcgaggag aagcgacgcc gcaacttctc acagtcgatg ttggagccag tgcgggtgcg 720
gagcccggac tcacggcaga agttcacatt gttgataatg aggcagtggc cacagggctc 780
catgctcagg atgtaagcca aatctgcatt tcccctcaaa ctctcaagag caccgacatc 840
accaaatcct ccagaaccaa tgtccactgg tctgggtgtt tccggtctga gaacctctgg 900
tttgcgaatc tctggtctga gcaccactgg ggtaaggttt tctagggttg gcttcgacaa 960
ctttgctgct tgcctgttag ttcgcagaaa cgaagccagc atgtcctggc ctgtgtcctc 1020
taagcaggag atgaacaaag gaagagcctg actccctcga gtctccagat ctatgatcag 1080
ctgcctggcc tgatcccgcc gagatccaga gcctgcccgc tggatgtcct cgatcatatg 1140
gggcctgaac agctcgcggc tcagcagggc gtcccagagc tggtccacct gcagctcttc 1200
caccagccgc agccggcacc gccgcaggag ccgccgatcc gcttcgtcca t 1251

<210> SEQ ID NO 5
<211> LENGTH: 232
<212> TYPE: DNA
<213> ORGANISM: Homo sapiens

<400> SEQUENCE: 5
cctgtgttct ggcggcaaac ccgttgcgaa aaagaacgtt cacggcgact actgcactta 60
tatacggttc tcccccaccc tcgggaaaaa ggcggagcca gtacacgaca tcactttccc 120
agtttacccc gcgccacctt ctctaggcac cggatcaatt gccgacccct ccccccaact 180
tctcggggac tgtgggcgat gtgcgctctg cccactgacg ggcaccggag cc 232

<210> SEQ ID NO 6
<211> LENGTH: 135
<212> TYPE: DNA
<213> ORGANISM: Simian virus 40

<400> SEQUENCE: 6
acttgtttat tgcagcttat aatggttaca aataaagcaa tagcatcaca aatttcacaa 60
ataaagcatt tttttcactg cattctagtt gtggtttgtc caaactcatc aatgtatctt 120
atcatgtctg gctct 135

<210> SEQ ID NO 7
<211> LENGTH: 135
<212> TYPE: DNA
<213> ORGANISM: Simian virus 40

<400> SEQUENCE: 7
agagccagac atgataagat acattgatga gtttggacaa accacaacta gaatgcagtg 60
aaaaaaatgc tttatttgtg aaatttgtga tgctattgct ttatttgtaa ccattataag 120
ctgcaataaa caagt 135

<210> SEQ ID NO 8
<211> LENGTH: 1746
<212> TYPE: DNA
<213> ORGANISM: Artificial Sequence
<220> FEATURE:
<223> OTHER INFORMATION: Synthetic sequence

<400> SEQUENCE: 8
atgtgttcat gtcctactgt tcaagcctcc aagctgtgcc ttgggtggct ttggggcatg 60
gacaagagcc agacatgata agatacattg atgagtttgg acaaaccaca actagaatgc 120
agtgaaaaaa atgctttatt tgtgaaattt gtgatgctat tgctttattt gtaaccatta 180
taagctgcaa taaacaagtt tatgatgttt taaagaaaag ttttttccgg aggaaattaa 240
agcaaccagg catctgttta taaatccctt tcaccgaaac agcattagcg accctaagca 300
ggagggactg caggtcttca gagtgagccc actgctcaaa gatgtcgtcc agggtctcaa 360
cgtaccagga gccactcttg gggtccctcc aggaaacaaa acctgggaaa gtagagtagg 420
acacaaagat gtcactgggt gtgggcaaac tagatatggc gtccagctgg tcgaaggtcc 480
tcaaaccttc ctggaacggg gtggcatctg gctcggggtt actgccaggg gactcgtctt 540
caggggaagt ggaggccacc tcaaacccat ggtctttctg ctccccacca caggcctgga 600
tgaaaaagag cttgggcttc cctcccaggc tggggcagct ggtcccattg aagatgttca 660
caatcttctc gaccgacaca gggcatccat ctgtgccgta gacagcccct gggaactgca 720
ggtggctggc ctgacagccg tgagagagaa tgaccaccac gcagcagtcc agagcaccgt 780
ggtcctgctg cgccagctcc agcaaagcca gcaccatttt cttggcagtc aggtcgccct 840
tcacctccac catgaaatgc agcgaggaga agcgacgccg caacttctca cagtcgatgt 900
tggagccagt gcgggtgcgg agcccggact cacggcagaa gttcacattg ttgataatga 960
ggcagtggcc acagggctcc atgctcagga tgtaagccaa atctgcattt cccctcaaac 1020
tctcaagagc accgacatca ccaaatcctc cagaaccaat gtccactggt ctgggtgttt 1080
ccggtctgag aacctctggt ttgcgaatct ctggtctgag caccactggg gtaaggtttt 1140
ctagggttgg cttcgacaac tttgctgctt gcctgttagt tcgcagaaac gaagccagca 1200
tgtcctggcc tgtgtcctct aagcaggaga tgaacaaagg aagagcctga ctccctcgag 1260
tctccagatc tatgatcagc tgcctggcct gatcccgccg agatccagag cctgcccgct 1320
ggatgtcctc gatcatatgg ggcctgaaca gctcgcggct cagcagggcg tcccagagct 1380
ggtccacctg cagctcttcc accagccgca gccggcaccg ccgcaggagc cgccgatccg 1440
cttcgtccat cctgtgttct ggcggcaaac ccgttgcgaa aaagaacgtt cacggcgact 1500
actgcactta tatacggttc tcccccaccc tcgggaaaaa ggcggagcca gtacacgaca 1560
tcactttccc agtttacccc gcgccacctt ctctaggcac cggatcaatt gccgacccct 1620 cccccaact tctcggggac tgtgggcgat gtgcgctctg cccactgacg ggcaccggag 1680
cctgttcatg tcctactgtt caagcctcca agctgtgcct tgggtggctt tggggcatgg 1740
acataa 1746

<210> SEQ ID NO 9
<211> LENGTH: 1191
<212> TYPE: DNA
<213> ORGANISM: Artificial Sequence
<220> FEATURE:
<223> OTHER INFORMATION: Synthetic sequence

<400> SEQUENCE: 9
atgtgttcat gtcctactgt tcaagcctcc aagctgtgcc ttgggtggct ttggggcatg 60
gacaagagcc agacatgata agatacattg atgagtttgg acaaaccaca actagaatgc 120
agtgaaaaaa atgctttatt tgtgaaattt gtgatgctat tgctttattt gtaaccatta 180
taagctgcaa taaacaagtt tagggcaagg cggagccgga ggcgatggcg tgctcggtca 240
ggtgccactt ctggttcttg gcgtcgctgc ggtcctcgcg ggtcagcttg tgctggatga 300
agtgccagtc gggcatcttg cggggcacgg acttggcctt gtacacggtg tcgaactggc 360
agcgcaagcg gccaccgtcc ttcagcagca ggtacatgct cacgtcgccc ttcaagatgc 420
cctgcttggg cacggggatg atcttctcgc aggagggctc ccagttgtcg gtcatcttct 480
tcatcacggg gccgtcggcg gggaagttca cgccgtagaa cttggactcg tggtacatgc 540
agttctcctc cacgctcacg gtgatgtcgg cgttgcagat gcacacggcg ccgtcctcga 600
acaggaagga gcggtcccag gtgtagccgg cggggcagga gttcttgaag tagtcgacga 660
tgtcctgggg gtactcggtg aacacgcggt tgccgtacat gaaggcggcg gacaagatgt 720
cctcggcgaa gggcaagggg ccgccctcca ccacgcacag gttgatggcc tgcttgccct 780
tgaaggggta gccgatgccc tcgccggtga tcacgaactt gtggccgtcc acgcagccct 840
ccatgcggta cttcatggtc atctccttgg tcaggccgtg cttggactgg gccatcctgt 900
gttctggcgg caaacccgtt gcgaaaaaga acgttcacgg cgactactgc acttatatac 960
ggttctcccc caccctcggg aaaaaggcgg agccagtaca cgacatcact ttcccagttt 1020
accccgcgcc accttctcta ggcaccggat caattgccga cccctccccc caacttctcg 1080
gggactgtgg gcgatgtgcg ctctgcccac tgacgggcac cggagcctgt tcatgtccta 1140
ctgttcaagc ctccaagctg tgccttgggt ggctttgggg catggacata a 1191

<210> SEQ ID NO 10
<211> LENGTH: 12
<212> TYPE: DNA
<213> ORGANISM: Artificial Sequence
<220> FEATURE:
<223> OTHER INFORMATION: Synthetic sequence

<400> SEQUENCE: 10
cctgcttttg ct 12

<210> SEQ ID NO 11
<211> LENGTH: 13
<212> TYPE: DNA
<213> ORGANISM: Artificial Sequence
<220> FEATURE:
<223> OTHER INFORMATION: Synthetic sequence

<400> SEQUENCE: 11

-continued agtagaaaca agg 13

<210> SEQ ID NO 12
<211> LENGTH: 1292
<212> TYPE: DNA
<213> ORGANISM: Artificial Sequence
<220> FEATURE:
<223> OTHER INFORMATION: Synthetic sequence

<400> SEQUENCE: 12
agtagaaaca agggtgtttt ttatcattat gatgttttaa agaaaagttt tttccggagg 60
aaattaaagc aaccaggcat ctgtttataa atccctttca ccgaaacagc attagcgacc 120
ctaagcagga gggactgcag gtcttcagag tgagcccact gctcaaagat gtcgtccagg 180
gtctcaacgt accaggagcc actcttgggg tccctccagg aaacaaaacc tgggaaagta 240
gagtaggaca caaagatgtc actgggtgtg ggcaaactag atatggcgtc cagctggtcg 300
aaggtcctca aaccttcctg gaacggggtg gcatctggct cggggttact gccaggggac 360
tcgtcttcag gggaagtgga ggccacctca aacccatggt ctttctgctc cccaccacag 420
gcctggatga aaaagagctt gggcttccct cccaggctgg ggcagctggt cccattgaag 480
atgttcacaa tcttctcgac cgacacaggg catccatctg tgccgtagac agcccctggg 540
aactgcaggt ggctggcctg acagccgtga gagagaatga ccaccacgca gcagtccaga 600
gcaccgtggt cctgctgcgc cagctccagc aaagccagca ccattttctt ggcagtcagg 660
tcgcccttca cctccaccat gaaatgcagc gaggagaagc gacgccgcaa cttctcacag 720
tcgatgttgg agccagtgcg ggtgcggagc ccggactcac ggcagaagtt cacattgttg 780
ataatgaggc agtggccaca gggctccatg ctcaggatgt aagccaaatc tgcatttccc 840
ctcaaactct caagagcacc gacatcacca aatcctccag aaccaatgtc cactggtctg 900
ggtgtttccg gtctgagaac ctctggtttg cgaatctctg gtctgagcac cactggggta 960
aggttttcta gggttggctt cgacaacttt gctgcttgcc tgttagttcg cagaaacgaa 1020
gccagcatgt cctggcctgt gtcctctaag caggagatga acaaaggaag agcctgactc 1080
cctcgagtct ccagatctat gatcagctgc ctggcctgat cccgccgaga tccagagcct 1140
gcccgctgga tgtcctcgat catatggggc ctgaacagct cgcggctcag cagggcgtcc 1200
cagagctggt ccacctgcag ctcttccacc agccgcagcc ggcaccgccg caggagccgc 1260
cgatccgctt cgtccattcc cctgcttttg ct 1292

<210> SEQ ID NO 13
<211> LENGTH: 13
<212> TYPE: DNA
<213> ORGANISM: Artificial Sequence
<220> FEATURE:
<223> OTHER INFORMATION: Synthetic sequence

<400> SEQUENCE: 13
agtagaaaca agg 13

<210> SEQ ID NO 14
<211> LENGTH: 12
<212> TYPE: DNA
<213> ORGANISM: Artificial Sequence
<220> FEATURE:
<223> OTHER INFORMATION: Synthetic sequence

<400> SEQUENCE: 14
cctgcttttg ct 12

<210> SEQ ID NO 15
<211> LENGTH: 1292
<212> TYPE: RNA
<213> ORGANISM: Artificial Sequence
<220> FEATURE:
<223> OTHER INFORMATION: Synthetic sequence

<400> SEQUENCE: 15
aguagaaaca agggguguuuu uuaucauuau gauguuuuaa agaaaaguuu uuuccggagg 60
aaauuaaagc aaccaggcau cuguuuauaa aucccuuuca ccgaaacagc auuagcgacc 120
cuaagcagga gggacugcag gucuucagag ugagcccacu gcucaaagau gucguccagg 180
gucucaacgu accaggagcc acucuugggg ucccuccagg aaacaaaacc ugggaaagua 240
gaguaggaca caaagauguc acugggugug ggcaaacuag auauggcguc cagcuggucg 300
aagguccuca aaccuuccug gaacggggug gcaucuggcu cgggguuacu gccaggggac 360
ucgucuucag gggaagugga ggccaccuca aacccauggu cuuucugcuc cccaccacag 420
gccuggauga aaaagagcuu gggcuucccu cccaggcugg ggcagcuggu cccauugaag 480
auguucacaa ucuucucgac cgacacaggg cauccaucug ugccguagac agccccuggg 540
aacugcaggu ggcuggccug acagccguga gagagaauga ccaccacgca gcaguccaga 600
gcaccguggu ccugcugcgc cagcuccagc aaagccagca ccauuuucuu ggcagucagg 660
ucgcccuuca ccuccaccau gaaaugcagc gaggagaagc gacgccgcaa cuucucacag 720
ucgauguugg agccagugcg ggugcggagc ccggacucac ggcagaaguu cacauuguug 780
auaaugaggc aguggccaca gggcuccaug cucaggaugu aagccaaauc ugcauuuccc 840
cucaaacucu caagagcacc gacaucacca aauccuccag aaccaauguc cacuggucug 900
gguguuuccg gucugagaac cucugguuug cgaaucucug gucugagcac cacuggggua 960
agguuuucua ggguuggcuu cgacaacuuu gcugcuugcc uguuaguucg cagaaacgaa 1020
gccagcaugu ccuggccugu guccucuaag caggagauga acaaaggaag agccugacuc 1080
ccucgagucu ccagaucuau gaucagcugc cuggccugau cccgccgaga uccagagccu 1140
gcccgcugga uguccucgau cauaugggc cugaacagcu cgcggcucag cagggcgucc 1200
cagagcuggu ccaccugcag cucuuccacc agccgcagcc ggcaccgccg caggagccgc 1260
cgauccgcuu cguccauucc ccugcuuuug cu 1292

<210> SEQ ID NO 16
<211> LENGTH: 29
<212> TYPE: DNA
<213> ORGANISM: Artificial Sequence
<220> FEATURE:
<223> OTHER INFORMATION: Synthetic sequence

<400> SEQUENCE: 16
agtagaaaca agggtgtttt ttatcatta 29

<210> SEQ ID NO 17
<211> LENGTH: 18
<212> TYPE: DNA
<213> ORGANISM: Artificial Sequence
<220> FEATURE:
<223> OTHER INFORMATION: Synthetic sequence

<400> SEQUENCE: 17
cattcccctg cttttgct 18

<210> SEQ ID NO 18
<211> LENGTH: 761
<212> TYPE: DNA
<213> ORGANISM: Artificial Sequence
<220> FEATURE:
<223> OTHER INFORMATION: Synthetic sequence

<400> SEQUENCE: 18
agtagaaaca agggtgtttt ttatcattac ttgtacagct cgtccatgcc gagagtgatc 60
ccggcggcgg tcacgaactc cagcaggacc atgtgatcgc gcttctcgtt ggggtctttg 120
ctcagggcgg actgggtgct caggtagtgg ttgtcgggca gcagcacggg gccgtcgccg 180
atgggggtgt tctgctggta gtggtcggcg agctgcacgc tgccgtcctc gatgttgtgg 240
cggatcttga agttcacctt gatgccgttc ttctgcttgt cggccatgat atagacgttg 300
tggctgttgt agttgtactc cagcttgtgc cccaggatgt tgccgtcctc cttgaagtcg 360
atgcccttca gctcgatgcg gttcaccagg gtgtcgccct cgaacttcac ctcggcgcgg 420
gtcttgtagt tgccgtcgtc cttgaagaag atggtgcgct cctggacgta gccttcgggc 480
atggcggact tgaagaagtc gtgctgcttc atgtggtcgg ggtagcggct gaagcactgc 540
acgccgtagg tcagggtggt cacgagggtg ggccagggca cgggcagctt gccggtggtg 600
cagatgaact tcagggtcag cttgccgtag gtggcatcgc cctcgccctc gccggacacg 660
ctgaacttgt ggccgtttac gtcgccgtcc agctcgacca ggatgggcac caccccggtg 720
aacagctcct cgcccttgct caccattccc ctgcttttgc t 761

<210> SEQ ID NO 19
<211> LENGTH: 265
<212> TYPE: DNA
<213> ORGANISM: Artificial Sequence
<220> FEATURE:
<223> OTHER INFORMATION: Synthetic sequence

<400> SEQUENCE: 19
attaaaggtt tataccttcc caggtaacaa accaaccaac tttcgatctc ttgtagatct 60
gttctctaaa cgaactttaa aatctgtgtg gctgtcactc ggctgcatgc ttagtgcact 120
cacgcagtat aattaataac taattactgt cgttgacagg acacgagtaa ctcgtctatc 180
ttctgcaggc tgcttacggt ttcgtccgtg ttgcagccga tcatcagcac atctaggttt 240
cgtccgggtg tgaccgaaag gtaag 265

<210> SEQ ID NO 20
<211> LENGTH: 229
<212> TYPE: DNA
<213> ORGANISM: Artificial Sequence
<220> FEATURE:
<223> OTHER INFORMATION: Synthetic sequence

<400> SEQUENCE: 20
caatctttaa tcagtgtgta acattaggga ggacttgaaa gagccaccac attttcaccg 60
aggccacgcg gagtacgatc gagtgtacag tgaacaatgc tagggagagc tgcctatatg 120
gaagagccct aatgtgtaaa attaatttta gtagtgctat ccccatgtga ttttaatagc 180
ttcttaggag aatgacaaaa aaacaatctt gctaaacact gtcttcatg 229

<210> SEQ ID NO 21
<211> LENGTH: 603
<212> TYPE: DNA
<213> ORGANISM: Artificial Sequence
<220> FEATURE:
<223> OTHER INFORMATION: Synthetic sequence

<400> SEQUENCE: 21
atgggcgctg atgatgttgt tgattcttct aaatcttttg tgatggaaaa cttttcttcg 60
taccacggga ctaaacctgg ttatgtagat tccattcaaa aaggtataca aaagccaaaa 120
tctggtacac aaggaaatta tgacgatgat tggaaagggt tttatagtac cgacaataaa 180
tacgacgctg cgggatactc tgtagataat gaaaacccgc tctctggaaa agctggaggc 240
gtggtcaaag tgacgtatcc aggactgacg aaggttctcg cactaaaagt ggataatgcc 300
gaaactatta agaaagagtt aggtttaagt ctcactgaac cgttgatgga gcaagtcgga 360
acggaagagt ttatcaaaag gttcggtgat ggtgcttcgc gtgtagtgct cagccttccc 420
ttcgctgagg ggagttctag cgttgaatat attaataact gggaacaggc gaaagcgtta 480
agcgtagaac ttgagattaa ttttgaaacc cgtggaaaac gtggccaaga tgcgatgtat 540
gagtatatgg ctcaagcctg tgcaggaaat cgtgtcaggc gatcagtagg tagctcattg 600
taa 603

<210> SEQ ID NO 22
<211> LENGTH: 1097
<212> TYPE: DNA
<213> ORGANISM: Artificial Sequence
<220> FEATURE:
<223> OTHER INFORMATION: Synthetic sequence

<400> SEQUENCE: 22
attaaaggtt tataccttcc caggtaacaa accaaccaac tttcgatctc ttgtagatct 60
gttctctaaa cgaactttaa aatctgtgtg gctgtcactc ggctgcatgc ttagtgcact 120
cacgcagtat aattaataac taattactgt cgttgacagg acacgagtaa ctcgtctatc 180
ttctgcaggc tgcttacggt ttcgtccgtg ttgcagccga tcatcagcac atctaggttt 240
cgtccgggtg tgaccgaaag gtaagatggg cgctgatgat gttgttgatt cttctaaatc 300
ttttgtgatg gaaaactttt cttcgtacca cgggactaaa cctggttatg tagattccat 360
tcaaaaaggt atacaaaagc caaaatctgg tacacaagga aattatgacg atgattggaa 420
agggttttat agtaccgaca ataaatacga cgctgcggga tactctgtag ataatgaaaa 480
cccgctctct ggaaaagctg gaggcgtggt caaagtgacg tatccaggac tgacgaaggt 540
tctcgcacta aaagtggata atgccgaaac tattaagaaa gagttaggtt taagtctcac 600
tgaaccgttg atggagcaag tcggaacgga agagtttatc aaaaggttcg gtgatggtgc 660
ttcgcgtgta gtgctcagcc ttcccttcgc tgaggggagt tctagcgttg aatatattaa 720
taactgggaa caggcgaaag cgttaagcgt agaacttgag attaattttg aaacccgtgg 780
aaaacgtggc caagatgcga tgtatgagta tatggctcaa gcctgtgcag gaaatcgtgt 840
caggcgatca gtaggtagct cattgtaaca atctttaatc agtgtgtaac attagggagg 900
acttgaaaga gccaccacat tttcaccgag gccacgcgga gtacgatcga gtgtacagtg 960
aacaatgcta gggagagctg cctatatgga agagccctaa tgtgtaaaat taattttagt 1020
agtgctatcc ccatgtgatt ttaatagctt cttaggagaa tgacaaaaaa acaatcttgc 1080
taaacactgt cttcatg 1097

<210> SEQ ID NO 23
<211> LENGTH: 603
<212> TYPE: DNA

<213> ORGANISM: Artificial Sequence
<220> FEATURE:
<223> OTHER INFORMATION: Synthetic sequence

<400> SEQUENCE: 23
ttacaatgag ctacctactg atcgcctgac acgatttcct gcacaggctt gagccatata 60
ctcatacatc gcatcttggc cacgttttcc acgggtttca aaattaatct caagttctac 120
gcttaacgct ttcgcctgtt cccagttatt aatatattca acgctagaac tcccctcagc 180
gaagggaagg ctgagcacta cacgcgaagc accatcaccg aaccttttga taaactcttc 240
cgttccgact tgctccatca acggttcagt gagacttaaa cctaactctt tcttaatagt 300
ttcggcatta tccactttta gtgcgagaac cttcgtcagt cctggatacg tcactttgac 360
cacgcctcca gcttttccag agagcgggtt ttcattatct acagagtatc ccgcagcgtc 420
gtatttattg tcggtactat aaaacccttt ccaatcatcg tcataatttc cttgtgtacc 480
agattttggc ttttgtatac ctttttgaat ggaatctaca taaccaggtt tagtcccgtg 540
gtacgaagaa aagttttcca tcacaaaaga tttagaagaa tcaacaacat catcagcgcc 600
cat 603

<210> SEQ ID NO 24
<211> LENGTH: 1097
<212> TYPE: DNA
<213> ORGANISM: Artificial Sequence
<220> FEATURE:
<223> OTHER INFORMATION: Synthetic sequence

<400> SEQUENCE: 24
catgaagaca gtgtttagca agattgtttt tttgtcattc tcctaagaag ctattaaaat 60
cacatgggga tagcactact aaaattaatt ttacacatta gggctcttcc atataggcag 120
ctctccctag cattgttcac tgtacactcg atcgtactcc gcgtggcctc ggtgaaaatg 180
tggtggctct ttcaagtcct ccctaatgtt acacactgat taaagattgt tacaatgagc 240
tacctactga tcgcctgaca cgatttcctg cacaggcttg agccatatac tcatacatcg 300
catcttggcc acgttttcca cgggtttcaa aattaatctc aagttctacg cttaacgctt 360
tcgcctgttc ccagttatta atatattcaa cgctagaact cccctcagcg aagggaaggc 420
tgagcactac acgcgaagca ccatcaccga accttttgat aaactcttcc gttccgactt 480
gctccatcaa cggttcagtg agacttaaac ctaactcttt cttaatagtt tcggcattat 540
ccacttttag tgcgagaacc ttcgtcagtc ctggatacgt cactttgacc acgcctccag 600
cttttccaga gagcgggttt tcattatcta cagagtatcc cgcagcgtcg tatttattgt 660
cggtactata aaaccctttc caatcatcgt cataatttcc ttgtgtacca gattttggct 720
tttgtatacc tttttgaatg gaatctacat aaccaggttt agtcccgtgg tacgaagaaa 780
agttttccat cacaaaagat ttagaagaat caacaacatc atcagcgccc atcttacctt 840
tcggtcacac ccggacgaaa cctagatgtg ctgatgatcg gctgcaacac ggacgaaacc 900
gtaagcagcc tgcagaagat agacgagtta ctcgtgtcct gtcaacgaca gtaattagtt 960
attaattata ctgcgtgagt gcactaagca tgcagccgag tgacagccac acagatttta 1020
aagttcgttt agagaacaga tctacaagag atcgaaagtt ggttggtttg ttacctggga 1080
aggtataaac ctttaat 1097

<210> SEQ ID NO 25
<211> LENGTH: 265

-continued

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
attaaaggtt tataccttcc caggtaacaa accaaccaac tttcgatctc ttgtagatct     60
gttctctaaa cgaactttaa aatctgtgtg gctgtcactc ggctgcatgc ttagtgcact    120
cacgcagtat aattaataac taattactgt cgttgacagg acacgagtaa ctcgtctatc    180
ttctgcaggc tgcttacggt ttcgtccgtg ttgcagccga tcatcagcac atctaggttt    240
cgtccgggtg tgaccgaaag gtaag                                          265

<210> SEQ ID NO 26
<211> LENGTH: 229
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
caatctttaa tcagtgtgta acattaggga ggacttgaaa gagccaccac attttcaccg     60
aggccacgcg gagtacgatc gagtgtacag tgaacaatgc tagggagagc tgcctatatg    120
gaagagccct aatgtgtaaa attaatttta gtagtgctat ccccatgtga ttttaatagc    180
ttcttaggag aatgacaaaa aaacaatctt gctaaacact gtcttcatg                229

<210> SEQ ID NO 27
<211> LENGTH: 603
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
atgggcgctg atgatgttgt tgattcttct aaatcttttg tgatggaaaa cttttcttcg     60
taccacggga ctaaacctgg ttatgtagat tccattcaaa aaggtataca aaagccaaaa    120
tctggtacac aaggaaatta tgacgatgat tggaaagggt tttatagtac cgacaataaa    180
tacgacgctg cgggatactc tgtagataat gaaaacccgc tctctggaaa agctggaggc    240
gtggtcaaag tgacgtatcc aggactgacg aaggttctcg cactaaaagt ggataatgcc    300
gaaactatta agaaagagtt aggtttaagt ctcactgaac cgttgatgga gcaagtcgga    360
acggaagagt ttatcaaaag gttcggtgat ggtgcttcgc gtgtagtgct cagccttccc    420
ttcgctgagg ggagttctag cgttgaatat attaataact gggaacaggc gaaagcgtta    480
agcgtagaac ttgagattaa ttttgaaacc cgtggaaaac gtggccaaga tgcgatgtat    540
gagtatatgg ctcaagcctg tgcaggaaat cgtgtcaggc gatcagtagg tagctcattg    600
taa                                                                  603

<210> SEQ ID NO 28
<211> LENGTH: 1097
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
attaaaggtt tataccttcc caggtaacaa accaaccaac tttcgatctc ttgtagatct 60
gttctctaaa cgaactttaa aatctgtgtg gctgtcactc ggctgcatgc ttagtgcact 120
cacgcagtat aattaataac taattactgt cgttgacagg acacgagtaa ctcgtctatc 180
ttctgcaggc tgcttacggt ttcgtccgtg ttgcagccga tcatcagcac atctaggttt 240
cgtccgggtg tgaccgaaag gtaagatggg cgctgatgat gttgttgatt cttctaaatc 300
ttttgtgatg gaaaactttt cttcgtacca cgggactaaa cctggttatg tagattccat 360
tcaaaaaggt atacaaaagc caaaatctgg tacacaagga aattatgacg atgattggaa 420
agggttttat agtaccgaca ataaatacga cgctgcggga tactctgtag ataatgaaaa 480
cccgctctct ggaaaagctg gaggcgtggt caaagtgacg tatccaggac tgacgaaggt 540
tctcgcacta aaagtggata atgccgaaac tattaagaaa gagttaggtt taagtctcac 600
tgaaccgttg atggagcaag tcggaacgga agagtttatc aaaaggttcg gtgatggtgc 660
ttcgcgtgta gtgctcagcc ttcccttcgc tgaggggagt tctagcgttg aatatattaa 720
taactgggaa caggcgaaag cgttaagcgt agaacttgag attaattttg aaacccgtgg 780
aaaacgtggc caagatgcga tgtatgagta tatggctcaa gcctgtgcag gaaatcgtgt 840
caggcgatca gtaggtagct cattgtaaca atctttaatc agtgtgtaac attagggagg 900
acttgaaaga gccaccacat tttcaccgag gccacgcgga gtacgatcga gtgtacagtg 960
aacaatgcta gggagagctg cctatatgga agagccctaa tgtgtaaaat taattttagt 1020
agtgctatcc ccatgtgatt ttaatagctt cttaggagaa tgacaaaaaa acaatcttgc 1080
taaacactgt cttcatg 1097

<210> SEQ ID NO 29
<211> LENGTH: 603
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 29
ttacaatgag ctacctactg atcgcctgac acgatttcct gcacaggctt gagccatata 60
ctcatacatc gcatcttggc cacgttttcc acgggtttca aaattaatct caagttctac 120
gcttaacgct ttcgcctgtt cccagttatt aatatattca acgctagaac tcccctcagc 180
gaagggaagg ctgagcacta cacgcgaagc accatcaccg aaccttttga taaactcttc 240
cgttccgact tgctccatca acggttcagt gagacttaaa cctaactctt tcttaatagt 300
ttcggcatta tccactttta gtgcgagaac cttcgtcagt cctggatacg tcactttgac 360
cacgcctcca gcttttccag agagcgggtt ttcattatct acagagtatc ccgcagcgtc 420
gtatttattg tcggtactat aaaacccttt ccaatcatcg tcataatttc cttgtgtacc 480
agattttggc ttttgtatac ctttttgaat ggaatctaca taaccaggtt tagtcccgtg 540
gtacgaagaa aagttttcca tcacaaaaga tttagaagaa tcaacaacat catcagcgcc 600
cat 603

<210> SEQ ID NO 30
<211> LENGTH: 1097
<212> TYPE: DNA
<213> ORGANISM: Artificial Sequence
<220> FEATURE:

-continued

<223> OTHER INFORMATION: Description of Artificial Sequence: Synthetic
      polynucleotide

<400> SEQUENCE: 30
catgaagaca gtgtttagca agattgtttt tttgtcattc tcctaagaag ctattaaaat     60
cacatgggga tagcactact aaaattaatt ttacacatta gggctcttcc atataggcag    120
ctctccctag cattgttcac tgtacactcg atcgtactcc gcgtggcctc ggtgaaaatg    180
tggtggctct ttcaagtcct ccctaatgtt acacactgat taaagattgt tacaatgagc    240
tacctactga tcgcctgaca cgatttcctg cacaggcttg agccatatac tcatacatcg    300
catcttggcc acgttttcca cgggtttcaa aattaatctc aagttctacg cttaacgctt    360
tcgcctgttc ccagttatta atatattcaa cgctagaact cccctcagcg aagggaaggc    420
tgagcactac acgcgaagca ccatcaccga accttttgat aaactcttcc gttccgactt    480
gctccatcaa cggttcagtg agacttaaac ctaactcttt cttaatagtt tcggcattat    540
ccacttttag tgcgagaacc ttcgtcagtc ctggatacgt cactttgacc acgcctccag    600
cttttccaga gagcgggttt tcattatcta cagagtatcc cgcagcgtcg tatttattgt    660
cggtactata aaaccctttc caatcatcgt cataatttcc ttgtgtacca gattttggct    720
tttgtatacc tttttgaatg gaatctacat aaccaggttt agtcccgtgg tacgaagaaa    780
agttttccat cacaaaagat ttagaagaat caacaacatc atcagcgccc atcttacctt    840
tcggtcacac ccggacgaaa cctagatgtg ctgatgatcg gctgcaacac ggacgaaacc    900
gtaagcagcc tgcagaagat agacgagtta ctcgtgtcct gtcaacgaca gtaattagtt    960
attaattata ctgcgtgagt gcactaagca tgcagccgag tgacagccac acagatttta   1020
aagttcgttt agagaacaga tctacaagag atcgaaagtt ggttggtttg ttacctggga   1080
aggtataaac ctttaat                                                  1097

<210> SEQ ID NO 31
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31 acgaac                                                                 6

<210> SEQ ID NO 32
<211> LENGTH: 6
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 32 guucgu                                                                 6

<210> SEQ ID NO 33
<211> LENGTH: 6734
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33

-continued

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc ttctagacaa ctttgtatag aaaagttggg ctccggtgcc    180
cgtcagtggg cagagcgcac atcgcccaca gtccccgaga agttgggggg aggggtcggc    240
aattgaaccg gtgcctagag aaggtggcgc ggggtaaact gggaaagtga tgtcgtgtac    300
tggctccgcc tttttcccga gggtggggga gaaccgtata taagtgcagt agtcgccgtg    360
aacgttcttt ttcgcaacgg gtttgccgcc agaacacagg taagtgccgt gtgtggttcc    420
cgcgggcctg gcctctttac gggttatggc ccttgcgtgc cttgaattac ttccacctgg    480
ctgcagtacg tgattcttga tcccgagctt cgggttggaa gtgggtggga gagttcgagg    540
ccttgcgctt aaggagcccc ttcgcctcgt gcttgagttg aggcctggcc tgggcgctgg    600
ggccgccgcg tgcgaatctg gtggcacctt cgcgcctgtc tcgctgcttt cgataagtct    660
ctagccattt aaaatttttg atgacctgct gcgacgcttt ttttctggca agatagtctt    720
gtaaatgcgg gccaagatct gcacactggt atttcggttt ttggggccgc gggcggcgac    780
ggggcccgtg cgtcccagcg cacatgttcg gcgaggcggg gcctgcgagc gcggccaccg    840
agaatcggac gggggtagtc tcaagctggc cggcctgctc tggtgcctgg tctcgcgccg    900
ccgtgtatcg ccccgccctg ggcggcaagg ctggcccggt cggcaccagt tgcgtgagcg    960
gaaagatggc cgcttcccgg ccctgctgca gggagctcaa aatggaggac gcggcgctcg   1020
ggagagcggg cgggtgagtc acccacacaa aggaaaaggg cctttccgtc ctcagccgtc   1080
gcttcatgtg actccacgga gtaccgggcg ccgtccaggc acctcgatta gttctcgagc   1140
ttttggagta cgtcgtcttt aggttggggg gaggggtttt atgcgatgga gtttccccac   1200
actgagtggg tggagactga agttaggcca gcttggcact tgatgtaatt ctccttggaa   1260
tttgcccttt ttgagtttgg atcttggttc attctcaagc ctcagacagt ggttcaaagt   1320
tttttcttc catttcaggt gtcgtgacaa gtttgtacaa aaaagcaggc tgccaccatg   1380
tgttcatgtc ctactgttca agcctccaag ctgtgccttg ggtggctttg ggcatggac   1440
aagagccaga catgataaga tacattgatg agtttggaca aaccacaact agaatgcagt   1500
gaaaaaaatg ctttatttgt gaaatttgtg atgctattgc tttatttgta accattataa   1560
gctgcaataa acaagtttat gatgttttaa agaaaagttt tttccggagg aaattaaagc   1620
aaccaggcat ctgtttataa atccctttca ccgaaacagc attagcgacc ctaagcagga   1680
gggactgcag gtcttcagag tgagcccact gctcaaagat gtcgtccagg gtctcaacgt   1740
accaggagcc actcttgggg tccctccagg aaacaaaacc tgggaaagta gagtaggaca   1800
caaagatgtc actgggtgtg ggcaaactag atatggcgtc cagctggtcg aaggtcctca   1860
aaccttcctg gaacggggtg gcatctggct cggggttact gccaggggac tcgtcttcag   1920
gggaagtgga ggccacctca aacccatggt ctttctgctc cccaccacag gcctggatga   1980
aaaagagctt gggcttccct cccaggctgg ggcagctggt cccattgaag atgttcacaa   2040
tcttctcgac cgacacaggg catccatctg tgccgtagac agcccctggg aactgcaggt   2100
ggctggcctg acagccgtga gagagaatga ccaccacgca gcagtccaga gcaccgtggt   2160
cctgctgcgc cagctccagc aaagccagca ccattttctt ggcagtcagg tcgcccttca   2220
cctccaccat gaaatgcagc gaggagaagc gacgccgcaa cttctcacag tcgatgttgg   2280
agccagtgcg ggtgcggagc ccggactcac ggcagaagtt cacattgttg ataatgaggc   2340
```

-continued

```
agtggccaca gggctccatg ctcaggatgt aagccaaatc tgcatttccc ctcaaactct   2400
caagagcacc gacatcacca aatcctccag aaccaatgtc cactggtctg ggtgtttccg   2460
gtctgagaac ctctggtttg cgaatctctg gtctgagcac cactggggta aggttttcta   2520
gggttggctt cgacaacttt gctgcttgcc tgttagttcg cagaaacgaa gccagcatgt   2580
cctggcctgt gtcctctaag caggagatga acaaaggaag agcctgactc cctcgagtct   2640
ccagatctat gatcagctgc ctggcctgat cccgccgaga tccagagcct gcccgctgga   2700
tgtcctcgat catatggggc ctgaacagct cgcggctcag cagggcgtcc cagagctggt   2760
ccacctgcag ctcttccacc agccgcagcc ggcaccgccg caggagccgc cgatccgctt   2820
cgtccatcct gtgttctggc ggcaaacccg ttgcgaaaaa gaacgttcac ggcgactact   2880
gcacttatat acggttctcc cccaccctcg ggaaaaaggc ggagccagta cacgacatca   2940
ctttcccagt ttaccccgcg ccaccttctc taggcaccgg atcaattgcc gacccctccc   3000
cccaacttct cggggactgt gggcgatgtg cgctctgccc actgacgggc accggagcct   3060
gttcatgtcc tactgttcaa gcctccaagc tgtgccttgg gtggctttgg ggcatggaca   3120
taaacccagc tttcttgtac aaagtgggaa ttccgataat caacctctgg attacaaaat   3180
ttgtgaaaga ttgactggta ttcttaacta tgttgctcct tttacgctat gtggatacgc   3240
tgctttaatg cctttgtatc atgctattgc ttcccgtatg gctttcattt tctcctcctt   3300
gtataaatcc tggttgctgt ctctttatga ggagttgtgg cccgttgtca ggcaacgtgg   3360
cgtggtgtgc actgtgtttg ctgacgcaac ccccactggt tggggcattg ccaccacctg   3420
tcagctcctt tccgggactt tcgctttccc cctccctatt gccacggcgg aactcatcgc   3480
cgcctgcctt gcccgctgct ggacaggggc tcggctgttg ggcactgaca attccgtggt   3540
gttgtcgggg aagctgacgt cctttccatg gctgctcgcc tgtgttgcca cctggattct   3600
gcgcgggacg tccttctgct acgtcccttc ggccctcaat ccagcggacc ttccttcccg   3660
cggcctgctg ccggctctgc ggcctcttcc gcgtcttcgc cttcgccctc agacgagtcg   3720
gatctccctt tgggccgcct ccccgcatcg ggaattccta gagctcgctg atcagcctcg   3780
actgtgcctt ctagttgcca gccatctgtt gtttgcccct cccccgtgcc ttccttgacc   3840
ctggaaggtg ccactcccac tgtcctttcc taataaaatg aggaaattgc atcgcattgt   3900
ctgagtaggt gtcattctat tctggggggt ggggtggggc aggacagcaa gggggaggat   3960
tgggaagaga atagcaggca tgctggggag ggccgcagga acccctagtg atggagttgg   4020
ccactccctc tctgcgcgct cgctcgctca ctgaggccgg gcgaccaaag gtcgcccgac   4080
gcccgggctt tgcccgggcg gcctcagtga gcgagcgagc gcgcagctgc ctgcaggggc   4140
gcctgatgcg gtattttctc cttacgcatc tgtgcggtat ttcacaccgc atacgtcaaa   4200
gcaaccatag tacgcgccct gtagcggcgc attaagcgcg gcgggggtgg tggttacgcg   4260
cagcgtgacc gctacacttg ccagcgcctt agcgcccgct cctttcgctt tcttcccttc   4320
ctttctcgcc acgttcgccg gctttccccg tcaagctcta aatcgggggc tccctttagg   4380
gttccgattt agtgctttac ggcacctcga ccccaaaaaa cttgatttgg gtgatggttc   4440
acgtagtggg ccatcgccct gatagacggt ttttcgccct ttgacgttgg agtccacgtt   4500
ctttaatagt ggactcttgt tccaaactgg aacaacactc aactctatct cgggctattc   4560
ttttgattta taagggattt tgccgatttc ggtctattgg ttaaaaaatg agctgattta   4620
acaaaaattt aacgcgaatt ttaacaaaat attaacgttt acaattttat ggtgcactct   4680
cagtacaatc tgctctgatg ccgcatagtt aagccagccc cgacacccgc caacacccgc   4740
```

-continued tgacgcgccc tgacgggctt gtctgctccc ggcatccgct tacagacaag ctgtgaccgt 4800
ctccgggagc tgcatgtgtc agaggttttc accgtcatca ccgaaacgcg cgagacgaaa 4860
gggcctcgtg atacgcctat ttttataggt taatgtcatg ataataatgg tttcttagac 4920
gtcaggtggc acttttcggg gaaatgtgcg cggaacccct atttgtttat ttttctaaat 4980
acattcaaat atgtatccgc tcatgagaca ataaccctga taaatgcttc aataatattg 5040
aaaaaggaag agtatgagta ttcaacattt ccgtgtcgcc cttattccct tttttgcggc 5100
attttgcctt cctgtttttg ctcacccaga aacgctggtg aaagtaaaag atgctgaaga 5160
tcagttgggt gcacgagtgg gttacatcga actggatctc aacagcggta agatccttga 5220
gagttttcgc cccgaagaac gttttccaat gatgagcact tttaaagttc tgctatgtgg 5280
cgcggtatta tcccgtattg acgccgggca agagcaactc ggtcgccgca tacactattc 5340
tcagaatgac ttggttgagt actcaccagt cacagaaaag catcttacgg atggcatgac 5400
agtaagagaa ttatgcagtg ctgccataac catgagtgat aacactgcgg ccaacttact 5460
tctgacaacg atcggaggac cgaaggagct aaccgctttt ttgcacaaca tgggggatca 5520
tgtaactcgc cttgatcgtt gggaaccgga gctgaatgaa gccataccaa acgacgagcg 5580
tgacaccacg atgcctgtag caatggcaac aacgttgcgc aaactattaa ctggcgaact 5640
acttactcta gcttcccggc aacaattaat agactggatg gaggcggata aagttgcagg 5700
accacttctg cgctcggccc ttccggctgg ctggtttatt gctgataaat ctggagccgg 5760
tgagcgtgga agccgcggta tcattgcagc actggggcca gatggtaagc cctcccgtat 5820
cgtagttatc tacacgacgg ggagtcaggc aactatggat gaacgaaata gacagatcgc 5880
tgagataggt gcctcactga ttaagcattg gtaactgtca gaccaagttt actcatatat 5940
actttagatt gatttaaaac ttcattttta atttaaaagg atctaggtga agatcctttt 6000
tgataatctc atgaccaaaa tcccttaacg tgagttttcg ttccactgag cgtcagaccc 6060
cgtagaaaag atcaaaggat cttcttgaga tccttttttt ctgcgcgtaa tctgctgctt 6120
gcaaacaaaa aaaccaccgc taccagcggt ggtttgtttg ccggatcaag agctaccaac 6180
tctttttccg aaggtaactg gcttcagcag agcgcagata ccaaatactg ttcttctagt 6240
gtagccgtag ttaggccacc acttcaagaa ctctgtagca ccgcctacat acctcgctct 6300
gctaatcctg ttaccagtgg ctgctgccag tggcgataag tcgtgtctta ccgggttgga 6360
ctcaagacga tagttaccgg ataaggcgca gcggtcgggc tgaacggggg gttcgtgcac 6420
acagcccagc ttggagcgaa cgacctacac cgaactgaga tacctacagc gtgagctatg 6480
agaaagcgcc acgcttcccg aagggagaaa ggcggacagg tatccggtaa gcggcagggt 6540
cggaacagga gagcgcacga gggagcttcc agggggaaac gcctggtatc tttatagtcc 6600
tgtcgggttt cgccacctct gacttgagcg tcgatttttg tgatgctcgt caggggggcg 6660
gagcctatgg aaaaacgcca gcaacgcggc ctttttacgg ttcctggcct tttgctggcc 6720
ttttgctcac atgt 6734

<210> SEQ ID NO 34
<211> LENGTH: 6015
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 34

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc ttctagacaa ctttgtatag aaaagttggg gctggaagct    180
acctttgaca tcatttcctc tgcgaatgca tgtataattt ctacagaacc tattagaaag    240
gatcacccag cctctgcttt tgtacaactt tcccttaaaa aactgccaat tccactgctg    300
tttggcccaa tagtgagaac tttttcctgc tgcctcttgg tgcttttgcc tatggcccct    360
attctgcctg ctgaagacac tcttgccagc atggacttaa acccctccag ctctgacaat    420
cctctttctc ttttgtttta catgaagggt ctggcagcca aagcaatcac tcaaagttca    480
aaccttatca tttttgctt tgttcctctt ggccttggtt ttgtacatca gctttgaaaa    540
taccatccca gggttaatgc tggggttaat ttataactaa gagtgctcta gttttgcaat    600
acaggacatg ctataaaaat ggaaagatca agtttgtaca aaaaagcagg ctgccaccat    660
gtgttcatgt cctactgttc aagcctccaa gctgtgcctt gggtggcttt ggggcatgga    720
caagagccag acatgataag atacattgat gagtttggac aaaccacaac tagaatgcag    780
tgaaaaaaat gctttatttg tgaaatttgt gatgctattg ctttatttgt aaccattata    840
agctgcaata aacaagttta tgatgtttta aagaaaagtt ttttccggag gaaattaaag    900
caaccaggca tctgtttata aatccctttc accgaaacag cattagcgac cctaagcagg    960
agggactgca ggtcttcaga gtgagcccac tgctcaaaga tgtcgtccag ggtctcaacg   1020
taccaggagc cactcttggg gtccctccag gaaacaaaac ctgggaaagt agagtaggac   1080
acaaagatgt cactgggtgt gggcaaacta gatatggcgt ccagctggtc gaaggtcctc   1140
aaaccttcct ggaacggggt ggcatctggc tcggggttac tgccagggga ctcgtcttca   1200
ggggaagtgg aggccacctc aaacccatgg tctttctgct ccccaccaca ggcctggatg   1260
aaaaagagct tgggcttccc tcccaggctg gggcagctgg tcccattgaa gatgttcaca   1320
atcttctcga ccgacacagg gcatccatct gtgccgtaga cagcccctgg gaactgcagg   1380
tggctggcct gacagccgtg agagagaatg accaccacgc agcagtccag agcaccgtgg   1440
tcctgctgcg ccagctccag caaagccagc accattttct tggcagtcag gtcgcccttc   1500
acctccacca tgaaatgcag cgaggagaag cgacgccgca acttctcaca gtcgatgttg   1560
gagccagtgc gggtgcggag cccggactca cggcagaagt tcacattgtt gataatgagg   1620
cagtggccac agggctccat gctcaggatg taagccaaat ctgcatttcc cctcaaactc   1680
tcaagagcac cgacatcacc aaatcctcca gaaccaatgt ccactggtct gggtgtttcc   1740
ggtctgagaa cctctggttt gcgaatctct ggtctgagca ccactggggt aaggttttct   1800
agggttggct tcgacaactt tgctgcttgc ctgttagttc gcagaaacga agccagcatg   1860
tcctggcctg tgtcctctaa gcaggagatg aacaaaggaa gagcctgact ccctcgagtc   1920
tccagatcta tgatcagctg cctggcctga tcccgccgag atccagagcc tgcccgctgg   1980
atgtcctcga tcatatgggg cctgaacagc tcgcggctca gcagggcgtc ccagagctgg   2040
tccacctgca gctcttccac cagccgcagc cggcaccgcc gcaggagccg ccgatccgct   2100
tcgtccatcc tgtgttctgg cggcaaaccc gttgcgaaaa agaacgttca cggcgactac   2160
tgcacttata tacggttctc ccccaccctc gggaaaaagg cggagccagt acacgacatc   2220
actttcccag tttaccccgc gccaccttct ctaggcaccg gatcaattgc cgacccctcc   2280
ccccaacttc tcggggactg tgggcgatgt gcgctctgcc cactgacggg caccggagcc   2340
```

-continued

```
tgttcatgtc ctactgttca agcctccaag ctgtgccttg ggtggctttg gggcatggac   2400
ataaacccag ctttcttgta caaagtggga attccgataa tcaacctctg gattacaaaa   2460
tttgtgaaag attgactggt attcttaact atgttgctcc ttttacgcta tgtggatacg   2520
ctgctttaat gcctttgtat catgctattg cttcccgtat ggctttcatt ttctcctcct   2580
tgtataaatc ctggttgctg tctctttatg aggagttgtg gcccgttgtc aggcaacgtg   2640
gcgtggtgtg cactgtgttt gctgacgcaa cccccactgg ttggggcatt gccaccacct   2700
gtcagctcct ttccgggact ttcgctttcc ccctccctat tgccacggcg gaactcatcg   2760
ccgcctgcct tgcccgctgc tggacagggg ctcggctgtt gggcactgac aattccgtgg   2820
tgttgtcggg gaagctgacg tcctttccat ggctgctcgc ctgtgttgcc acctggattc   2880
tgcgcgggac gtccttctgc tacgtccctt cggccctcaa tccagcggac cttccttccc   2940
gcggcctgct gccggctctg cggcctcttc cgcgtcttcg ccttcgccct cagacgagtc   3000
ggatctccct ttgggccgcc tccccgcatc gggaattcct agagctcgct gatcagcctc   3060
gactgtgcct tctagttgcc agccatctgt tgtttgcccc tcccccgtgc cttccttgac   3120
cctggaaggt gccactccca ctgtcctttc ctaataaaat gaggaaattg catcgcattg   3180
tctgagtagg tgtcattcta ttctgggggg tggggtgggg caggacagca agggggagga   3240
ttgggaagag aatagcaggc atgctgggga gggccgcagg aacccctagt gatggagttg   3300
gccactccct ctctgcgcgc tcgctcgctc actgaggccg ggcgaccaaa ggtcgcccga   3360
cgcccgggct ttgcccgggc ggcctcagtg agcgagcgag cgcgcagctg cctgcagggg   3420
cgcctgatgc ggtattttct ccttacgcat ctgtgcggta tttcacaccg catacgtcaa   3480
agcaaccata gtacgcgccc tgtagcggcg cattaagcgc ggcgggggtg gtggttacgc   3540
gcagcgtgac cgctacactt gccagcgcct tagcgcccgc tcctttcgct ttcttccctt   3600
cctttctcgc cacgttcgcc ggctttcccc gtcaagctct aaatcggggg ctccctttag   3660
ggttccgatt tagtgcttta cggcacctcg accccaaaaa acttgatttg ggtgatggtt   3720
cacgtagtgg gccatcgccc tgatagacgg tttttcgccc tttgacgttg gagtccacgt   3780
tctttaatag tggactcttg ttccaaactg gaacaacact caactctatc tcgggctatt   3840
cttttgattt ataagggatt ttgccgattt cggtctattg gttaaaaaat gagctgattt   3900
aacaaaaatt taacgcgaat tttaacaaaa tattaacgtt tacaatttta tggtgcactc   3960
tcagtacaat ctgctctgat gccgcatagt taagccagcc ccgacacccg ccaacacccg   4020
ctgacgcgcc ctgacgggct tgtctgctcc cggcatccgc ttacagacaa gctgtgaccg   4080
tctccgggag ctgcatgtgt cagaggtttt caccgtcatc accgaaacgc gcgagacgaa   4140
agggcctcgt gatacgccta tttttatagg ttaatgtcat gataataatg gtttcttaga   4200
cgtcaggtgg cacttttcgg ggaaatgtgc gcggaacccc tatttgttta tttttctaaa   4260
tacattcaaa tatgtatccg ctcatgagac aataaccctg ataaatgctt caataatatt   4320
gaaaaaggaa gagtatgagt attcaacatt tccgtgtcgc ccttattccc ttttttgcgg   4380
cattttgcct tcctgttttt gctcacccag aaacgctggt gaaagtaaaa gatgctgaag   4440
atcagttggg tgcacgagtg ggttacatcg aactggatct caacagcggt aagatccttg   4500
agagttttcg ccccgaagaa cgttttccaa tgatgagcac ttttaaagtt ctgctatgtg   4560
gcgcggtatt atcccgtatt gacgccgggc aagagcaact cggtcgccgc atacactatt   4620
ctcagaatga cttggttgag tactcaccag tcacagaaaa gcatcttacg gatggcatga   4680
cagtaagaga attatgcagt gctgccataa ccatgagtga taacactgcg gccaacttac   4740
```

ttctgacaac gatcggagga ccgaaggagc taaccgcttt tttgcacaac atgggggatc 4800
atgtaactcg ccttgatcgt tgggaaccgg agctgaatga agccatacca aacgacgagc 4860
gtgacaccac gatgcctgta gcaatggcaa caacgttgcg caaactatta actggcgaac 4920
tacttactct agcttcccgg caacaattaa tagactggat ggaggcggat aaagttgcag 4980
gaccacttct gcgctcggcc cttccggctg gctggtttat tgctgataaa tctggagccg 5040
gtgagcgtgg aagccgcggt atcattgcag cactggggcc agatggtaag ccctcccgta 5100
tcgtagttat ctacacgacg gggagtcagg caactatgga tgaacgaaat agacagatcg 5160
ctgagatagg tgcctcactg attaagcatt ggtaactgtc agaccaagtt tactcatata 5220
tactttagat tgatttaaaa cttcattttt aatttaaaag gatctaggtg aagatccttt 5280
ttgataatct catgaccaaa atcccttaac gtgagttttc gttccactga gcgtcagacc 5340
ccgtagaaaa gatcaaagga tcttcttgag atcctttttt tctgcgcgta atctgctgct 5400
tgcaaacaaa aaaaccaccg ctaccagcgg tggtttgttt gccggatcaa gagctaccaa 5460
ctctttttcc gaaggtaact ggcttcagca gagcgcagat accaaatact gttcttctag 5520
tgtagccgta gttaggccac cacttcaaga actctgtagc accgcctaca tacctcgctc 5580
tgctaatcct gttaccagtg gctgctgcca gtggcgataa gtcgtgtctt accgggttgg 5640
actcaagacg atagttaccg gataaggcgc agcggtcggg ctgaacgggg ggttcgtgca 5700
cacagcccag cttggagcga acgacctaca ccgaactgag atacctacag cgtgagctat 5760
gagaaagcgc cacgcttccc gaagggagaa aggcggacag gtatccggta agcggcaggg 5820
tcggaacagg agagcgcacg agggagcttc cagggggaaa cgcctggtat ctttatagtc 5880
ctgtcgggtt tcgccacctc tgacttgagc gtcgattttt gtgatgctcg tcaggggggc 5940
ggagcctatg gaaaaacgcc agcaacgcgg cctttttacg gttcctggcc ttttgctggc 6000
cttttgctca catgt 6015

<210> SEQ ID NO 35
<211> LENGTH: 3177
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35
taatacgact cactataggc atgaagacag tgtttagcaa gattgttttt ttgtcattct 60
cctaagaagc tattaaaatc acatggggat agcactacta aaattaattt tacacattag 120
ggctcttcca tataggcagc tctccctagc attgttcact gtacactcga tcgtactccg 180
cgtggcctcg gtgaaaatgt ggtggctctt tcaagtcctc cctaatgtta cacactgatt 240
aaagattgtt acaatgagct acctactgat cgcctgacac gatttcctgc acaggcttga 300
gccatatact catacatcgc atcttggcca cgttttccac gggtttcaaa attaatctca 360
agttctacgc ttaacgcttt cgcctgttcc cagttattaa tatattcaac gctagaactc 420
ccctcagcga agggaaggct gagcactaca cgcgaagcac catcaccgaa ccttttgata 480
aactcttccg ttccgacttg ctccatcaac ggttcagtga gacttaaacc taactctttc 540
ttaatagttt cggcattatc cacttttagt gcgagaacct tcgtcagtcc tggatacgtc 600
actttgacca cgcctccagc ttttccagag agcgggtttt cattatctac agagtatccc 660
gcagcgtcgt atttattgtc ggtactataa aaccctttcc aatcatcgtc ataatttcct 720

-continued

```
tgtgtaccag attttggctt ttgtatacct ttttgaatgg aatctacata accaggttta    780
gtcccgtggt acgaagaaaa gttttccatc acaaaagatt tagaagaatc aacaacatca    840
tcagcgccca tcttaccttt cggtcacacc cggacgaaac ctagatgtgc tgatgatcgg    900
ctgcaacacg gacgaaaccg taagcagcct gcagaagata gacgagttac tcgtgtcctg    960
tcaacgacag taattagtta ttaattatac tgcgtgagtg cactaagcat gcagccgagt   1020
gacagccaca cagattttaa agttcgttta gagaacagat ctacaagaga tcgaaagttg   1080
gttggtttgt tacctgggaa ggtataaacc tttaataaaa aaaaaaaaaa aaaaaaaaaa   1140
aaaaaatgaa gagccgtacg ggcgcgccta ggcgcgattc cgcttcctcg ctcactgact   1200
cgctgcgctc ggtcgttcgg ctgcggcgag cggtatcagc tcactcaaag gcggtaatac   1260
ggttatccac agaatcaggg gataacgcag gaaagaacat gtgagcaaaa ggccagcaaa   1320
aggccaggaa ccgtaaaaag gccgcgttgc tggcgttttt ccataggctc cgcccccctg   1380
acgagcatca caaaaatcga cgctcaagtc agaggtggcg aaacccgaca ggactataaa   1440
gataccaggc gtttccccct ggaagctccc tcgtgcgctc tcctgttccg accctgccgc   1500
ttaccggata cctgtccgcc tttctccctt cgggaagcgt ggcgctttct catagctcac   1560
gctgtaggta tctcagttcg gtgtaggtcg ttcgctccaa gctgggctgt gtgcacgaac   1620
cccccgttca gcccgaccgc tgcgccttat ccggtaacta tcgtcttgag tccaacccgg   1680
taagacacga cttatcgcca ctggcagcag ccactggtaa caggattagc agagcgaggt   1740
atgtaggcgg tgctacagag ttcttgaagt ggtggcctaa ctacggctac actagaagaa   1800
cagtatttgg tatctgcgct ctgctgaagc cagttacctt cggaaaaaga gttggtagct   1860
cttgatccgg caaacaaacc accgctggta gcggtggttt ttttgtttgc aagcagcaga   1920
ttacgcgcag aaaaaaagga tctcaagaag atcctttgat cttttctacg gggtctgacg   1980
ctcagtggaa cgaaaactca cgttaaggga ttttggtcat gagattatca aaaaggatct   2040
tcacctagat ccttttaaat taaaaatgaa gttttaaatc aatctaaagt atatatgagt   2100
aaacttggtc tgacagttac caatgcttaa tcagtgaggc acctatctca gcgatctgtc   2160
tatttcgttc atccatagtt gcctgactcc ccgtcgtgta gataactacg atacgggagg   2220
gcttaccatc tggccccagt gctgcaatga taccgcgaga tccacgctca ccggctccag   2280
atttatcagc aataaaccag ccagccggaa gggccgagcg cagaagtggt cctgcaactt   2340
tatccgcctc catccagtct attaattgtt gccgggaagc tagagtaagt agttcgccag   2400
ttaatagttt gcgcaacgtt gttgccattg ctacaggcat cgtggtgtca cgctcgtcgt   2460
ttggtatggc ttcattcagc tccggttccc aacgatcaag gcgagttaca tgatccccca   2520
tgttgtgcaa aaaagcggtt agctccttcg gtcctccgat cgttgtcaga agtaagttgg   2580
ccgcagtgtt atcactcatg gttatggcag cactgcataa ttctcttact gtcatgccat   2640
ccgtaagatg cttttctgtg actggtgagt actcaaccaa gtcattctga gaatagtgta   2700
tgcggcgacc gagttgctct tgcccggcgt caatacggga taataccgcg ccacatagca   2760
gaactttaaa agtgctcatc attggaaaac gttcttcggg gcgaaaactc tcaaggatct   2820
taccgctgtt gagatccagt tcgatgtaac ccactcgtgc acccaactga tcttcagcat   2880
cttttacttt caccagcgtt tctgggtgag caaaaacagg aaggcaaaat gccgcaaaaa   2940
agggaataag ggcgacacgg aaatgttgaa tactcatact cttccttttt caatattatt   3000
gaagcattta tcagggttat tgtctcatga gcggatacat atttgaatgt atttagaaaa   3060
```

ataaacaaat aggggttccg cgcacatttc cccgaaaagt gccacctgac gtctaagaaa 3120
ccattattat catgacatta acctataaaa ataggcgtat cacgaggccc tttcgtc 3177

<210> SEQ ID NO 36
<211> LENGTH: 6079
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 36
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc ttctagacaa ctttgtatag aaaagttggg ctccggtgcc 180
cgtcagtggg cagagcgcac atcgcccaca gtccccgaga agttgggggg aggggtcggc 240
aattgaaccg gtgcctagag aaggtggcgc ggggtaaact gggaaagtga tgtcgtgtac 300
tggctccgcc tttttcccga gggtggggga gaaccgtata taagtgcagt agtcgccgtg 360
aacgttcttt ttcgcaacgg gtttgccgcc agaacacagg taagtgccgt gtgtggttcc 420
cgcgggcctg gcctctttac gggttatggc ccttgcgtgc cttgaattac ttccacctgg 480
ctgcagtacg tgattcttga tcccgagctt cgggttggaa gtgggtggga gagttcgagg 540
ccttgcgctt aaggagcccc ttcgcctcgt gcttgagttg aggcctggcc tgggcgctgg 600
ggccgccgcg tgcgaatctg gtggcacctt cgcgcctgtc tcgctgcttt cgataagtct 660
ctagccattt aaaatttttg atgacctgct gcgacgcttt ttttctggca agatagtctt 720
gtaaatgcgg gccaagatct gcacactggt atttcggttt ttggggccgc gggcggcgac 780
ggggcccgtg cgtcccagcg cacatgttcg gcgaggcggg gcctgcgagc gcggccaccg 840
agaatcggac gggggtagtc tcaagctggc cggcctgctc tggtgcctgg tctcgcgccg 900
ccgtgtatcg ccccgccctg ggcggcaagg ctggcccggt cggcaccagt tgcgtgagcg 960
gaaagatggc cgcttcccgg ccctgctgca gggagctcaa aatggaggac gcggcgctcg 1020
ggagagcggg cgggtgagtc acccacacaa aggaaaaggg cctttccgtc ctcagccgtc 1080
gcttcatgtg actccacgga gtaccgggcg ccgtccaggc acctcgatta gttctcgagc 1140
ttttggagta cgtcgtcttt aggttggggg gaggggtttt atgcgatgga gtttccccac 1200
actgagtggg tggagactga agttaggcca gcttggcact tgatgtaatt ctccttggaa 1260
tttgcccttt ttgagtttgg atcttggttc attctcaagc ctcagacagt ggttcaaagt 1320 tttttcttc catttcaggt gtcgtgacaa gtttgtacaa aaaagcaggc tcatgaagac 1380
agtgtttagc aagattgttt ttttgtcatt ctcctaagaa gctattaaaa tcacatgggg 1440
atagcactac taaaattaat tttacacatt agggctcttc catataggca gctctcccta 1500
gcattgttca ctgtacactc gatcgtactc cgcgtggcct cggtgaaaat gtggtggctc 1560
tttcaagtcc tccctaatgt tacacactga ttaaagattg ttacaatgag ctacctactg 1620
atcgcctgac acgatttcct gcacaggctt gagccatata ctcatacatc gcatcttggc 1680
cacgttttcc acgggtttca aaattaatct caagttctac gcttaacgct ttcgcctgtt 1740
cccagttatt aatatattca acgctagaac tcccctcagc gaagggaagg ctgagcacta 1800
cacgcgaagc accatcaccg aaccttttga taaactcttc cgttccgact tgctccatca 1860
acggttcagt gagacttaaa cctaactctt tcttaatagt ttcggcatta tccactttta 1920
gtgcgagaac cttcgtcagt cctggatacg tcactttgac cacgcctcca gcttttccag 1980
agagcgggtt ttcattatct acagagtatc ccgcagcgtc gtatttattg tcggtactat 2040
aaaacccttt ccaatcatcg tcataatttc cttgtgtacc agattttggc ttttgtatac 2100
ctttttgaat ggaatctaca taaccaggtt tagtcccgtg gtacgaagaa aagttttcca 2160
tcacaaaaga tttagaagaa tcaacaacat catcagcgcc catcttacct ttcggtcaca 2220
cccggacgaa acctagatgt gctgatgatc ggctgcaaca cggacgaaac cgtaagcagc 2280
ctgcagaaga tagacgagtt actcgtgtcc tgtcaacgac agtaattagt tattaattat 2340
actgcgtgag tgcactaagc atgcagccga gtgacagcca cacagatttt aaagttcgtt 2400
tagagaacag atctacaaga gatcgaaagt tggttggttt gttacctggg aaggtataaa 2460
cctttaatac ccagctttct tgtacaaagt gggaattccg ataatcaacc tctggattac 2520
aaaatttgtg aaagattgac tggtattctt aactatgttg ctccttttac gctatgtgga 2580
tacgctgctt taatgccttt gtatcatgct attgcttccc gtatggcttt cattttctcc 2640
tccttgtata aatcctggtt gctgtctctt tatgaggagt tgtggcccgt tgtcaggcaa 2700
cgtggcgtgg tgtgcactgt gtttgctgac gcaaccccca ctggttgggg cattgccacc 2760
acctgtcagc tcctttccgg gactttcgct ttccccctcc ctattgccac ggcggaactc 2820
atcgccgcct gccttgcccg ctgctggaca ggggctcggc tgttgggcac tgacaattcc 2880
gtggtgttgt cggggaagct gacgtccttt ccatggctgc tcgcctgtgt tgccacctgg 2940
attctgcgcg ggacgtcctt ctgctacgtc ccttcggccc tcaatccagc ggaccttcct 3000
tcccgcggcc tgctgccggc tctgcggcct cttccgcgtc ttcgccttcg ccctcagacg 3060
agtcggatct ccctttgggc cgcctccccg catcgggaat tcctagagct cgctgatcag 3120
cctcgactgt gccttctagt tgccagccat ctgttgtttg cccctccccc gtgccttcct 3180
tgaccctgga aggtgccact cccactgtcc tttcctaata aaatgaggaa attgcatcgc 3240
attgtctgag taggtgtcat tctattctgg ggggtggggt ggggcaggac agcaaggggg 3300
aggattggga agagaatagc aggcatgctg gggagggccg caggaacccc tagtgatgga 3360
gttggccact ccctctctgc gcgctcgctc gctcactgag gccgggcgac caaaggtcgc 3420
ccgacgcccg ggctttgccc gggcggcctc agtgagcgag cgagcgcgca gctgcctgca 3480
ggggcgcctg atgcggtatt ttctccttac gcatctgtgc ggtatttcac accgcatacg 3540
tcaaagcaac catagtacgc gccctgtagc ggcgcattaa gcgcggcggg ggtggtggtt 3600
acgcgcagcg tgaccgctac acttgccagc gccttagcgc ccgctccttt cgctttcttc 3660
ccttcctttc tcgccacgtt cgccggcttt ccccgtcaag ctctaaatcg ggggctccct 3720
ttagggttcc gatttagtgc tttacggcac ctcgacccca aaaaacttga tttgggtgat 3780
ggttcacgta gtgggccatc gccctgatag acggtttttc gccctttgac gttggagtcc 3840
acgttcttta atagtggact cttgttccaa actggaacaa cactcaactc tatctcgggc 3900
tattcttttg atttataagg gattttgccg atttcggtct attggttaaa aaatgagctg 3960
atttaacaaa aatttaacgc gaattttaac aaaatattaa cgtttacaat tttatggtgc 4020
actctcagta caatctgctc tgatgccgca tagttaagcc agccccgaca cccgccaaca 4080
cccgctgacg cgccctgacg ggcttgtctg ctcccggcat ccgcttacag acaagctgtg 4140
accgtctccg ggagctgcat gtgtcagagg ttttcaccgt catcaccgaa acgcgcgaga 4200
cgaaagggcc tcgtgatacg cctattttta taggttaatg tcatgataat aatggtttct 4260
tagacgtcag gtggcacttt tcggggaaat gtgcgcggaa cccctatttg tttatttttc 4320

-continued

```
taaatacatt caaatatgta tccgctcatg agacaataac cctgataaat gcttcaataa   4380
tattgaaaaa ggaagagtat gagtattcaa catttccgtg tcgcccttat tccctttttt   4440
gcggcatttt gccttcctgt ttttgctcac ccagaaacgc tggtgaaagt aaaagatgct   4500
gaagatcagt tgggtgcacg agtgggttac atcgaactgg atctcaacag cggtaagatc   4560
cttgagagtt ttcgccccga agaacgtttt ccaatgatga gcacttttaa agttctgcta   4620
tgtggcgcgg tattatcccg tattgacgcc gggcaagagc aactcggtcg ccgcatacac   4680
tattctcaga atgacttggt tgagtactca ccagtcacag aaaagcatct tacggatggc   4740
atgacagtaa gagaattatg cagtgctgcc ataaccatga gtgataacac tgcggccaac   4800
ttacttctga caacgatcgg aggaccgaag gagctaaccg cttttttgca caacatgggg   4860
gatcatgtaa ctcgccttga tcgttgggaa ccggagctga atgaagccat accaaacgac   4920
gagcgtgaca ccacgatgcc tgtagcaatg gcaacaacgt tgcgcaaact attaactggc   4980
gaactactta ctctagcttc ccggcaacaa ttaatagact ggatggaggc ggataaagtt   5040
gcaggaccac ttctgcgctc ggcccttccg gctggctggt ttattgctga taaatctgga   5100
gccggtgagc gtggaagccg cggtatcatt gcagcactgg ggccagatgg taagccctcc   5160
cgtatcgtag ttatctacac gacggggagt caggcaacta tggatgaacg aaatagacag   5220
atcgctgaga taggtgcctc actgattaag cattggtaac tgtcagacca agtttactca   5280
tatatacttt agattgattt aaaacttcat ttttaattta aaaggatcta ggtgaagatc   5340
ctttttgata atctcatgac caaaatccct taacgtgagt tttcgttcca ctgagcgtca   5400
gaccccgtag aaaagatcaa aggatcttct tgagatcctt tttttctgcg cgtaatctgc   5460
tgcttgcaaa caaaaaaacc accgctacca gcggtggttt gtttgccgga tcaagagcta   5520
ccaactcttt ttccgaaggt aactggcttc agcagagcgc agataccaaa tactgttctt   5580
ctagtgtagc cgtagttagg ccaccacttc aagaactctg tagcaccgcc tacatacctc   5640
gctctgctaa tcctgttacc agtggctgct gccagtggcg ataagtcgtg tcttaccggg   5700
ttggactcaa gacgatagtt accggataag gcgcagcggt cgggctgaac ggggggttcg   5760
tgcacacagc ccagcttgga gcgaacgacc tacaccgaac tgagatacct acagcgtgag   5820
ctatgagaaa gcgccacgct tcccgaaggg agaaaggcgg acaggtatcc ggtaagcggc   5880
agggtcggaa caggagagcg cacgagggag cttccagggg gaaacgcctg gtatctttat   5940
agtcctgtcg ggtttcgcca cctctgactt gagcgtcgat ttttgtgatg ctcgtcaggg   6000
gggcggagcc tatggaaaaa cgccagcaac gcggcctttt tacggttcct ggccttttgc   6060
tggccttttg ctcacatgt                                                6079
```